United States Patent
Barberousse et al.

(10) Patent No.: US 8,093,394 B2
(45) Date of Patent: Jan. 10, 2012

(54) DERIVATIVES OF 5-THIOXYLOPYRANOSE AND USE OF SAME FOR TREATMENT

(75) Inventors: Véronique Barberousse, Hauteville-les-Dijon (FR); Didier Thomas, Saint Apollinaire (FR); Michel Bondoux, Fontaine les Dijon (FR)

(73) Assignee: Laboratoires Fournier S.A., Dijon Cedex (FR)

( * ) Notice: Subject to any disclaimer, the term of this patent is extended or adjusted under 35 U.S.C. 154(b) by 468 days.

(21) Appl. No.: 12/411,783

(22) Filed: Mar. 26, 2009

(65) Prior Publication Data

US 2009/0182013 A1    Jul. 16, 2009

Related U.S. Application Data

(63) Continuation of application No. PCT/FR2007/052005, filed on Sep. 26, 2007.

(30) Foreign Application Priority Data

Sep. 27, 2006 (FR) ..................... 06 53961

(51) Int. Cl.
*C07H 17/02* (2006.01)
*A61K 31/44* (2006.01)
*C07D 409/12* (2006.01)
*C07D 409/14* (2006.01)

(52) U.S. Cl. .................. 546/282.1; 544/333; 546/268.4; 546/280.1; 546/256; 546/272.1; 546/275.4; 546/270.4; 514/256; 514/340

(58) Field of Classification Search ........................ None
See application file for complete search history.

(56) References Cited

U.S. PATENT DOCUMENTS

| | | |
|---|---|---|
| 4,432,973 A | 2/1984 | Picart |
| 4,877,808 A | 10/1989 | Samreth et al. |
| 5,101,048 A | 3/1992 | Bajgrowicz et al. |
| 5,169,838 A | 12/1992 | Samreth et al. |

FOREIGN PATENT DOCUMENTS

| | | |
|---|---|---|
| EP | 0 051 023 B1 | 5/1982 |
| EP | 0 290 321 A1 | 11/1988 |
| EP | 0 365 397 A2 | 4/1990 |
| EP | 421 829 B1 | 4/1991 |
| EP | 1 609 799 A1 | 12/2005 |
| WO | WO 2005/030785 A2 * | 4/2005 |
| WO | WO 2005/030785 A2 | 4/2005 |

OTHER PUBLICATIONS

International Search Report dated Mar. 11, 2008 with partial English translation (Six (6) pages).

* cited by examiner

*Primary Examiner* — Laura L. Stockton
(74) *Attorney, Agent, or Firm* — Crowell & Moring LLP

(57) ABSTRACT

The invention relates to new compounds of 5-thioxilose, preferably derivatives of the 5-thioxilopyranose type, and to a method for preparing the same and their use as the active ingredient of drugs mainly intended for treating or inhibiting thrombosis or heart failure or thromboembolic diseases.

20 Claims, No Drawings

DERIVATIVES OF 5-THIOXYLOPYRANOSE AND USE OF SAME FOR TREATMENT

CROSS REFERENCE TO RELATED APPLICATIONS

This application is a continuation of international patent application no. PCT/FR2007/052005, filed Sep. 26, 2007, designating the United States of America, and published in French on Apr. 3, 2008 as WO 2008/037922, the entire disclosure of which is incorporated herein by reference. Priority is claimed based on French patent application no. FR 0653961, filed Sep. 27, 2006.

FIELD OF THE INVENTION

The present invention relates to novel 5-thioxylose compounds, preferably derivatives of 5-thioxylopyranose type, and to their process of preparation and their use as active substance of medicaments, in particular intended for the treatment or inhibition of thrombosis.

PRIOR ART

D-Xylose derivatives are already known, for example in EP 051 023 B1, U.S. Pat. No. 4,877,808 or EP 421 829 B1 or in the publication J. Med. Chem. Vol. 36, No. 7, pp 898-903. The compounds described in these documents are of use in reducing the risks of venous thrombosis in man. The mechanism of action of these compounds appears to be an effect on glycosaminoglycans (J. Biol. Chem., Vol. 270, No. 6, pp 2662-68, Thromb. Haemost., 1999, 81, pp 945-950). The document WO 2005/030785 describes pyridinyl 5-thio-β-D-xylopyranosides exhibiting an activity in treating venous thrombosis.

Furthermore, it is known that the beneficial effects of a transluminal coronary angioplasty can be compromised due to restenosis of the vessel, thus causing a fresh obstruction of the arterial lumen. Compounds which make it possible to avoid this restenosis are thus of the greatest advantage in maintaining a satisfactory diagnosis following the surgical operation with regard to artherosclerosis.

Novel compounds have now been discovered, and this is the subject matter of the present invention, which exhibit a good effectiveness when they are administered orally with an excellent pharmacological result (generally approximately 100%) against the appearance of arterial or venous thrombosis.

DESCRIPTION

The novel compounds according to the invention are characterized in that they are chosen from:
a) the compounds of formula:

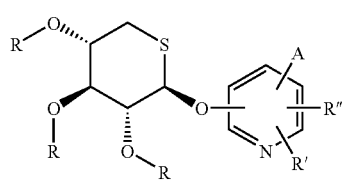

I in which:
the pentapyranosyl group represents a 5-thio-β-D-xylopyranosyl group, R represents a hydrogen atom or a $C_2$-$C_6$ acyl group,
R' and R" each independently represent a hydrogen atom, a halogen atom, a $C_1$-$C_4$ alkyl group or a 6-fluoro-3-pyridinyl group,
A represents a 5- or 6-membered aromatic ring of formula:

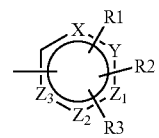

in which:
X represents a nitrogen, oxygen or sulfur atom,
Y represents a carbon atom or a single bond,
$Z_1$, $Z_2$ and $Z_3$ each independently represent a carbon or nitrogen atom,
$R_1$, $R_2$ and $R_3$ each independently represent a hydrogen atom, a halogen atom, a cyano group, a $C_1$-$C_4$ alkyl group, a $C_1$-$C_4$ alkoxy group or a trifluoromethyl group; or
$R_1$ and $R_2$ form, together with the atoms of the heterocycle to which they are attached, an aromatic ring comprising 6 carbon atoms, A thus representing a fused bicyclic group, in particular a benzofuranyl or benzothienyl group,
b) their addition salts,
c) their metabolites.

The invention also relates to the compounds of formula I for their use as pharmacologically active substance.

In particular, the invention relates to the use of at least one substance chosen from the compounds of formula I and their nontoxic salts for the preparation of a medicament, of use in human or animal therapeutics, intended for the inhibition or treatment of thrombosis, in particular venous thrombosis. The compounds according to the invention are also of use as active substances of medicaments intended for the inhibition of restenosis after transluminal coronary angioplasty. As the compounds according to the invention are active according to a method of action involving glycosaminoglycans, they may also be of use as active substance of a medicament intended for the treatment or inhibition of any other disease in which glycosaminoglycans are involved.

DETAILED DESCRIPTION

In the formula I, the term "$C_1$-$C_4$ alkyl group" is understood to mean a saturated, linear or branched, hydrocarbon chain having from 1 to 4 carbon atoms or one which is partially or completely cyclized, the cyclized portion having 3 or 4 carbon atoms. Examples of $C_1$-$C_4$ alkyl groups are in particular the methyl, ethyl, propyl, butyl, 1-methylethyl, 1,1-dimethylethyl, 1-methylpropyl, 2-methylpropyl, cyclopropyl or cyclopropylmethyl groups.

The term "halogen" should be understood as meaning a fluorine, chlorine, bromine or iodine atom and preferably a fluorine or chlorine atom.

The term "$C_2$-$C_6$ acyl group" is understood to mean an R—CO— group in which R represents an alkyl group as defined above having from 1 to 5 carbon atoms. Examples of $C_2$-$C_6$ acyl groups are in particular the acetyl, propanoyl, butanoyl, pentanoyl or hexanoyl groups and their homologs in which the chain can be branched.

The term "$C_1$-$C_4$ alkoxy group" is understood to mean an RO— group in which R represents an alkyl group having from 1 to 4 carbon atoms as defined above. Mention may be made, as examples of $C_1$-$C_4$ alkoxy groups, of the methoxy, ethoxy, propoxy, butoxy, 1-methylethoxy, 1,1-dimethylethoxy, 1-methylpropoxy, 2-methylpropoxy or cyclopropylmethoxy groups.

The term "addition salts" is understood to mean the addition salts obtained by reaction of a compound of formula I with an inorganic or organic acid. Preferably, the addition salts are pharmaceutically acceptable addition salts. The hydrates or solvates of the compounds of formula I or of the salts of the compounds of formula I also form an integral part of the invention.

Preference is given, among the inorganic acids suitable for salifying a basic compound of formula I, to hydrochloric, hydrobromic, phosphoric and sulfuric acids. Preference is given, among the organic acids suitable for salifying a basic compound of formula I, to methanesulfonic, benzenesulfonic, toluenesulfonic, maleic, fumaric, oxalic, citric, tartaric, lactic and trifluoroacetic acids.

The term "active metabolites" is understood to mean the compounds which are produced in the biological medium from the compounds of formula I and which have a pharmacological activity of the same nature as the compounds of formula I which are described in the present patent application. By way of example, the compounds of formula I can be metabolized as the result of a hydroxylation reaction to provide a novel compound (metabolite) which retains a pharmacological activity of the same nature as that of the compounds of formula I.

Mention may be made, as specific examples of fused bicyclic groups represented by A in the case where $R_1$ and $R_2$ together form an aromatic ring comprising 6 carbon atoms, of the benzofuranyl, benzothienyl, benzisoxazolyl, benzoxazolyl, benzimidazolyl, quinolinyl, quinoxalinyl, quinazolinyl, indolyl, benzothiazolyl or indazolyl groups.

Preference is very particularly given, among the compounds according to the present invention, to those in which the thioxyloside group is in the 3 position of a pyridine ring.

Preference is also given, among the compounds according to the present invention, to the compounds in which R is the hydrogen atom or the —$COCH_3$ group.

Other preferred compounds in the context of the present invention are the compounds of abovementioned formula I in which one at least of the following conditions is observed:
  A represents a pyridinyl group which is unsubstituted or substituted by one of the $R_1$, $R_2$ and $R_3$ groups as defined above;
  R' and R" each represent a hydrogen atom, a halogen atom or a methyl group.

The compounds of formula I according to the invention can be prepared by employing the glycosylation methods known to a person skilled in the art, in particular:
  a) the Helferich method described in the work "The Carbohydrate, Chemistry and Biochemistry", $2^{nd}$ edition, Academic Press, New York-London, 1972, Volume IA, pages 292-294, by condensation of a peracetylated sugar with an aromatic hydroxyheterocycle in the presence of a Lewis acid;
  b) the Koenigs-Knorr method (idem, pages 295-299), by condensation of a halogenated acylose with a hydroxyl group having a phenolic nature in the presence of a proton acceptor, such as mercuric cyanide, silver imidazolate or silver trifluoromethanesulfonate;
  c) the Schmidt method, by condensation of an osyl trichloroacetimidate with an aromatic hydroxyheterocycle in the presence of a Lewis acid, such as, for example, trimethylsilyl trifluoromethanesulfonate or boron trifluoride etherate.

The compounds of formula I are preferably prepared according to methods derived from the abovementioned processes.

According to a first general process, the stages consisting in:
  a) reacting a pyridinol of formula:

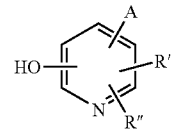

II in which:
R' and R" each independently represent a hydrogen atom, a halogen atom, a $C_1$-$C_4$ alkyl group or a 6-fluoro-3-pyridinyl group,
A represents a 5- or 6-membered aromatic ring of formula:

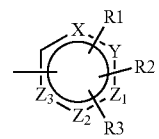

in which:
X represents a nitrogen, oxygen or sulfur atom,
Y represents a carbon atom or a single bond,
$Z_1$, $Z_2$ and $Z_3$ each independently represent a carbon or nitrogen atom,
$R_1$, $R_2$ and $R_3$ each independently represent a hydrogen atom, a halogen atom, a cyano group, a $C_1$-$C_4$ alkyl group, a $C_1$-$C_4$ alkoxy group, or a trifluoromethyl group; or
$R_1$ and $R_2$ form, together with the atoms of the heterocycle to which they are attached, an aromatic ring comprising 6 carbon atoms, A thus representing a fused bicyclic group, in particular a benzofuranyl or benzothienyl group,
with a 5-thioxylopyranose derivative of formula:

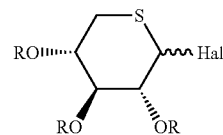

in which Hal represents a halogen, preferably bromine, and R represents a $C_2$-$C_6$ acyl group, preferably the acetyl group, in an aprotic solvent, such as acetonitrile or toluene, in the presence of a silver salt, in particular silver oxide or imidazolate, or of a zinc salt (in particular the oxide or the chloride), in an anhydrous medium, at a temperature of between 25 and 110° C. and for 1 to 10 hours, in order to obtain the compound of formula:

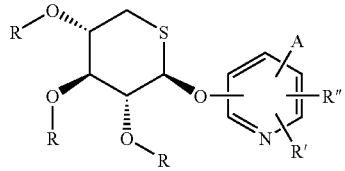

I in which A, R, R' and R" retain the same meanings as in the starting compounds;

b) if necessary, reacting the compound of formula I obtained above with a solution of ammonia in methanol in order to bring about the deacylation and thus to replace the acyl group by hydrogen atoms and to obtain the compound of formula:

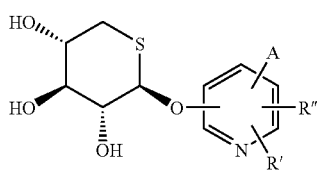

Ia in which $R_1$ and $R_2$ retain the same meanings as above;

c) if necessary, reacting one of the compounds I or Ia obtained above with an acid according to methods known to a person skilled in the art in order to obtain the corresponding addition salt, are carried out.

In an alternative form of stage b) described above, the replacement of the acyl group by a hydrogen atom can be brought about by the action of a metal alkoxide, preferably sodium methoxide in a catalytic amount in methanol, at a temperature of between 0 and 30° C. and for 0.5 to 2 hours, in order to obtain the compound of formula Ia from the compound of formula I in which R represents a $C_2$-$C_6$ acyl group.

According to a second process, the compounds of formula I can be obtained by reaction of tetra-O-acetyl-5-thioxylopyranose of formula:

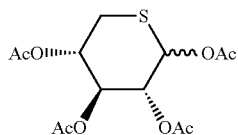

in which Ac represents the acetyl group, with a compound of formula:

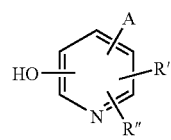

II in which:

R' and R" each independently represent a hydrogen atom, a halogen atom, a $C_1$-$C_4$ alkyl group or a 6-fluoro-3-pyridinyl group, A represents a 5- or 6-membered aromatic ring of formula:

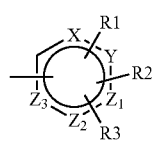

in which:

X represents a nitrogen, oxygen or sulfur atom,

Y represents a carbon atom or a single bond, $Z_1$, $Z_2$ and $Z_3$ each independently represent a carbon or nitrogen atom, $R_1$, $R_2$ and $R_3$ each independently represent a hydrogen atom, a halogen atom, a cyano group, a $C_1$-$C_4$ alkyl group, a $C_1$-$C_4$ alkoxy group or a trifluoromethyl group; or $R_1$ and $R_2$ form, together with the atoms of the heterocycle to which they are attached, an aromatic ring comprising 6 carbon atoms, A thus representing a fused bicyclic group, in particular a benzofuranyl or benzothienyl group, in an aprotic solvent, such as, for example, dichloromethane, in the presence of a catalyst of Lewis acid type, for example tin tetrachloride, at a temperature of between 20 and 60° C. and for 1 to 2 hours, in order to obtain the compound of formula:

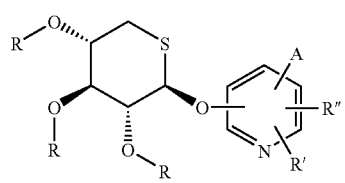

Ib in which A, R, R' and R" retain the same meanings as in the starting compounds.

The compound of formula Ib can subsequently be reacted according to the protocol described in the preceding process in order to obtain the unsubstituted pyranosyl compound and/or a salt with an acid.

According to a third process, the compounds of formula I can be obtained by reacting a thioxylose derivative of formula:

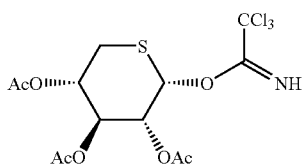

in which Ac represents the acetyl group, with a compound of formula:

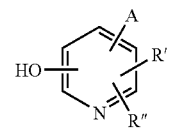

II in which:

R' and R" each independently represent a hydrogen atom, a halogen atom, a $C_1$-$C_4$ alkyl group or a 6-fluoro-3-pyridinyl group, A represents a 5- or 6-membered aromatic ring of formula:

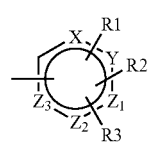

in which:

X represents a nitrogen, oxygen or sulfur atom,

Y represents a carbon atom or a single bond, $Z_1$, $Z_2$ and $Z_3$ each independently represent a carbon or nitrogen atom, $R_1$, $R_2$ and $R_3$ each independently represent a hydrogen atom, a halogen atom, a cyano group, a $C_1$-$C_4$ alkyl group, a $C_1$-$C_4$ alkoxy group or a trifluoromethyl group; or $R_1$ and $R_2$ form, together with the atoms of the heterocycle to which they are attached, an aromatic ring comprising 6 carbon atoms, A thus representing a fused bicyclic group, in particular a benzofuranyl or benzothienyl group, in an aprotic solvent, such as dichloromethane, in the presence of a catalyst, such as trimethylsilyl trifluoromethanesulfonate, at a temperature of between −25° C. and ambient temperature and for 1 to 5 hours, in order to obtain the thioxylopyranoside of formula:

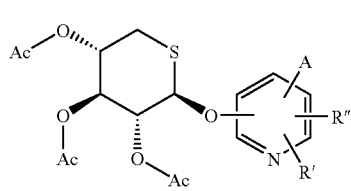

Ib in which A, R' and R" retain the same meanings as in the starting compounds.

The compound of formula Ib thus obtained can subsequently be reacted as above in order to obtain the unsubstituted pyranosyl compounds and/or the acid salts.

The compounds of formula I according to the invention can also be prepared from halogenated derivatives of a glycosylated pyridine by a Suzuki-type coupling reaction between two aromatic rings.

According to a general process, the stages consisting in:
a) reacting a compound of formula:

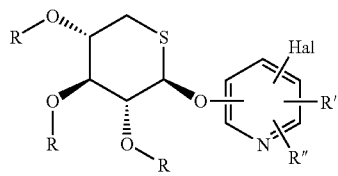

in which Hal is a halogen atom, preferably bromine or iodine, R' and R" each independently represent a hydrogen atom, a halogen atom (other than bromine or iodine) or a $C_1$-$C_4$ alkyl group, and R represents a hydrogen atom or a $C_2$-$C_6$ acyl group;

with a heteroarylboronic acid or an alkyl heteroarylboronate of formula:

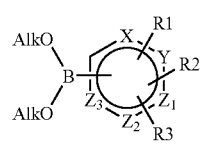

in which:
X represents a nitrogen, oxygen or sulfur atom,
Y represents a carbon atom or a single bond,
$Z_1$, $Z_2$ and $Z_3$ each independently represent a carbon or nitrogen atom, $R_1$, $R_2$ and $R_3$ each independently represent a hydrogen atom, a halogen atom, preferably a fluorine atom, a cyano group, a $C_1$-$C_4$ alkyl group, a $C_1$-$C_4$ alkoxy group or a trifluoromethyl group; or $R_1$ and $R_2$ form, together with the atoms of the heterocycle to which they are attached, an aromatic ring comprising 6 carbon atoms, Alk represents a hydrogen atom or a $C_1$-$C_4$ alkyl group, in the presence of a palladium catalyst, such as the [1,1'-bis(diphenyl-phosphino)ferrocene]dichloropalladium complex with dichloromethane, a palladium catalyst immobilized on resin or Herrmann's catalyst, of a polar solvent, such as methanol or a glycol ether, and of cesium fluoride or sodium carbonate or other inorganic bases, optionally with the addition of lithium chloride, at a temperature of between 70° C. and 150° C. for 5 minutes to 72 hours using microwave radiation or a conventional heating method, in order to obtain the compound of formula:

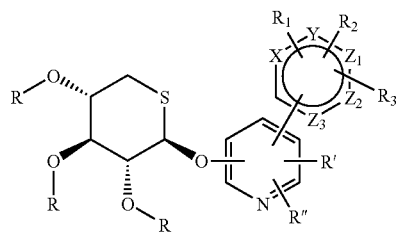

in which:
R, $R_1$, $R_2$, $R_3$, R', R", X, Y, $Z_1$, $Z_2$ and $Z_3$ retain the same meanings as in the starting materials,
are carried out.

For compounds of this type, another similar process consists in reacting a glycosylated pyridineboronic acid or a glycosylated pyridinylboronate of formula:

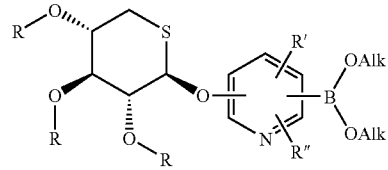

in which R represents a hydrogen atom or a $C_2$-$C_6$ acyl group, R' and R" each independently represent a hydrogen atom, a halogen atom (other than bromine or iodine) or a $C_1$-$C_4$ alkyl group, and Alk represents a hydrogen atom or a $C_1$-$C_4$ alkyl group, with a heteroaryl halide of formula:

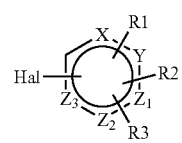

in which Hal represents a halogen, preferably bromine or iodine, and $R_1$, $R_2$ and $R_3$ each independently represent a hydrogen atom, a halogen atom, preferably a fluorine atom, a cyano group, a $C_1$-$C_4$ alkyl group, a $C_1$-$C_4$ alkoxy group or a trifluoromethyl group; or $R_1$ and $R_2$ form, together with the atoms of the heterocycle to which they are attached, an aromatic ring comprising 6 carbon atoms,
under the same conditions as above, in order to obtain the compound of formula:

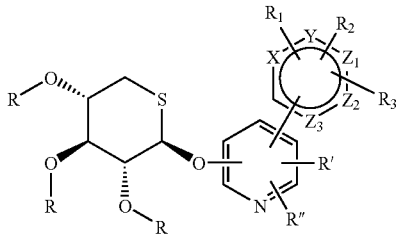

in which:
R, $R_1$, $R_2$, $R_3$, R', R", X, Y, $Z_1$, $Z_2$ and $Z_3$ retain the same meanings as in the starting materials.

Generally, it is preferable to use 2,3,4-tri-O-acetyl-5-thio-α-D-xylopyranosyl bromide or tetra-O-acetyl-5-thio-α-D-xylopyranose when it is a matter of obtaining a β-D-5-thioxylopyranose derivative.

The glycosylation reactions described above generally result in a mixture of the isomers of α and β configuration and it is generally necessary to optimize the operating conditions in order to obtain proportions favorable to the isomer of β configuration. For this same reason, it may also be necessary to carry out purifications, either by recrystallization or by chromatography, in order to obtain the pure β isomer.

The aim of the following examples is to illustrate the invention and they should under no circumstances limit the scope thereof. The melting points were measured on a Kofler bench or in a capillary tube and the Nuclear Magnetic Resonance spectral values are characterized by the chemical shift, calculated with respect to TMS, by the number of protons associated with a signal and by the shape of the signal (s for singlet, d for doublet, t for triplet, q for quartet and m for multiplet). The operating frequency and the solvent used are shown for each compound.

The following abbreviations have been used:
mM means millimole ($10^{-3}$ mol)
DMSO denotes dimethyl sulfoxide
THF denotes tetrahydrofuran
$CHCl_3$ denotes chloroform
DME denotes dimethoxyethane
The "pinacolatoboryl" group means:

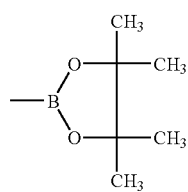

Preparation I 5,6-Dichloro-3-pyridinyl 2,3,4-tri-O-acetyl-5-thio-β-D-xylopyranoside 5.1 g (37.5 mM) of zinc chloride are melted under reduced pressure, the melt is cooled under an inert atmosphere and then 12 ml of toluene, 12 ml of acetonitrile, 3 g of 4 Å molecular sieve and 2.45 g (15 mM) of 5,6-dichloro-3-pyridinol are added. The temperature of the mixture is brought to 90° C. and 3.78 g (37.5 mM) of triethylamine and 5.86 g (16.5 mM) of 2,3,4-tri-O-acetyl-5-thio-α-D-xylopyranosyl bromide are added. The reaction medium is stirred at 90° C. for 20 minutes and is then cooled and filtered to remove the inorganic salts, which are washed with ethyl acetate. The combined organic phases are washed with a 0.5 N sodium hydroxide solution and then the pH is brought to a value of 3 using a 0.1 N hydrochloric acid solution. The organic phase is subsequently washed with a saturated sodium chloride solution, dried over magnesium sulfate and concentrated under reduced pressure. The product is crystallized from ethyl ether and the desired product is obtained in the form of a light brown solid with a yield of 50%.
M.p.=128° C.
$[\alpha]_D^{27}=-92°$ (c=0.23; $CHCl_3$).

Preparation II

4-Bromo-3-pyridinyl 2,3,4-tri-O-acetyl-5-thio-β-D-xylopyranoside

By carrying out the operation analogously to preparation I, starting from 4-bromo-3-pyridinol, the desired product is obtained in the form of a yellow powder (yield=38%).
M.p.=153° C.
$[\alpha]_D^{30}=-69°$ (c=0.31; DMSO).

Preparation III

2-Bromo-3-pyridinyl 2,3,4-tri-O-acetyl-5-thio-β-D-xylopyranoside

By carrying out the operation analogously to preparation I, starting from 2-bromo-3-pyridinol, the desired product is obtained in the form of a white powder (yield=41%).
M.p.=156° C.
$[\alpha]_D^{24}=-78°$ (c=0.40; $CH_3OH$).

Preparation IV

6-Bromo-3-pyridinyl 2,3,4-tri-O-acetyl-5-thio-β-D-xylopyranoside

By carrying out the operation analogously to preparation I, starting from 6-bromo-3-pyridinol, the desired product is obtained in the form of a beige powder (yield=43%).
M.p.=145° C.
$[\alpha]_D^{29}=-20°$ (c=0.52; DMSO).

Preparation V

2-Iodo-6-methyl-3-pyridinyl 2,3,4-tri-O-acetyl-5-thio-β-D-xylopyranoside

By carrying out the operation analogously to preparation I, starting from 2-iodo-6-methyl-3-pyridinol, the desired product is obtained in the form of a white powder (yield=81%).
M.p.=187° C.
$[\alpha]_D^{30}=-88°$ (c=0.28; DMSO).

Preparation VI

2-Chloro-4-methyl-3-pyridinyl 2,3,4-tri-O-acetyl-5-thio-β-D-xylopyranoside

By carrying out the operation analogously to preparation I, starting from 2-chloro-4-methyl-3-pyridinol, the desired product is obtained in the form of a white powder (yield=30%).
M.p.=144° C.
$[\alpha]_D^{30}=+45°$ (c=0.37; DMSO).

Preparation VII

2-Bromo-4-pyridinyl 2,3,4-tri-O-acetyl-5-thio-β-D-xylopyranoside

By carrying out the operation analogously to preparation I, starting from 2-bromo-4-pyridinol, the desired product is obtained in the form of a white solid (yield=37%).
M.p.=162° C. (recrystallized from ether).
$[\alpha]_D^{29}$=−11° (c=0.48; DMSO).

Preparation VIII

5-Bromo-2-fluoro-3-pyridinyl 2,3,4-tri-O-acetyl-5-thio-β-D-xylopyranoside

By carrying out the operation analogously to preparation I, starting from 5-bromo-2-fluoro-3-pyridinol, the desired product is obtained in the form of white crystals (yield=39%).
M.p.=120-122° C. (recrystallized from isopropanol).

Preparation IX

5-Bromo-3-pyridinyl 2,3,4-tri-O-acetyl-5-thio-β-D-xylopyranoside

By carrying out the operation analogously to preparation I, starting from 5-bromo-3-pyridinol, the desired product is obtained in the form of a light brown powder (yield=55%).
M.p.=174° C.
$[\alpha]_D^{20}$=−20° (c=0.23; DMSO).

Preparation X

2-Chloro-6-iodo-3-pyridinyl 2,3,4-tri-O-acetyl-5-thio-β-D-xylopyranoside

By carrying out the operation analogously to preparation I, starting from 2-chloro-6-iodo-3-pyridinol, the desired product is obtained in the form of a white powder (yield=53%).
M.p.=188° C. (recrystallized from ethyl ether).
$[\alpha]_D^{30}$=−34° (c=0.39; DMSO).

Preparation XI

6-Chloro-5-fluoro-3-pyridinyl 2,3,4-tri-O-acetyl-5-thio-β-D-xylopyranoside

By carrying out the operation analogously to preparation I, starting from 6-chloro-5-fluoro-3-pyridinol, the desired product is obtained in the form of white flakes (yield=43%).
M.p.=158-162° C. (recrystallized from ethanol).
$[\alpha]_D^{27}$=−21° (c=0.33; DMSO).

Preparation XII

2-Fluoro-6-iodo-3-pyridinyl 2,3,4-tri-O-acetyl-5-thio-β-D-xylopyranoside

By carrying out the operation analogously to preparation I, starting from 2-fluoro-6-iodo-3-pyridinol, the desired product is obtained in the form of a white powder (yield=41%).
M.p.=234° C. (recrystallized from ethyl ether).
$[\alpha]_D^{30}$=−10° (c=0.49; DMSO).

Preparation XIII

6-Chloro-2-pyridinyl 2,3,4-tri-O-acetyl-5-thio-β-D-xylopyranoside

By carrying out the operation analogously to preparation I, starting from 6-chloro-2-pyridinol, the desired product is obtained in the form of a white powder (yield=20%).
M.p.=127° C.
$[\alpha]_D^{29}$=−72° (c=0.33; CHCl$_3$).

Preparation XIV

5-Bromo-2-chloro-3-pyridinyl 2,3,4-tri-O-acetyl-5-thio-β-D-xylopyranoside

By carrying out the operation analogously to preparation I, starting from 5-bromo-2-chloro-3-pyridinol, the desired product is obtained in the form of beige crystals (yield=38%).
M.p.=143-147° C. (crystallized from ethyl ether).
$[\alpha]_D^{24}$=−35° (c=0.15; DMSO).

Preparation XV

2-Cyano-3-pyridinyl 2,3,4-tri-O-acetyl-5-thio-β-D-xylopyranoside

A solution of 1.7 g (14.17 mM) of 2-cyano-3-pyridinol in 80 ml of acetonitrile is prepared and 4.3 g (18.3 mM) of silver oxide and 3 g of 13× molecular sieve are added with the exclusion of light. The mixture is stirred at 50° C. for 10 min, 6.5 g (18.3 mM) of 2,3,4-tri-O-acetyl-5-thio-β-D-xylopyranosyl bromide are then added and the reaction mixture is maintained at 50° C. for 18 hours with stirring. The mixture is subsequently cooled to ambient temperature and filtered through a filtration aid. The filtrate is diluted with ethyl acetate, washed with water, an N sodium hydroxide solution and then water to neutral pH and finally dried over magnesium sulfate and concentrated under reduced pressure. The residual oil is crystallized by addition of ethyl ether. 0.89 g of the expected product is obtained in the form of beige crystals (yield=16%).
$^1$H NMR (300 MHz; CDCl$_3$) δ: 8.43 (m, 1H), 7.53 (m, 2H), 5.49 (t, 1H), 5.30 (d, 1H), 5.19 (m, 2H), 3.18 (m, 1H), 2.76 (m, 1H), 2.10 (m, 9H).
The product comprises a low proportion of α derivative, the anomeric proton of which gives signals at δ=5.76 and δ=5.63.

EXAMPLE 1

6-(2-Methoxy-3-pyridinyl)-3-pyridinyl 2,3,4-tri-O-acetyl-5-thio-β-D-xylo-pyranoside A solution of 0.354 g (3.34 mM) of sodium carbonate in 3 ml of water, 0.18 g (0.223 mM) of the [1,1'-bis(diphenylphosphino)ferrocene]dichloropalladium(II) complex with dichloromethane and 0.68 g (4.46 mM) of 2-methoxy-3-pyridineboronic acid are added to a solution of 1 g (2.23 mM) of 6-bromo-3-pyridinyl 2,3,4-tri-O-acetyl-5-thio-β-D-xylopyranoside, obtained according to preparation IV, in 10 ml of DME. The reaction mixture is heated using microwave radiation at 120° C. for 20 minutes and cooled, water is added and extraction is carried out with ethyl acetate. The organic phase is washed with a 1M sodium carbonate solution and then with water to neutral pH, dried over magnesium sulfate and concentrated under reduced pressure. The evaporation residue is purified by chromatography on a silica column (eluent: toluene/acetone 90/10; v/v) in order to obtain the expected product in the form of a white solid with a yield of 70%.

M.p.=176° C.
$[\alpha]_D^{29}$=+5° (c=0.30; DMSO).

EXAMPLE 2

6-(2-Methoxy-3-pyridinyl)-3-pyridinyl 5-thio-β-D-xylopyranoside

A solution of 0.3 g (0.63 mM) of 6-(2-methoxy-3-pyridinyl)-3-pyridinyl 2,3,4-tri-O-acetyl-5-thio-β-D-xylopyranoside, obtained according to example 1, in 4 ml of a 7M solution of ammonia in methanol is stirred at ambient temperature for 4 hours. The reaction mixture is subsequently concentrated under reduced pressure and the evaporation residue is crystallized from ether. The desired product is obtained in the form of a white solid with a yield of 81%.

M.p.=127° C.
$[\alpha]_D^{29}$=−45° (c=0.26; DMSO).

EXAMPLE 3

4-Methyl-2-(3-pyridinyl)-3-pyridinyl 2,3,4-tri-O-acetyl-5-thio-β-D-xylo-pyranoside By carrying out the operation analogously to example 1, starting from 2-chloro-4-methyl-3-pyridinyl 2,3,4-tri-O-acetyl-5-thio-β-D-xylopyranoside, obtained according to preparation VI, and 3-pyridineboronic acid, the desired product is obtained in the form of a white foam (yield=27%).

M.p.=143° C.
$[\alpha]_D^{33}$=+29° (c=0.43; DMSO).

EXAMPLE 4

4-Methyl-2-(3-pyridinyl)-3-pyridinyl 5-thio-β-D-xylopyranoside

By carrying out the operation analogously to example 2, starting from the product prepared according to example 3, the desired product is obtained in the form of a white cotton-like product (yield=40%).

M.p.=98° C.
$[\alpha]_D^{29}$=+66° (c=0.20; DMSO).

EXAMPLE 5

2-(3-Furanyl)-6-methyl-3-pyridinyl 2,3,4-tri-O-acetyl-5-thio-β-D-xylopyranoside

By carrying out the operation analogously to example 1, starting from 2-iodo-6-methyl-3-pyridinyl 2,3,4-tri-O-acetyl-5-thio-β-D-xylopyranoside obtained according to preparation V, and 3-furanboronic acid, the desired product is obtained in the form of a white solid (yield=42%).

M.p.=117° C.
$[\alpha]_D^{25}$=−73° (c=0.10; DMSO).

EXAMPLE 6

2-(3-Furanyl)-6-methyl-3-pyridinyl 5-thio-β-D-xylopyranoside

By carrying out the operation analogously to example 2, starting from the product prepared according to example 5, the desired product is obtained in the form of a cream white solid (yield=81%).

M.p.=162° C.
$[\alpha]_D^{29}$=−117° (c=0.10; DMSO).

EXAMPLE 7

2-(5-Methyl-2-furanyl)-3-pyridinyl 2,3,4-tri-O-acetyl-5-thio-β-D-xylo-pyranoside By carrying out the operation analogously to example 1, starting from 2-bromo-3-pyridinyl 2,3,4-tri-O-acetyl-5-thio-β-D-xylopyranoside, obtained according to preparation III, and 5-methyl-2-furanboronic acid, the desired product is obtained in the form of a white solid (yield=45%).

M.p.=128° C.
$[\alpha]_D^{32}$=−68° (c=0.27; DMSO).

EXAMPLE 8

2-(5-Methyl-2-furanyl)-3-pyridinyl 5-thio-β-D-xylopyranoside

By carrying out the operation analogously to example 2, starting from the product prepared according to example 7, the desired product is obtained in the form of a white solid (yield=83%).

M.p.=191° C.
$[\alpha]_D^{30}$=−103° (c=0.28; DMSO).

EXAMPLE 9

2-Chloro-6-(3-pyridinyl)-3-pyridinyl 2,3,4-tri-O-acetyl-5-thio-β-D-xylo-pyranoside By carrying out the operation analogously to example 3, starting from 2-chloro-6-iodo-3-pyridinyl 2,3,4-tri-O-acetyl-5-thio-β-D-xylopyranoside, obtained according to preparation X, the desired product is obtained in the form of a beige powder (yield=34%).

M.p.=155° C.
$[\alpha]_D^{36}$=−38° (c=0.13; DMSO).

EXAMPLE 10

2-Chloro-6-(3-pyridinyl)-3-pyridinyl 5-thio-β-D-xylopyranoside

By carrying out the operation analogously to example 2, starting from the product prepared according to example 9, the desired product is obtained in the form of a beige powder (yield=35%).

M.p.=180° C.
$[\alpha]_D^{35}$=−51° (c=0.11; DMSO).

EXAMPLE 11

2-Fluoro-5-(4-pyridinyl)-3-pyridinyl 2,3,4-tri-O-acetyl-5-thio-β-D-xylopyranoside By carrying out the operation analogously to example 1, starting from 5-bromo-2-fluoro-3-pyridinyl 2,3,4-tri-O-acetyl-5-thio-β-D-xylopyranoside, obtained according to preparation VIII, and 4-pyridineboronic acid, the desired product is obtained in the form of a beige foam (yield=53%).

M.p.=143-144° C.
$[\alpha]_D^{30}$=+8° (c=0.26; DMSO).

EXAMPLE 12

2-Fluoro-5-(4-pyridinyl)-3-pyridinyl 5-thio-β-D-xylopyranoside

By carrying out the operation analogously to example 2, starting from the product prepared according to example 11, the desired product is obtained in the form of a pink foam (yield=59%).

M.p.=98-102° C.

$[\alpha]_D^{30}=-61°$ (c=0.28; DMSO).

EXAMPLE 13

2-Chloro-6-(2-methoxy-3-pyridinyl)-3-pyridinyl 2,3,4-tri-O-acetyl-5-thio-β-D-xylopyranoside By carrying out the operation analogously to example 1, starting from 2-chloro-6-iodo-3-pyridinyl 2,3,4-tri-O-acetyl-5-thio-β-D-xylopyranoside, obtained according to preparation X, and 2-methoxy-3-pyridineboronic acid, the desired product is obtained in the form of a pink solid (yield=40%).

M.p.=221° C.

$[\alpha]_D^{30}=-44°$ (c=0.20; DMSO).

EXAMPLE 14

2-Chloro-6-(2-methoxy-3-pyridinyl)-3-pyridinyl 5-thio-β-D-xylopyranoside

By carrying out the operation analogously to example 2, starting from the product prepared according to example 13, the desired product is obtained in the form of a white cotton-like product (yield=60%).

M.p.=102° C. (recrystallized from a methanol/water mixture).

$[\alpha]_D^{30}=-53°$ (c=0.16; DMSO).

EXAMPLE 15

2-Chloro-6-(2-fluoro-3-pyridinyl)-3-pyridinyl 2,3,4-tri-O-acetyl-5-thio-β-D-xylopyranoside By carrying out the operation analogously to example 1, starting from 2-chloro-6-iodo-3-pyridinyl 2,3,4-tri-O-acetyl-5-thio-β-D-xylopyranoside, obtained according to preparation X, and 2-fluoro-3-pyridineboronic acid, the desired product is obtained in the form of a white powder (yield=27%).

M.p.=227° C. (recrystallized from ethanol).

$[\alpha]_D^{30}=-38°$ (c=0.61; DMSO).

EXAMPLE 16

2-Chloro-6-(2-fluoro-3-pyridinyl)-3-pyridinyl 5-thio-β-D-xylopyranoside

By carrying out the operation analogously to example 2, starting from the product prepared according to example 15, the desired product is obtained in the form of a white cotton-like product (yield=80%).

M.p.=153° C. (recrystallized from an ethanol/water mixture).

$[\alpha]_D^{30}=-28°$ (c=0.48; DMSO).

EXAMPLE 17

2-Chloro-6-(2-fluoro-4-pyridinyl)-3-pyridinyl 2,3,4-tri-O-acetyl-5-thio-β-D-xylopyranoside By carrying out the operation analogously to example 1, starting from 2-chloro-6-iodo-3-pyridinyl 2,3,4-tri-O-acetyl-5-thio-β-D-xylopyranoside, obtained according to preparation X, and 2-fluoro-4-pyridineboronic acid, the desired product is obtained in the form of a white powder (yield=37%).

M.p.=226° C. (recrystallized from a water/acetonitrile mixture).

$[\alpha]_D^{32}=-34°$ (c=0.31; DMSO).

EXAMPLE 18

2-Chloro-6-(2-fluoro-4-pyridinyl)-3-pyridinyl 5-thio-β-D-xylopyranoside

By carrying out the operation analogously to example 2, starting from the product prepared according to example 17, the desired product is obtained in the form of a white powder (yield=27%).

M.p.=195° C. (recrystallized from an isopropanol/water mixture).

$[\alpha]_D^{32}=-41°$ (c=0.18; DMSO).

EXAMPLE 19

2-Chloro-6-(6-fluoro-3-pyridinyl)-3-pyridinyl 2,3,4-tri-O-acetyl-5-thio-β-D-xylopyranoside By carrying out the operation analogously to example 1, starting from 2-chloro-6-iodo-3-pyridinyl 2,3,4-tri-O-acetyl-5-thio-β-D-xylopyranoside, obtained according to preparation X, and 6-fluoro-3-pyridineboronic acid, the desired product is obtained in the form of a white powder (yield=43%).

M.p.=226° C. (recrystallized from a water/acetonitrile mixture).

$[\alpha]_D^{32}=-23°$ (c=0.26; DMSO).

EXAMPLE 20

2-Chloro-6-(6-fluoro-3-pyridinyl)-3-pyridinyl 5-thio-β-D-xylopyranoside

By carrying out the operation analogously to example 2, starting from the product prepared according to example 19, the desired product is obtained in the form of white needles (yield=27%).

M.p.=199° C. (recrystallized from an ethanol/water mixture).

$[\alpha]_D^{32}=-33°$ (c=0.33; DMSO).

EXAMPLE 21

2-Fluoro-6-(4-pyridinyl)-3-pyridinyl 2,3,4-tri-O-acetyl-5-thio-β-D-xylo-pyranoside By carrying out the operation analogously to example 11, starting from 2-fluoro-6-iodo-3-pyridinyl 2,3,4-tri-O-acetyl-5-thio-β-D-xylopyranoside, obtained according to preparation XII, the desired product is obtained in the form of a white cotton-like product (yield=47%).

M.p.=164° C. (recrystallized from a water/acetonitrile mixture).

$[\alpha]_D^{30}=-2°$ (c=0.14; DMSO).

EXAMPLE 22

2-Fluoro-6-(4-pyridinyl)-3-pyridinyl 5-thio-β-D-xylopyranoside

By carrying out the operation analogously to example 2, starting from the product prepared according to example 21, the desired product is obtained in the form of a white powder (yield=34%).

M.p.=196° C. (recrystallized from a methanol/water mixture).

$[\alpha]_D^{30}=-40°$ (c=0.38; DMSO).

EXAMPLE 23

2-Chloro-6-(4-pyridinyl)-3-pyridinyl 2,3,4-tri-O-acetyl-5-thio-β-D-xylo-pyranoside By carrying out the operation analogously to example 11, starting from 2-chloro-6-iodo-3-pyridinyl 2,3,4-tri-O-acetyl-5-thio-β-D-xylopyranoside, obtained according to preparation X, the desired product is obtained in the form of a white solid (yield=13%).

M.p.=179° C. (recrystallized from ethyl ether).

$[\alpha]_D^{30}=-31°$ (c=0.30; DMSO).

EXAMPLE 24

2-Chloro-6-(4-pyridinyl)-3-pyridinyl 5-thio-β-D-xylopyranoside

By carrying out the operation analogously to example 2, starting from the product prepared according to example 23, the desired product is obtained in the form of a yellow powder (yield=47%).

M.p.=186° C. (recrystallized from a methanol/water mixture).

$[\alpha]_D^{30}=-36°$ (c=0.17; DMSO).

EXAMPLE 25

5-(2-Chloro-3-pyridinyl)-3-pyridinyl 2,3,4-tri-O-acetyl-5-thio-β-D-xylo-pyranoside By carrying out the operation analogously to example 1, starting from 5-bromo-3-pyridinyl 2,3,4-tri-O-acetyl-5-thio-β-D-xylopyranoside obtained according to preparation IX, and 2-chloro-3-pyridineboronic acid, the desired product is obtained in the form of a white solid (yield=21%).

M.p.=162° C.

$[\alpha]_D^{29}=-16°$ (c=0.36; DMSO).

EXAMPLE 26

5-(2-Chloro-3-pyridinyl)-3-pyridinyl 5-thio-β-D-xylopyranoside

By carrying out the operation analogously to example 2, starting from the product prepared according to example 25, the desired product is obtained in the form of a white solid (yield=79%).

M.p.=215° C.

$[\alpha]_D^{29}=-47°$ (c=0.35; DMSO).

EXAMPLE 27

5-(6-Methoxy-3-pyridinyl)-3-pyridinyl 2,3,4-tri-O-acetyl-5-thio-β-D-xylo-pyranoside By carrying out the operation analogously to example 1, starting from 5-bromo-3-pyridinyl 2,3,4-tri-O-acetyl-5-thio-β-D-xylopyranoside obtained according to preparation IX and 6-methoxy-3-pyridineboronic acid, the desired product is obtained in the form of a white solid (yield=72%).

M.p.=172° C.

$[\alpha]_D^{29}=-9$ (c=0.24; DMSO).

EXAMPLE 28

5-(6-Methoxy-3-pyridinyl)-3-pyridinyl 5-thio-β-D-xylopyranoside

By carrying out the operation analogously to example 2, starting from the product prepared according to example 27, the desired product is obtained in the form of a white solid (yield=57%).

M.p.=189° C.

$[\alpha]_D^{30}=-47°$ (c=0.34; DMSO).

EXAMPLE 29

5-(6-Chloro-3-pyridinyl)-3-pyridinyl 2,3,4-tri-O-acetyl-5-thio-β-D-xylo-pyranoside By carrying out the operation analogously to example 1, starting from 5-bromo-3-pyridinyl 2,3,4-tri-O-acetyl-5-thio-β-D-xylopyranoside, obtained according to preparation IX, and 6-chloro-3-pyridineboronic acid, the desired product is obtained in the form of a white solid (yield=33%).

M.p.=194° C.

$[\alpha]_D^{29}=-17°$ (c=0.30; DMSO).

EXAMPLE 30

5-(6-Chloro-3-pyridinyl)-3-pyridinyl 5-thio-β-D-xylopyranoside

By carrying out the operation analogously to example 2, starting from the product prepared according to example 29, the desired product is obtained in the form of a white solid (yield=72%).

M.p.=211° C.

$[\alpha]_D^{30}=-46°$ (c=0.45; DMSO).

EXAMPLE 31

5-(2-Methoxy-3-pyridinyl)-3-pyridinyl 2,3,4-tri-O-acetyl-5-thio-β-D-xylo-pyranoside By carrying out the operation analogously to example 1, starting from 5-bromo-3-pyridinyl 2,3,4-ti-O-acetyl-5-thio-β-D-xylopyranoside, obtained according to preparation IX, and 2-methoxy-3-pyridineboronic acid, the desired product is obtained in the form of an ecru solid (yield=63%).

M.p.=167° C.

$[\alpha]_D^{29}=-13°$ (c=0.27; DMSO).

EXAMPLE 32

5-(2-Methoxy-3-pyridinyl)-3-pyridinyl 5-thio-β-D-xylopyranoside

By carrying out the operation analogously to example 2, starting from the product prepared according to example 31, the desired product is obtained in the form of a white solid (yield=77%).

M.p.=209° C.
$[\alpha]_D^{29}=-90°$ (c=0.22; DMSO).

EXAMPLE 33

6-(5-Methyl-2-furanyl)-3-pyridinyl 2,3,4-tri-O-acetyl-5-thio-β-D-xylo-pyranoside By carrying out the operation analogously to example 1, starting from 6-bromo-3-pyridinyl 2,3,4-tri-O-acetyl-5-thio-β-D-xylopyranoside, obtained according to preparation IV, and 5-methyl-2-furanboronic acid, the desired product is obtained in the form of an ecru solid (yield=74%).

M.p.=134° C.
$[\alpha]_D^{29}=+22°$ (c=0.23; DMSO).

EXAMPLE 34

6-(5-Methyl-2-furanyl)-3-pyridinyl 5-thio-β-D-xylopyranoside

By carrying out the operation analogously to example 2, starting from the product prepared according to example 33, the desired product is obtained in the form of a fine ecru solid (yield=71%).

M.p.=168° C.
$[\alpha]_D^{30}=-38°$ (c=0.30; DMSO).

EXAMPLE 35

6-(6-Methyl-3-pyridinyl)-3-pyridinyl 2,3,4-tri-O-acetyl-5-thio-β-D-xylo-pyranoside By carrying out the operation analogously to example 1, starting from 6-bromo-3-pyridinyl 2,3,4-tri-O-acetyl-5-thio-β-D-xylopyranoside, obtained according to preparation IV, and 6-methyl-3-pyridineboronic acid, the desired product is obtained in the form of a white solid (yield=62%).

M.p.=181° C.
$[\alpha]_D^{29}=+15°$ (c=0.21; DMSO).

EXAMPLE 36

6-(6-Methyl-3-pyridinyl)-3-pyridinyl 5-thio-β-D-xylopyranoside

By carrying out the operation analogously to example 2, starting from the product prepared according to example 35, the desired product is obtained in the form of a white powder (yield=48%).

M.p.=228° C.
$[\alpha]_D^{29}=-46°$ (c=0.31; DMSO).

EXAMPLE 37

6-(6-Chloro-3-pyridinyl)-3-pyridinyl 2,3,4-tri-O-acetyl-5-thio-β-D-xylo-pyranoside By carrying out the operation analogously to example 1, starting from 6-bromo-3-pyridinyl 2,3,4-tri-O-acetyl-5-thio-β-D-xylopyranoside, obtained according to preparation IV, and 6-chloro-3-pyridineboronic acid, the desired product is obtained in the form of a white solid (yield=41%).

M.p.=204° C.
$[\alpha]_D^{29}=+5°$ (c=0.22; DMSO).

EXAMPLE 38

6-(6-Chloro-3-pyridinyl)-3-pyridinyl 5-thio-β-D-xylopyranoside

By carrying out the operation analogously to example 2, starting from the product prepared according to example 37, the desired product is obtained in the form of a white solid (yield=62%).

M.p.=170° C. (recrystallized from water).
$[\alpha]_D^{30}=-32°$ (c=0.34; DMSO).

EXAMPLE 39

6-(2-Chloro-3-pyridinyl)-3-pyridinyl 2,3,4-tri-O-acetyl-5-thio-β-D-xylo-pyranoside By carrying out the operation analogously to example 1, starting from 6-bromo-3-pyridinyl 2,3,4-tri-O-acetyl-5-thio-β-D-xylopyranoside, obtained according to preparation IV, and 2-chloro-3-pyridineboronic acid, the desired product is obtained in the form of an ecru solid (yield=43%).

M.p.=180° C.
$[\alpha]_D^{29}=-8°$ (c=0.42; DMSO).

EXAMPLE 40

6-(2-Chloro-3-pyridinyl)-3-pyridinyl 5-thio-β-D-xylopyranoside 0.394 g (0.82 mM) of product obtained according to example 39, 25 ml of methanol and 0.025 ml of an 8% solution of sodium methoxide in methanol are mixed. The mixture is stirred at ambient temperature for 40 minutes and the precipitate obtained is filtered off and dried under reduced pressure at 40° C. The expected product is obtained in the form of an off-white powder with a yield of 93%.

M.p.=203° C.
$[\alpha]_D^{28}=-51°$ (c=0.30; DMSO).

EXAMPLE 41

5-Chloro-6-(4-pyridinyl)-3-pyridinyl 2,3,4-tri-O-acetyl-5-thio-β-D-xylo-pyranoside 0.633 g (1.45 mM) of 5,6-dichloro-3-pyridinyl 2,3,4-tri-O-acetyl-5-thio-β-D-xylopyranoside, obtained according to preparation I, 0.214 g (1.74 mM) of 4-pyridineboronic acid, 0.595 g (3.9 mM) of cesium fluoride and 0.118 g (0.145 mM) of the [1,1'-bis(diphenylphosphino)ferrocene]dichloropalladium(II) complex with dichloromethane are mixed in 6 ml of DME. The mixture is heated at 125° C. for 90 minutes using microwave radiation. The cold mixture is filtered, rinsing is carried out with methanol and the combined organic phases are concentrated under reduced pressure. The evaporation residue is purified by chromatography on a silica column, elution being carried out using a dichloromethane/ethyl acetate mixture (80/20 and 50/50; v/v). The expected product is obtained in the form of a light brown solid with a yield of 20%.

M.p.=153° C.
$[\alpha]_D^{27}=-52°$ (c=0.10; CHCl$_3$).

EXAMPLE 42

5-Chloro-6-(4-pyridinyl)-3-pyridinyl 5-thio-β-D-xylopyranoside 0.315 g (0.656 mM) of product obtained according to example 41, 20 ml of methanol and 0.02 ml of an 8% solution of sodium methoxide in methanol are mixed. The mixture is stirred at ambient temperature for 40 minutes and the precipitate obtained is filtered off and dried under reduced pressure at 50° C. The expected product is obtained in the form of a beige powder with a yield of 82%.

M.p.=226° C.
$[\alpha]_D^{28}=-49°$ (c=0.15; DMSO).

EXAMPLE 43

5-Fluoro-6-(4-pyridinyl)-3-pyridinyl 2,3,4-tri-O-acetyl-5-thio-β-D-xylo-pyranoside By carrying out the operation analogously to example 41, starting from 6-chloro-5-fluoro-3-pyridinyl 2,3,4-tri-O-acetyl-5-thio-β-D-xylopyranoside, obtained according to preparation XI, the desired product is obtained in the form of a white powder (yield=38%).

M.p.=165° C.
$[\alpha]_D^{29}=-28°$ (c=0.23; DMSO).

EXAMPLE 44

5-Fluoro-6-(4-pyridinyl)-3-pyridinyl 5-thio-β-D-xylopyranoside

By carrying out the operation analogously to example 42, starting from the product prepared according to example 43, the desired product is obtained in the form of a gray powder (yield=55%).

M.p.=192° C.
$[\alpha]_D^{29}=-54°$ (c=0.12; DMSO).

EXAMPLE 45

6-(4-Pyridinyl)-2-pyridinyl 2,3,4-tri-O-acetyl-5-thio-β-D-xylopyranoside

By carrying out the operation analogously to example 41, starting from 6-chloro-2-pyridinyl 2,3,4-tri-O-acetyl-5-thio-β-D-xylopyranoside, obtained according to preparation XIII, the desired product is obtained in the form of a cream powder (yield=65%).

M.p.=137° C.
$[\alpha]_D^{28}=-41°$ (c=0.32; CHCl$_3$).

EXAMPLE 46

6-(4-Pyridinyl)-2-pyridinyl 5-thio-β-D-xylopyranoside

By carrying out the operation analogously to example 42, starting from the product prepared according to example 45, the desired product is obtained in the form of a greenish powder (yield=98%).

M.p.=178° C.
$[\alpha]_D^{29}=-23°$ (c=0.28; DMSO).

EXAMPLE 47

6-(3-Pyridinyl)-2-pyridinyl 2,3,4-tri-O-acetyl-5-thio-β-D-xylopyranoside

By carrying out the operation analogously to example 41, starting from 6-chloro-2-pyridinyl 2,3,4-tri-O-acetyl-5-thio-β-D-xylopyranoside, obtained according to preparation XIII, and 3-pyridineboronic acid, the desired product is obtained in the form of a cream powder (yield=38%).

M.p.=141° C.
$[\alpha]_D^{29}=-31°$ (c=0.26; CHCl$_3$).

EXAMPLE 48

6-(3-Pyridinyl)-2-pyridinyl 5-thio-β-D-xylopyranoside

By carrying out the operation analogously to example 42, starting from the product prepared according to example 47, the desired product is obtained in the form of a cream powder (yield=99%).

M.p.=179° C.
$[\alpha]_D^{29}=-44°$ (c=0.22; DMSO).

EXAMPLE 49

5-(5-Fluoro-2-pyridinyl)-3-pyridinyl 2,3,4-tri-O-acetyl-5-thio-β-D-xylo-pyranoside A mixture composed of 2.5 g (5.59 mM) of 5-bromo-3-pyridinyl 2,3,4-tri-O-acetyl-5-thio-β-D-xylopyranoside, obtained according to preparation IX, 9 ml of DME, 0.136 g (0.166 mM) of the [1,1'-bis(diphenylphosphino)ferrocene]dichloropalladium(II) complex with dichloromethane, 2.12 g (8.34 mM) of bis(pinacolato)diborane and 1.64 g (16.7 mM) of potassium acetate is heated at 110° C. for 30 minutes using microwave radiation under an inert atmosphere. After cooling, the reaction medium is filtered and 0.52 g (2.97 mM) of 2-bromo-5-fluoropyridine, 0.24 g (0.29 mM) of the [1,1'-bis(diphenylphosphino)ferrocene]dichloropalladium(II) complex with dichloromethane and 4.45 ml of a 1M aqueous potassium carbonate solution are added to the filtrate. The mixture is again heated at 120° C. for 20 minutes using microwave radiation. The medium is cooled, diluted with water and extracted with ethyl acetate. The organic phase is washed with an aqueous sodium bicarbonate solution and then with water, dried over magnesium sulfate and concentrated under reduced pressure. The evaporation residue is purified by chromatography on a silica column, elution being carried out using a toluene/acetone mixture (80/20; v/v). The product obtained is triturated from ether and filtered off. The desired product is obtained in the form of white crystals with a yield of 71%.

M.p.=164-166° C.
$[\alpha]_D^{22}=-16°$ (c=0.23; DMSO).

EXAMPLE 50

5-(5-Fluoro-2-pyridinyl)-3-pyridinyl 5-thio-β-D-xylopyranoside

By carrying out the operation analogously to example 42, starting from the product prepared according to example 49, the desired product is obtained in the form of white crystals (yield=69%).

M.p.=166-190° C. (recrystallized from water).
$[\alpha]_D^{22}=-85°$ (c=0.59; DMSO).

EXAMPLE 51

2-Fluoro-5-(3-pyridinyl)-3-pyridinyl 2,3,4-tri-O-acetyl-5-thio-β-D-xylo-pyranoside By carrying out the operation analogously to example 49, starting from 5-bromo-2-fluoro-3-pyridinyl 2,3,4-tri-O-acetyl-5-thio-β-D-xylopyranoside, obtained according to preparation VIII and 3-bromopyridine, the desired product is obtained in the form of a gray solid (yield=26%).
M.p.=67-68° C.
$[\alpha]_D^{33}$=−8° (c=1.90; DMSO).

EXAMPLE 52

2-Fluoro-5-(3-pyridinyl)-3-pyridinyl 5-thio-β-D-xylopyranoside

By carrying out the operation analogously to example 2, starting from the product prepared according to example 51, the desired product is obtained in the form of a white solid (yield=86%).
M.p.=215-216° C.
$[\alpha]_D^{33}$=−70° (c=0.62; DMSO).

EXAMPLE 53

5-(3-Methyl-4-pyridinyl)-3-pyridinyl 2,3,4-tri-O-acetyl-5-thio-β-D-xylo-pyranoside By carrying out the operation analogously to example 49, starting from 5-bromo-3-pyridinyl 2,3,4-tri-O-acetyl-5-thio-β-D-xylopyranoside, obtained according to preparation IX, and 4-chloro-3-methylpyridine, the desired product is obtained in the form of beige crystals (yield=15%).
M.p.=153-174° C. (recrystallized from ether).
$[\alpha]_D^{23}$=−2° (c=0.17; DMSO).

EXAMPLE 54

5-(3-Methyl-4-pyridinyl)-3-pyridinyl 5-thio-β-D-xylopyranoside

By carrying out the operation analogously to example 42, starting from the product prepared according to example 53, the desired product is obtained in the form of a beige cotton-like product (yield=50%).
M.p.=194-214° C.
$[\alpha]_D^{23}$=−58° (c=0.20; DMSO).

EXAMPLE 55

5-(3-Methyl-2-pyridinyl)-3-pyridinyl 2,3,4-tri-O-acetyl-5-thio-β-D-xylo-pyranoside By carrying out the operation analogously to example 53, starting from 2-bromo-3-methylpyridine, the desired product is obtained in the form of a white solid (yield=17%).
M.p.=148-150° C. (recrystallized from ether).
$[\alpha]_D^{32}$=−22° (c=0.25; DMSO).

EXAMPLE 56

5-(3-Methyl-2-pyridinyl)-3-pyridinyl 5-thio-β-D-xylopyranoside

By carrying out the operation analogously to example 42, starting from the product prepared according to example 55, the desired product is obtained in the form of a beige solid (yield=67%).
M.p.=162-175° C.
$[\alpha]_D^{32}$=−44° (c=0.32; DMSO).

EXAMPLE 57

5-(2,4-Dimethyl-5-thiazolyl)-3-pyridinyl 2,3,4-tri-O-acetyl-5-thio-β-D-xylo-pyranoside By carrying out the operation analogously to example 53, starting from 5-bromo-2,4-dimethylthiazole, the desired product is obtained and is used directly in the deacetylation stage.

EXAMPLE 58

5-(2,4-Dimethyl-5-thiazolyl)-3-pyridinyl 5-thio-β-D-xylopyranoside

By carrying out the operation analogously to example 42, starting from the product prepared according to example 57, the desired product is obtained in the form of a white solid (yield=32%).
M.p.=150° C.
$[\alpha]_D^{30}$=−61° (c=0.10; DMSO).

EXAMPLE 59

5-[1-Methyl-3-(trifluoromethyl)-1H-pyrazol-4-yl]-3-pyridinyl 2,3,4-tri-O-acetyl-5-thio-β-D-xylopyranoside By carrying out the operation analogously to example 53, starting from 4-bromo-1-methyl-3-(trifluoromethyl)-1H-pyrazole, the desired product is obtained and is used directly in the deacetylation stage.

EXAMPLE 60

5-[1-Methyl-3-(trifluoromethyl)-1H-pyrazol-4-yl]-3-pyridinyl 5-thio-β-D-xylopyranoside By carrying out the operation analogously to example 2, starting from the product prepared according to example 59, the desired product is obtained in the form of a white solid (yield=26%).
M.p.=210° C.
$[\alpha]_D^{29}$=−60° (c=0.24; DMSO).

EXAMPLE 61

5-[5-Methyl-3-(trifluoromethyl)-1H-pyrazol-4-yl]-3-pyridinyl 2,3,4-tri-O-acetyl-5-thio-β-D-xylopyranoside By carrying out the operation analogously to example 53, starting from 4-bromo-5-methyl-3-(trifluoromethyl)-1H-pyrazole, the desired product is obtained and is used directly in the deacetylation stage.

EXAMPLE 62

5-[5-Methyl-3-(trifluoromethyl)-1H-pyrazol-4-yl]-3-pyridinyl 5-thio-β-D-xylopyranoside
By carrying out the operation analogously to example 2, starting from the product prepared according to example 61, the desired product is obtained in the form of a beige solid (yield=6%).
M.p.=234° C.
$[\alpha]_D^{29}$=−76° (c=0.21; DMSO).

EXAMPLE 63

5-(5-Methyl-4-isoxazolyl)-3-pyridinyl 2,3,4-tri-O-acetyl-5-thio-β-D-xylo-pyranoside By carrying out the operation analogously to example 53, starting from 4-iodo-5-methylisoxazole, the desired product is obtained in the form of a white solid (yield=28%).
M.p.=127° C.
$[\alpha]_D^{28}=-28°$ (c=0.22; DMSO).

EXAMPLE 64

5-(5-Methyl-4-isoxazolyl)-3-pyridinyl 5-thio-β-D-xylopyranoside

By carrying out the operation analogously to example 2, starting from the product prepared according to example 63, the desired product is obtained in the form of a white solid (yield=79%).
M.p.=209° C.
$[\alpha]_D^{28}=-87°$ (c=0.19; DMSO).

EXAMPLE 65

5-Pyrazinyl-3-pyridinyl 2,3,4-tri-O-acetyl-5-thio-β-D-xylopyranoside
By carrying out the operation analogously to example 53, starting from iodopyrazine, the desired product is obtained in the form of a white powder (yield=13%).
M.p.=145° C.
$[\alpha]_D^{29}=-11°$ (c=0.22; DMSO).

EXAMPLE 66

5-Pyrazinyl-3-pyridinyl 5-thio-β-D-xylopyranoside
By carrying out the operation analogously to example 2, starting from the product prepared according to example 65, the desired product is obtained in the form of a white solid (yield=70%).
M.p.=197° C.
$[\alpha]_D^{29}=-68°$ (c=0.20; DMSO).

EXAMPLE 67

5-(2-Pyrimidinyl)-3-pyridinyl 2,3,4-tri-O-acetyl-5-thio-β-D-xylopyranoside

By carrying out the operation analogously to example 53, starting from 2-bromopyrimidine, the desired product is obtained and is used directly in the deacetylation stage.

EXAMPLE 68

5-(2-Pyrimidinyl)-3-pyridinyl 5-thio-β-D-xylopyranoside

By carrying out the operation analogously to example 2, starting from the product prepared according to example 67, the desired product is obtained in the form of a white powder (yield=31%).
M.p.=201° C.
$[\alpha]_D^{29}=-69°$ (c=0.23; DMSO).

EXAMPLE 69

5-(2-Thiazolyl)-3-pyridinyl 2,3,4-tri-O-acetyl-5-thio-β-D-xylopyranoside

By carrying out the operation analogously to example 53, starting from 2-bromothiazole, the desired product is obtained and is used directly in the deacetylation stage.

EXAMPLE 70

5-(2-Thiazolyl)-3-pyridinyl 5-thio-β-D-xylopyranoside

By carrying out the operation analogously to example 2, starting from the product prepared according to example 69, the desired product is obtained in the form of a white powder (yield=26%).
M.p.=204° C.
$[\alpha]_D^{29}=-93°$ (c=0.20; DMSO).

EXAMPLE 71

5-[1-Methyl-1H-imidazol-5-yl]-3-pyridinyl 2,3,4-tri-O-acetyl-5-thio-β-D-xylo-pyranoside By carrying out the operation analogously to example 53, starting from 5-bromo-1-methyl-1H-imidazole, the desired product is obtained and is used directly in the deacetylation stage.

EXAMPLE 72

5-[1-Methyl-1H-imidazol-5-yl]-3-pyridinyl 5-thio-β-D-xylopyranoside

By carrying out the operation analogously to example 2, starting from the product prepared according to example 71, the desired product is obtained in the form of a beige powder (yield=25%).
M.p.=213° C.
$[\alpha]_D^{29}=-83°$ (c=0.32; DMSO).

EXAMPLE 73

5-(2-Chloro-4-pyridinyl)-3-pyridinyl 2,3,4-tri-O-acetyl-5-thio-β-D-xylo-pyranoside By carrying out the operation analogously to example 1, starting from 5-bromo-3-pyridinyl 2,3,4-tri-O-acetyl-5-thio-β-D-xylopyranoside, obtained according to preparation IX, and 2-chloro-4-pyridineboronic acid, the desired product is obtained in the form of an ecru solid (yield=55%).
M.p.=105-108° C.
$[\alpha]_D^{30}=-21°$ (c=0.30; DMSO).

EXAMPLE 74

5-(2-Chloro-4-pyridinyl)-3-pyridinyl 5-thio-β-D-xylopyranoside

By carrying out the operation analogously to example 42, starting from the product prepared according to example 73, the desired product is obtained in the form of a white solid (yield=68%).
M.p.=204° C.
$[\alpha]_D^{30}=-76°$ (c=0.34; DMSO).

EXAMPLE 75

5-(3-Chloro-4-pyridinyl)-3-pyridinyl 2,3,4-tri-O-acetyl-5-thio-β-D-xylo-pyranoside By carrying out the operation analogously to example 73, starting from 3-chloro-4-pyridineboronic acid, the desired product is obtained in the form of a white solid (yield=39%).
M.p.=175° C.
$[\alpha]_D^{25}$=−22° (c=0.25; DMSO).

EXAMPLE 76

5-(3-Chloro-4-pyridinyl)-3-pyridinyl 5-thio-β-D-xylopyranoside

By carrying out the operation analogously to example 42, starting from the product prepared according to example 75, the desired product is obtained in the form of a white solid (yield=88%).
M.p.=208° C.
$[\alpha]_D^{25}$=−72° (c=0.24; DMSO).

EXAMPLE 77

6-(6-Methoxy-3-pyridinyl)-3-pyridinyl 2,3,4-tri-O-acetyl-5-thio-β-D-xylo-pyranoside By carrying out the operation analogously to example 1, starting from 6-bromo-3-pyridinyl 2,3,4-tri-O-acetyl-5-thio-β-D-xylopyranoside, obtained according to preparation IV, and 6-methoxy-3-pyridineboronic acid, the desired product is obtained in the form of a white solid (yield=65%).
M.p.=74° C.
$[\alpha]_D^{29}$=+10° (c=0.44; DMSO).

EXAMPLE 78

6-(6-Methoxy-3-pyridinyl)-3-pyridinyl 5-thio-β-D-xylopyranoside

By carrying out the operation analogously to example 42, starting from the product prepared according to example 77, the desired product is obtained in the form of a white solid (yield=30%).
M.p.=167° C.
$[\alpha]_D^{28}$=−27° (c=0.23; DMSO).

EXAMPLE 79

2-(3-Furanyl)-4-methyl-3-pyridinyl 2,3,4-tri-O-acetyl-5-thio-β-D-xylo-pyranoside By carrying out the operation analogously to example 1, starting from 2-chloro-4-methyl-3-pyridinyl 2,3,4-tri-O-acetyl-5-thio-β-D-xylopyranoside obtained according to preparation VI, and 3-furanboronic acid, the desired product is obtained in the form of an ecru solid (yield=77%).
M.p.=164° C.
$[\alpha]_D^{33}$=+61° (c=0.23; DMSO).

EXAMPLE 80

2-(3-Furanyl)-4-methyl-3-pyridinyl 5-thio-β-D-xylopyranoside

By carrying out the operation analogously to example 42, starting from the product prepared according to example 79, the desired product is obtained in the form of a white cotton-like product (yield=59%).
M.p.=95° C.
$[\alpha]_D^{29}$=+83° (c=0.18; DMSO).

EXAMPLE 81

2-(3,5-Dimethyl-4-isoxazolyl)-4-methyl-3-pyridinyl 2,3,4-tri-O-acetyl-5-thio-β-D-xylopyranoside By carrying out the operation analogously to example 79, starting from 3,5-dimethyl-4-isoxazoleboronic acid, the desired product is obtained and is used directly in the deacetylation stage.

EXAMPLE 82

2-(3,5-Dimethyl-4-isoxazolyl)-4-methyl-3-pyridinyl 5-thio-β-D-xylopyranoside

By carrying out the operation analogously to example 42, starting from the product prepared according to example 81, the desired product is obtained in the form of a white powder (yield=20%).
M.p.=70-100° C.
$[\alpha]_D^{25}$=+115° (c=0.10; DMSO).

EXAMPLE 83

4-(3-Pyridinyl)-3-pyridinyl 2,3,4-tri-O-acetyl-5-thio-β-D-xylopyranoside

By carrying out the operation analogously to example 1, starting from 4-bromo-3-pyridinyl 2,3,4-tri-O-acetyl-5-thio-β-D-xylopyranoside, obtained according to preparation II, and 3-pyridineboronic acid, the desired product is obtained in the form of an ecru solid (yield=57%).
M.p.=159° C.
$[\alpha]_D^{32}$=−72° (c=0.25; DMSO).

EXAMPLE 84

4-(3-Pyridinyl)-3-pyridinyl 5-thio-β-D-xylopyranoside

By carrying out the operation analogously to example 42, starting from the product prepared according to example 83, the desired product is obtained in the form of a white solid (yield=86%).
M.p.=212° C.
$[\alpha]_D^{30}$=−53° (c=0.35; DMSO).

EXAMPLE 85

2-(2-Benzofuranyl)-3-pyridinyl 2,3,4-tri-O-acetyl-5-thio-β-D-xylopyranoside

By carrying out the operation analogously to example 1, starting from 2-bromo-3-pyridinyl 2,3,4-tri-O-acetyl-5-thio-β-D-xylopyranoside, obtained according to preparation III, and 2-benzofuranboronic acid, the desired product is obtained and is used directly in the deacetylation stage.

EXAMPLE 86

2-(2-Benzofuranyl)-3-pyridinyl 5-thio-β-D-xylopyranoside

By carrying out the operation analogously to example 42, starting from the product prepared according to example 85, the desired product is obtained in the form of a white solid (yield=15%).
M.p.=215° C.
$[\alpha]_D^{32}$=−68° (c=0.26; DMSO).

EXAMPLE 87

4-(3-Furanyl)-3-pyridinyl 2,3,4-tri-O-acetyl-5-thio-β-D-xylopyranoside

By carrying out the operation analogously to example 83, starting from 3-furanboronic acid, the desired product is obtained in the form of an ecru solid (yield=36%).
M.p.=167° C.
$[\alpha]_D^{31}=-77°$ (c=0.37; DMSO).

EXAMPLE 88

4-(3-Furanyl)-3-pyridinyl 5-thio-β-D-xylopyranoside

By carrying out the operation analogously to example 42, starting from the product prepared according to example 87, the desired product is obtained in the form of a white solid (yield=64%).
M.p.=231° C.
$[\alpha]_D^{32}=-112°$ (c=0.28; DMSO).

EXAMPLE 89

4-(4-Pyridinyl)-3-pyridinyl 2,3,4-tri-O-acetyl-5-thio-β-D-xylopyranoside

By carrying out the operation analogously to example 83, starting from 4-pyridineboronic acid, the desired product is obtained in the form of an ecru solid (yield=55%).
M.p.=185° C.
$[\alpha]_D^{31}=-114°$ (c=0.47; DMSO).

EXAMPLE 90

4-(4-Pyridinyl)-3-pyridinyl 5-thio-β-D-xylopyranoside

By carrying out the operation analogously to example 42, starting from the product prepared according to example 89, the desired product is obtained in the form of a white solid (yield=84%).
M.p.=212° C.
$[\alpha]_D^{32}=-54°$ (c=0.26; DMSO).

EXAMPLE 91

5-(2-Benzothienyl)-3-pyridinyl 2,3,4-tri-O-acetyl-5-thio-β-D-xylopyranoside

By carrying out the operation analogously to example 73, starting from 2-benzothiopheneboronic acid, the desired product is obtained in the form of a beige solid (yield=72%).
M.p.=168° C.
$[\alpha]_D^{30}=+7°$ (c=0.36; DMSO).

EXAMPLE 92

5-(2-Benzothienyl)-3-pyridinyl 5-thio-β-D-xylopyranoside

By carrying out the operation analogously to example 42, starting from the product prepared according to example 91, the desired product is obtained in the form of an ecru solid (yield=91%).
M.p.=235° C.
$[\alpha]_D^{32}=-50°$ (c=0.32; DMSO).

EXAMPLE 93

2-(2-Thienyl)-3-pyridinyl 2,3,4-tri-O-acetyl-5-thio-β-D-xylopyranoside

By carrying out the operation analogously to example 85, starting from 2-thiopheneboronic acid, the desired product is obtained in the form of an ecru solid (yield=51%).
M.p.=166° C.
$[\alpha]_D^{32}=-112°$ (c=0.20; DMSO).

EXAMPLE 94

2-(2-Thienyl)-3-pyridinyl 5-thio-β-D-xylopyranoside

By carrying out the operation analogously to example 42, starting from the product prepared according to example 93, the desired product is obtained in the form of an ecru solid (yield=80%).
M.p.=130° C.
$[\alpha]_D^{30}=-90°$ (c=0.46; DMSO).

EXAMPLE 95

5-(5-Methyl-2-furanyl)-3-pyridinyl 2,3,4-tri-O-acetyl-5-thio-β-D-xylo-pyranoside By carrying out the operation analogously to example 73, starting from 5-methyl-2-furanboronic acid, the desired product is obtained in the form of a beige solid (yield=56%).
M.p.=124° C.
$[\alpha]_D^{30}=+1°$ (c=0.40; DMSO).

EXAMPLE 96

5-(5-Methyl-2-furanyl)-3-pyridinyl 5-thio-β-D-xylopyranoside

By carrying out the operation analogously to example 42, starting from the product prepared according to example 95, the desired product is obtained in the form of a white solid (yield=55%).
M.p.=188° C.
$[\alpha]_D^{30}=-75'$ (c=0.40; DMSO).

EXAMPLE 97

6-(2-Benzofuranyl)-3-pyridinyl 2,3,4-tri-O-acetyl-5-thio-β-D-xylopyranoside

By carrying out the operation analogously to example 1, starting from 6-bromo-3-pyridinyl 2,3,4-tri-O-acetyl-5-thio-β-D-xylopyranoside, obtained according to preparation IV, and 2-benzofuranboronic acid, the desired product is obtained in the form of an ecru solid (yield=65%).
M.p.=179° C.
$[\alpha]_D^{30}=+13°$ (c=0.31; DMSO).

EXAMPLE 98

6-(2-Benzofuranyl)-3-pyridinyl 5-thio-β-D-xylopyranoside

By carrying out the operation analogously to example 42, starting from the product prepared according to example 97, the desired product is obtained in the form of a white solid (yield=50%).
M.p.=195° C.
$[\alpha]_D^{30}=-24°$ (c=0.28; DMSO).

EXAMPLE 99

6-(3-Thienyl)-3-pyridinyl 2,3,4-tri-O-acetyl-5-thio-β-D-xylopyranoside

By carrying out the operation analogously to example 97, starting from 3-thiopheneboronic acid, the desired product is obtained in the form of a white foam (yield=66%).
M.p.=158° C.
$[\alpha]_D^{35}=-9°$ (c=0.30; DMSO).

EXAMPLE 100

6-(3-Thienyl)-3-pyridinyl 5-thio-β-D-xylopyranoside

By carrying out the operation analogously to example 42, starting from the product prepared according to example 99, the desired product is obtained in the form of an off-white solid (yield=98%).
M.p.=154° C.
$[\alpha]_D^{30}=-50°$ (c=0.28; DMSO).

EXAMPLE 101

2-(2-Furanyl)-3-pyridinyl 2,3,4-tri-O-acetyl-5-thio-β-D-xylopyranoside

By carrying out the operation analogously to example 85, starting from 2-furanboronic acid, the desired product is obtained in the form of an ecru solid (yield=46%).
M.p.=160° C.
$[\alpha]_D^{28}=-60°$ (c=0.51; DMSO).

EXAMPLE 102

2-(2-Furanyl)-3-pyridinyl 5-thio-β-D-xylopyranoside

By carrying out the operation analogously to example 42, starting from the product prepared according to example 101, the desired product is obtained in the form of an ecru solid (yield=91%).
M.p.=184° C.
$[\alpha]_D^{34}=-108°$ (c=0.30; DMSO).

EXAMPLE 103

6-(2-Furanyl)-3-pyridinyl 2,3,4-tri-O-acetyl-5-thio-β-D-xylopyranoside

By carrying out the operation analogously to example 97, starting from 2-furanboronic acid, the desired product is obtained in the form of an off-white solid (yield=64%).
M.p.=133° C.
$[\alpha]^{30}=+16°$ (c=0.30; DMSO).

EXAMPLE 104

6-(2-Furanyl)-3-pyridinyl 5-thio-β-D-xylopyranoside

By carrying out the operation analogously to example 42, starting from the product prepared according to example 103, the desired product is obtained in the form of a pale pink solid (yield=92%).
M.p.=146° C.
$[\alpha]_D^{30}=-53°$ (c=0.30; DMSO).

EXAMPLE 105

2-(4-Pyridinyl)-3-pyridinyl 2,3,4-tri-O-acetyl-5-thio-β-D-xylopyranoside

By carrying out the operation analogously to example 85, starting from 4-pyridineboronic acid, the desired product is obtained in the form of an ecru solid (yield=28%).
M.p.=161° C.
$[\alpha]_D^{28}=-82°$ (c=0.30; DMSO).

EXAMPLE 106

2-(4-Pyridinyl)-3-pyridinyl 5-thio-β-D-xylopyranoside

By carrying out the operation analogously to example 42, starting from the product prepared according to example 105, the desired product is obtained in the form of a beige solid (yield=97%).
M.p.=129° C.
$[\alpha]_D^{30}=-56°$ (c=0.40; DMSO).

EXAMPLE 107

6-(2-Thienyl)-3-pyridinyl 2,3,4-tri-O-acetyl-5-thio-β-D-xylopyranoside

By carrying out the operation analogously to example 97, starting from 2-thiopheneboronic acid, the desired product is obtained in the form of an ecru solid (yield=68%).
M.p.=172° C.
$[\alpha]_D^{33}=-6°$ (c=0.40; DMSO).

EXAMPLE 108

6-(2-Thienyl)-3-pyridinyl 5-thio-β-D-xylopyranoside

By carrying out the operation analogously to example 42, starting from the product prepared according to example 107, the desired product is obtained in the form of a beige solid (yield=80%).
M.p.=134° C.
$[\alpha]_D^{30}=-40°$ (c=0.38; DMSO).

EXAMPLE 109

5-(2-Furanyl)-3-pyridinyl 2,3,4-tri-O-acetyl-5-thio-β-D-xylopyranoside

By carrying out the operation analogously to example 73, starting from 2-furanboronic acid, the desired product is obtained in the form of a beige foam (yield=61%).
M.p.=184° C.
$[\alpha]_D^{25}=-10°$ (c=0.28; DMSO).

EXAMPLE 110

5-(2-Furanyl)-3-pyridinyl 5-thio-β-D-xylopyranoside

By carrying out the operation analogously to example 42, starting from the product prepared according to example 109, the desired product is obtained in the form of a beige solid (yield=66%).
M.p.=215° C.
$[\alpha]_D^{30}=-68°$ (c=0.25; DMSO).

EXAMPLE 111

2-(3-Pyridinyl)-3-pyridinyl 2,3,4-tri-O-acetyl-5-thio-β-D-xylopyranoside

By carrying out the operation analogously to example 85, starting from 3-pyridineboronic acid, the desired product is obtained in the form of an ocher solid (yield=28%).
M.p.=70° C.
$[\alpha]_D^{24} = -70°$ (c=0.35; DMSO).

EXAMPLE 112

2-(3-Pyridinyl)-3-pyridinyl 5-thio-β-D-xylopyranoside

By carrying out the operation analogously to example 42, starting from the product prepared according to example 111, the desired product is obtained in the form of an ocher solid (yield=89%).
M.p.=80° C.
$[\alpha]_D^{30} = -40°$ (c=0.44; DMSO).

EXAMPLE 113

2-(3-Furanyl)-3-pyridinyl 2,3,4-tri-O-acetyl-5-thio-β-D-xylopyranoside

By carrying out the operation analogously to example 85, starting from 3-furanboronic acid, the desired product is obtained in the form of a white solid (yield=20%).
M.p.=185° C.
$[\alpha]_D^{25} = -99°$ (c=0.28; DMSO).

EXAMPLE 114

2-(3-Furanyl)-3-pyridinyl 5-thio-β-D-xylopyranoside

By carrying out the operation analogously to example 42, starting from the product prepared according to example 113, the desired product is obtained in the form of a white solid (yield=91%).
M.p.=128° C.
$[\alpha]_D^{24} = -74°$ (c=0.30; DMSO).

EXAMPLE 115

5-(2-Benzofuranyl)-3-pyridinyl 2,3,4-tri-O-acetyl-5-thio-β-D-xylopyranoside

By carrying out the operation analogously to example 73, starting from 2-benzofuranboronic acid, the desired product is obtained in the form of an ecru solid (yield=70%).
M.p.=125° C.
$[\alpha]_D^{29} = +8°$ (c=0.40; DMSO).

EXAMPLE 116

5-(2-Benzofuranyl)-3-pyridinyl 5-thio-β-D-xylopyranoside

By carrying out the operation analogously to example 42, starting from the product prepared according to example 115, the desired product is obtained in the form of a white solid (yield=86%).
M.p.=210° C.
$[\alpha]_D^{24} = -44°$ (c=0.30; DMSO).

EXAMPLE 117

6-(3-Furanyl)-3-pyridinyl 2,3,4-tri-O-acetyl-5-thio-β-D-xylopyranoside

By carrying out the operation analogously to example 97, starting from 3-furanboronic acid, the desired product is obtained in the form of an ecru solid (yield=66%).
M.p.=187° C.
$[\alpha]_D^{29} = +3°$ (c=0.25; DMSO).

EXAMPLE 118

6-(3-Furanyl)-3-pyridinyl 5-thio-β-D-xylopyranoside

By carrying out the operation analogously to example 42, starting from the product prepared according to example 117, the desired product is obtained in the form of an ecru solid (yield=85%).
M.p.=132° C.
$[\alpha]_D^{29} = -29°$ (c=0.27; DMSO).

EXAMPLE 119

6-(3-Pyridinyl)-3-pyridinyl 2,3,4-tri-O-acetyl-5-thio-β-D-xylopyranoside

By carrying out the operation analogously to example 97, starting from 3-pyridineboronic acid, the desired product is obtained in the form of an ecru solid (yield=50%).
M.p.=196° C.
$[\alpha]_D^{26} = +4°$ (c=0.27; DMSO).

EXAMPLE 120

6-(3-Pyridinyl)-3-pyridinyl 5-thio-β-D-xylopyranoside

By carrying out the operation analogously to example 42, starting from the product prepared according to example 119, the desired product is obtained in the form of a pale pink solid (yield=99%).
M.p.=152° C.
$[\alpha]_D^{28} = -40°$ (c=0.30; DMSO).

EXAMPLE 121

6-(4-Pyridinyl)-3-pyridinyl 2,3,4-tri-O-acetyl-5-thio-β-D-xylopyranoside

By carrying out the operation analogously to example 97, starting from 4-pyridineboronic acid, the desired product is obtained in the form of an off-white solid (yield=31%).
M.p.=189° C.
$[\alpha]_D^{29} = +4°$ (c=0.40; DMSO).

EXAMPLE 122

6-(4-Pyridinyl)-3-pyridinyl 5-thio-β-D-xylopyranoside

By carrying out the operation analogously to example 42, starting from the product prepared according to example 121, the desired product is obtained in the form of an ecru solid (yield=82%).
M.p.=248° C.
$[\alpha]_D^{26} = -35°$ (c=0.34; DMSO).

EXAMPLE 123

5-(4-Pyridinyl)-3-pyridinyl 2,3,4-tri-O-acetyl-5-thio-β-D-xylopyranoside

By carrying out the operation analogously to example 73, starting from 4-pyridineboronic acid, the desired product is obtained in the form of an off-white solid (yield=40%).
M.p.=138° C.
$[\alpha]_D^{27}=-14°$ (c=0.35; DMSO).

EXAMPLE 124

5-(4-Pyridinyl)-3-pyridinyl 5-thio-β-D-xylopyranoside 0.41 g (0.92 mM) of product obtained according to example 123 is added to a mixture of 6 ml of THF and 6 ml of water. The medium is cooled using an ice bath, 0.385 g (9.18 mM) of lithium hydroxide (monohydrate) is added and the mixture is stirred for 90 minutes. The reaction medium is partially concentrated under reduced pressure and the resulting aqueous phase is brought to pH 5-6 using a 1N hydrochloric acid solution. The precipitated product is filtered off and dried. The desired product is thus obtained in the form of a white solid with a yield of 88%.
M.p.=213° C.
$[\alpha]_D^{27}=-48°$ (c=0.40; DMSO).

EXAMPLE 125

5-(3-Furanyl)-3-pyridinyl 2,3,4-tri-O-acetyl-5-thio-β-D-xylopyranoside

By carrying out the operation analogously to example 73, starting from 3-furanboronic acid, the desired product is obtained in the form of a beige solid (yield=32%).
M.p.=127° C.
$[\alpha]_D^{27}=-20°$ (c=0.29; DMSO).

EXAMPLE 126

5-(3-Furanyl)-3-pyridinyl 5-thio-β-D-xylopyranoside

By carrying out the operation analogously to example 42, starting from the product prepared according to example 125, the desired product is obtained in the form of an ecru solid (yield=93%).
M.p.=170° C.
$[\alpha]_D^{27}=-72°$ (c=0.31; DMSO).

EXAMPLE 127

5-(3-Pyridinyl)-3-pyridinyl 2,3,4-tri-O-acetyl-5-thio-β-D-xylopyranoside

By carrying out the operation analogously to example 73, starting from 3-pyridineboronic acid, the desired product is obtained in the form of an ecru solid (yield=63%).
M.p.=149° C.
$[\alpha]_D^{23}=-23°$ (c=0.25; DMSO).

EXAMPLE 128

5-(3-Pyridinyl)-3-pyridinyl 5-thio-β-D-xylopyranoside

By carrying out the operation analogously to example 42, starting from the product prepared according to example 127, the desired product is obtained in the form of an ecru solid (yield=50%).
M.p.=203° C.
$[\alpha]_D^{23}=-8°$ (c=0.43; DMSO).

EXAMPLE 129

2-(4-Pyridinyl)-4-pyridinyl 2,3,4-tri-O-acetyl-5-thio-β-D-xylopyranoside

By carrying out the operation analogously to example 1, starting from 2-bromo-4-pyridinyl 2,3,4-tri-O-acetyl-5-thio-β-D-xylopyranoside, obtained according to preparation VII, and 4-pyridineboronic acid, the desired product is obtained in the form of a white solid (yield=53%).
M.p.=185° C.
$[\alpha]_D^{29}=-27°$ (c=0.13; DMSO).

EXAMPLE 130

2-(4-Pyridinyl)-4-pyridinyl 5-thio-β-D-xylopyranoside

By carrying out the operation analogously to example 2, starting from the product prepared according to example 129, the desired product is obtained in the form of a white solid (yield=42%).
M.p.=170° C.
$[\alpha]_D^{29}=-49°$ (c=0.10; DMSO).

EXAMPLE 131

2-(6-Fluoro-3-pyridinyl)-4-pyridinyl 2,3,4-tri-O-acetyl-5-thio-β-D-xylopyranoside By carrying out the operation analogously to example 129, starting from 6-fluoro-3-pyridineboronic acid, the desired product is obtained in the form of a white solid (yield=51%).
M.p.=151° C.
$[\alpha]_D^{29}=-34°$ (c=0.15; DMSO).

EXAMPLE 132

2-(6-Fluoro-3-pyridinyl)-4-pyridinyl 5-thio-β-D-xylopyranoside

By carrying out the operation analogously to example 2, starting from the product prepared according to example 131, the desired product is obtained in the form of a white solid (yield=94%).
M.p.=171° C.
$[\alpha]_D^{29}=-66°$ (c=0.26; DMSO).

EXAMPLE 133

2-(3-Pyridinyl)-4-pyridinyl 2,3,4-tri-O-acetyl-5-thio-β-D-xylopyranoside

By carrying out the operation analogously to example 129, starting from 3-pyridineboronic acid, the desired product is obtained in the form of beige crystals (yield=22%).
M.p.=185° C. (recrystallized from isopropanol).
$[\alpha]_D^{31}=-21°$ (c=0.24; DMSO).

EXAMPLE 134

2-(3-Pyridinyl)-4-pyridinyl 5-thio-β-D-xylopyranoside

By carrying out the operation analogously to example 2, starting from the product prepared according to example 133, the desired product is obtained in the form of white crystals (yield=66%).
M.p.=197° C. (recrystallized from water).
$[\alpha]_D^{29}$=−83° (c=0.10; DMSO).

EXAMPLE 135

5-(2-Thienyl)-3-pyridinyl 2,3,4-tri-O-acetyl-5-thio-β-D-xylopyranoside

By carrying out the operation analogously to example 73, starting from 2-thiopheneboronic acid, the desired product is obtained in the form of an ecru solid (yield=57%).
M.p.=166° C.
$[\alpha]_D^{27}$=+6° (c=0.25; DMSO).

EXAMPLE 136

5-(2-Thienyl)-3-pyridinyl 5-thio-β-D-xylopyranoside

By carrying out the operation analogously to example 42, starting from the product prepared according to example 135, the desired product is obtained in the form of an ecru solid (yield=78%).
M.p.=205° C.
$[\alpha]_D^{30}$=−68° (c=0.40; DMSO).

EXAMPLE 137

5-(5-Methoxy-3-pyridinyl)-3-pyridinyl 2,3,4-tri-O-acetyl-5-thio-β-D-xylo-pyranoside A mixture composed of 1 g (5.32 mM) of 3-bromo-5-methoxypyridine, 10 ml of DME, 2.02 g (7.98 mM) of bis(pinacolato)diborane, 0.13 g (0.16 mM) of the [1,1'-bis(diphenylphosphino)ferrocene]dichloropalladium(II) complex with dichloromethane and 1.56 g (15.96 mM) of potassium acetate is heated at 110° C. for 30 minutes using microwave radiation under an argon atmosphere. The mixture is cooled and filtered, and 1.59 g (3.55 mM) of 5-bromo-3-pyridinyl 2,3,4-tri-O-acetyl-5-thio-β-D-xylopyranoside, obtained according to preparation IX, 0.29 g (0.355 mM) of the [1,1'-bis(diphenylphosphino)ferrocene]dichloropalladium(II) complex with dichloromethane and 0.564 g (5.32 mM) of sodium carbonate dissolved in 5 ml of water are added to the filtrate. The reaction mixture is heated at 120° C. for 20 minutes using microwave radiation. The medium is subsequently cooled, water is added and extraction is carried out with ethyl acetate. The organic phase is washed with an aqueous sodium bicarbonate solution and with water, then dried over sodium sulfate and concentrated under reduced pressure. The evaporation residue is purified by chromatography on a silica column (eluent: toluene/isopropanol 90/10; v/v) and the product obtained is triturated in the presence of ether and filtered off. The expected product is obtained in the form of a white solid with a yield of 28%.
M.p.=181° C.
$[\alpha]_D^{28}$=−7° (c=0.26; DMSO).

EXAMPLE 138

5-(5-Methoxy-3-pyridinyl)-3-pyridinyl 5-thio-β-D-xylopyranoside

By carrying out the operation analogously to example 42, starting from the product prepared according to example 137, the desired product is obtained in the form of a white solid (yield=33%).
M.p.=193° C.
$[\alpha]_D^{27}$=−71° (c=0.40; DMSO).

EXAMPLE 139

6-(5-Methyl-4-isoxazolyl)-3-pyridinyl 2,3,4-tri-O-acetyl-5-thio-β-D-xylo-pyranoside A solution of 0.208 g (1 mM) of 4-iodo-5-methylisoxazole in 5 ml of THF is prepared under an argon atmosphere and 0.019 g (0.1 mM) of cuprous iodide and 0.060 g (1.5 mM) of 60% sodium hydride in oil are added. The reaction mixture is stirred at ambient temperature for 5 minutes and 0.192 g (1.5 mM) of bis(pinacolato)diborane is added. The reaction mixture is subsequently stirred at ambient temperature for 1 hour, then 4 ml of a saturated sodium bicarbonate solution are added and extraction is carried out with ethyl acetate. The organic phase is washed with water, dried over sodium sulfate and concentrated under reduced pressure. The pinacol ester of 5-methyl-4-isoxazoleboronic acid [$^1$H NMR (250 MHz; $d_6$-DMSO) δ=8.44 (s, 1H), 2.55 (s, 3H), 12.27 (s, 12H)] is obtained in the form of a white solid with a yield of 81%. This compound is again reacted with 6-bromo-3-pyridinyl 2,3,4-tri-O-acetyl-5-thio-β-D-xylopyranoside, obtained according to preparation IV, analogously to the process employed for example 1 and the expected compound is thus obtained in the form of a white solid (yield=43%)
M.p.=165° C.
$[\alpha]_D^{30}$=−4° (c=0.31; DMSO).

EXAMPLE 140

6-(5-Methyl-4-isoxazolyl)-3-pyridinyl 5-thio-β-D-xylopyranoside

By carrying out the operation analogously to example 2, starting from the product prepared according to example 139, the desired product is obtained in the form of a white solid (yield=39%).
M.p.=184° C.
$[\alpha]_D^{30}$=−69° (c=0.25; DMSO).

EXAMPLE 141

6-(5-Methyl-3-pyridinyl)-3-pyridinyl 2,3,4-tri-O-acetyl-5-thio-β-D-xylo-pyranoside By carrying out the operation analogously to example 137, starting from 3-bromo-5-methylpyridine and 6-bromo-3-pyridinyl 2,3,4-tri-O-acetyl-5-thio-β-D-xylopyranoside, obtained according to preparation IV, the desired product is obtained in the form of a white solid (yield=38%).
M.p.=189-190° C.
$[\alpha]_D^{25}$=+9° (c=0.20; DMSO).

EXAMPLE 142

6-(5-Methyl-3-pyridinyl)-3-pyridinyl 5-thio-β-D-xylopyranoside

By carrying out the operation analogously to example 42, starting from the product prepared according to example 141, the desired product is obtained in the form of a white solid (yield=49%).
M.p.=165-166° C.
$[\alpha]_D^{30}$=−44° (c=0.25; DMSO).

EXAMPLE 143

5-(5-Methyl-3-pyridinyl)-3-pyridinyl 2,3,4-tri-O-acetyl-5-thio-β-D-xylo-pyranoside By carrying out the operation analogously to example 137, starting from 3-bromo-5-methylpyridine, the desired product is obtained in the form of a beige solid (yield=45%).
M.p.=180-182° C.
$[\alpha]_D^{25}$=−17° (c=0.24; DMSO).

EXAMPLE 144

5-(5-Methyl-3-pyridinyl)-3-pyridinyl 5-thio-β-D-xylopyranoside

By carrying out the operation analogously to example 42, starting from the product prepared according to example 143, the desired product is obtained in the form of a white solid (yield=83%).
M.p.=119-120° C.
$[\alpha]_D^{25}$=−73° (c=0.27; DMSO).

EXAMPLE 145

5-(5-Chloro-3-pyridinyl)-3-pyridinyl 2,3,4-tri-O-acetyl-5-thio-β-D-xylo-pyranoside By carrying out the operation analogously to example 1, starting from 5-bromo-3-pyridinyl 2,3,4-tri-O-acetyl-5-thio-β-D-xylopyranoside, obtained according to preparation IX, and 3-chloro-5-(pinacolatoboryl)pyridine, the desired product is obtained in the form of a white solid (yield=31%).
M.p.=199° C.
$[\alpha]_D^{29}$=−23° (c=0.29; DMSO).

EXAMPLE 146

5-(5-Chloro-3-pyridinyl)-3-pyridinyl 5-thio-β-D-xylopyranoside

By carrying out the operation analogously to example 42, starting from the product prepared according to example 145, the desired product is obtained in the form of a white solid (yield=73%).
M.p.=185-187° C.
$[\alpha]_D^{29}$=−23° (c=0.27; DMSO).

EXAMPLE 147

5-(6-Cyano-3-pyridinyl)-3-pyridinyl 2,3,4-tri-O-acetyl-5-thio-β-D-xylo-pyranoside By carrying out the operation analogously to example 1, starting from 5-bromo-3-pyridinyl 2,3,4-tri-O-acetyl-5-thio-β-D-xylopyranoside, obtained according to preparation IX, and 6-cyano-3-(pinacolatoboryl)pyridine, the desired product is obtained in the form of a mauve solid (yield=22%).
M.p.=142-151° C.
$[\alpha]_D^{29}$=−14° (c=0.26; DMSO).

EXAMPLE 148

5-(6-Cyano-3-pyridinyl)-3-pyridinyl 5-thio-β-D-xylopyranoside

By carrying out the operation analogously to example 2, starting from the product prepared according to example 147, the desired product is obtained in the form of a white solid (yield=30%).
M.p.=197-203° C.
$[\alpha]_D^{29}$=−68° (c=0.34; DMSO).

EXAMPLE 149

6-(5-Fluoro-3-pyridinyl)-3-pyridinyl 2,3,4-tri-O-acetyl-5-thio-β-D-xylo-pyranoside By carrying out the operation analogously to example 1, starting from 6-bromo-3-pyridinyl 2,3,4-tri-O-acetyl-5-thio-β-D-xylopyranoside, obtained according to preparation IV, and 3-fluoro-5-(pinacolatoboryl)pyridine, the desired product is obtained in the form of a white solid (yield=22%).
M.p.=197-198° C.
$[\alpha]_D^{29}$=+1° (c=0.22; DMSO).

EXAMPLE 150

6-(5-Fluoro-3-pyridinyl)-3-pyridinyl 5-thio-β-D-xylopyranoside

By carrying out the operation analogously to example 2, starting from the product prepared according to example 149, the desired product is obtained in the form of a white solid (yield=66%).
M.p.=207-217° C.
$[\alpha]_D^{29}$=−56° (c=0.21; DMSO).

EXAMPLE 151

5-(2-Methyl-3-pyridinyl)-3-pyridinyl 2,3,4-tri-O-acetyl-5-thio-β-D-xylo-pyranoside By carrying out the operation analogously to example 137, starting from 5-bromo-3-pyridinyl 2,3,4-tri-O-acetyl-5-thio-β-D-xylopyranoside, obtained according to preparation IX, and 2-methyl-3-(pinacolatoboryl)pyridine (obtained from 2-methyl-3-pyridinyl trifluoromethanesulfonate), the desired product is obtained in the form of a beige solid (yield=30%).
M.p.=152-153° C.
$[\alpha]_D^{29}$=−21° (c=0.24; DMSO).

EXAMPLE 152

5-(2-Methyl-3-pyridinyl)-3-pyridinyl 5-thio-β-D-xylopyranoside

By carrying out the operation analogously to example 42, starting from the product prepared according to example 151, the desired product is obtained in the form of a white solid (yield=85%).
M.p.=204-207° C.
$[\alpha]_D^{29}$=−81° (c=0.21; DMSO).

EXAMPLE 153

5-(5-Fluoro-3-pyridinyl)-3-pyridinyl 2,3,4-tri-O-acetyl-5-thio-β-D-xylo-pyranoside By carrying out the operation analogously to example 1, starting from 5-bromo-3-pyridinyl 2,3,4-tri-O-acetyl-5-thio-β-D-xylopyranoside and 3-fluoro-5-(pinacolatoboryl)pyridine, the desired product is obtained in the form of a white solid (yield=26%).
M.p.=175-176° C.
$[\alpha]_D^{29}$=−21° (c=0.30; DMSO).

EXAMPLE 154

5-(5-Fluoro-3-pyridinyl)-3-pyridinyl 5-thio-β-D-xylopyranoside

By carrying out the operation analogously to example 42, starting from the product prepared according to example 153, the desired product is obtained in the form of a white solid (yield=77%).
M.p.=160-171° C.
$[\alpha]_D^{29}$=−72° (c=0.25; DMSO).

EXAMPLE 155

6-(5-Methoxy-3-pyridinyl)-3-pyridinyl 2,3,4-tri-O-acetyl-5-thio-β-D-xylo-pyranoside By carrying out the operation analogously to example 137, starting from 3-bromo-5-methoxypyridine and 6-bromo-3-pyridinyl 2,3,4-tri-O-acetyl-5-thio-β-D-xylopyranoside, obtained according to preparation IV, the desired product is obtained in the form of a white solid (yield=48%).
M.p.=155° C.
$[\alpha]_D^{29}$=+1° (c=0.47; DMSO).

EXAMPLE 156

6-(5-Methoxy-3-pyridinyl)-3-pyridinyl 5-thio-β-D-xylopyranoside

By carrying out the operation analogously to example 2, starting from the product prepared according to example 155, the desired product is obtained in the form of a white solid (yield=93%).
M.p.=193° C.
$[\alpha]_D^{28}$=−31° (c=0.42; DMSO).

EXAMPLE 157

5-(1,3,5-Trimethyl-1H-pyrazol-4-yl)-3-pyridinyl 2,3,4-tri-O-acetyl-5-thio-β-D-xylopyranoside By carrying out the operation analogously to example 1, starting from 5-bromo-3-pyridinyl 2,3,4-tri-O-acetyl-5-thio-β-D-xylopyranoside, obtained according to preparation IX, and 1,3,5-trimethyl-4-(pinacolatoboryl)pyrazole, the desired product is obtained in the form of a white solid (yield=60%).
M.p.=166° C.
$[\alpha]_D^{29}$=−26° (c=0.19; DMSO).

EXAMPLE 158

5-(1,3,5-Trimethyl-1H-pyrazol-4-yl)-3-pyridinyl 5-thio-β-D-xylopyranoside

By carrying out the operation analogously to example 2, starting from the product prepared according to example 157, the desired product is obtained in the form of a white powder (yield=48%).
M.p.=174° C.
$[\alpha]_D^{29}$=−82° (c=0.27; DMSO).

EXAMPLE 159

5-(3,5-Dimethyl-1H-pyrazol-4-yl)-3-pyridinyl 2,3,4-tri-O-acetyl-5-thio-β-D-xylopyranoside By carrying out the operation analogously to example 1, starting from 5-bromo-3-pyridinyl 2,3,4-tri-O-acetyl-5-thio-β-D-xylopyranoside, obtained according to preparation IX, and 3,5-dimethyl-4-(pinacolatoboryl)pyrazole, the desired product is obtained in the form of a beige solid (yield=45%).
M.p.=95° C. (crystallized from ether).
$[\alpha]_D^{29}$=−22° (c=0.24; DMSO).

EXAMPLE 160

5-(3,5-Dimethyl-1H-pyrazol-4-yl)-3-pyridinyl 5-thio-β-D-xylopyranoside

By carrying out the operation analogously to example 2, starting from the product prepared according to example 159, the desired product is obtained in the form of a white powder (yield=41%).
M.p.=227° C.
$[\alpha]_D^{28}$=−86° (c=0.28; DMSO).

EXAMPLE 161

6-(6-Cyano-3-pyridinyl)-3-pyridinyl 2,3,4-tri-O-acetyl-5-thio-β-D-xylo-pyranoside By carrying out the operation analogously to example 1, starting from 6-bromo-3-pyridinyl 2,3,4-tri-O-acetyl-5-thio-β-D-xylopyranoside, obtained according to preparation IV, and 6-cyano-3-(pinacolatoboryl)pyridine, the desired product is obtained in the form of a white solid (yield=41%).
M.p.=247° C.
$[\alpha]_D^{29}$=+15° (c=0.20; DMSO).

EXAMPLE 162

6-(6-Cyano-3-pyridinyl)-3-pyridinyl 5-thio-β-D-xylopyranoside

By carrying out the operation analogously to example 2, starting from the product prepared according to example 161, the desired product is obtained in the form of a white solid (yield=49%).
M.p.=167° C.
$[\alpha]_D^{27}$=−43° (c=0.30; DMSO).

EXAMPLE 163

6-(1,3,5-Trimethyl-1H-pyrazol-4-yl)-3-pyridinyl 2,3,4-tri-O-acetyl-5-thio-β-D-xylopyranoside By carrying out the operation analogously to example 1, starting from 6-bromo-3-pyridinyl 2,3,4-tri-O-acetyl-5-thio-β-D-xylopyranoside, obtained according to preparation IV, and 1,3,5-trimethyl-4-(pinacolatoboryl)-1H-pyrazole, the desired product is obtained in the form of a white solid (yield=54%).
M.p.=156° C.
$[\alpha]_D^{28}$=0° (c=0.24; DMSO).

EXAMPLE 164

6-(1,3,5-Trimethyl-1H-pyrazol-4-yl)-3-pyridinyl 5-thio-β-D-xylopyranoside

By carrying out the operation analogously to example 2, starting from the product prepared according to example 163, the desired product is obtained in the form of a white powder (yield=57%).
M.p.=132° C.
$[\alpha]_D^{28}$=−41° (c=0.29; DMSO).

EXAMPLE 165

6-(1-Methyl-1H-pyrazol-4-yl)-3-pyridinyl 2,3,4-tri-O-acetyl-5-thio-β-D-xylo-pyranoside By carrying out the operation analogously to example 1, starting from 6-bromo-3-pyridinyl 2,3,4-tri-O-acetyl-5-thio-β-D-xylopyranoside, obtained according to preparation IV, and 1-methyl-4-(pinacolatoboryl)-1H-pyrazole, the desired product is obtained in the form of a white solid (yield=46%).
M.p.=183° C.
$[\alpha]_D^{28}$=+7° (c=0.18; DMSO).

EXAMPLE 166

6-(1-Methyl-1H-pyrazol-4-yl)-3-pyridinyl 5-thio-β-D-xylopyranoside

By carrying out the operation analogously to example 2, starting from the product prepared according to example 165, the desired product is obtained in the form of a white solid (yield=65%).
$[\alpha]_D^{28}$=−50° (c=0.20; DMSO).

EXAMPLE 167

6-(3,5-Dimethyl-1H-pyrazol-4-yl)-3-pyridinyl 2,3,4-tri-O-acetyl-5-thio-β-D-xylopyranoside By carrying out the operation analogously to example 1, starting from 6-bromo-3-pyridinyl 2,3,4-tri-O-acetyl-5-thio-β-D-xylopyranoside, obtained according to preparation IV, and 3,5-dimethyl-4-(pinacolatoboryl)-1H-pyrazole, the desired product is obtained in the form of a white solid (yield=21%).
M.p.=154° C.
$[\alpha]_D^{28}$=−1° (c=0.26; DMSO).

EXAMPLE 168

6-(3,5-Dimethyl-1H-pyrazol-4-yl)-3-pyridinyl 5-thio-β-D-xylopyranoside

By carrying out the operation analogously to example 2, starting from the product prepared according to example 167, the desired product is obtained in the form of a white solid (yield=72%).
M.p.=210° C.
$[\alpha]_D^{28}$=−47° (c=0.24; DMSO).

EXAMPLE 169

5-(6-Fluoro-3-pyridinyl)-3-pyridinyl 2,3,4-tri-O-acetyl-5-thio-β-D-xylo-pyranoside By carrying out the operation analogously to example 1, starting from 5-bromo-3-pyridinyl 2,3,4-tri-O-acetyl-5-thio-β-D-xylopyranoside, obtained according to preparation IX, and 6-fluoro-3-pyridineboronic acid, the desired product is obtained in the form of a cream solid (yield=56%).
M.p.=167-169° C.
$[\alpha]_D^{27}$=−18° (c=0.23; DMSO).

EXAMPLE 170

5-(6-Fluoro-3-pyridinyl)-3-pyridinyl 5-thio-β-D-xylopyranoside

By carrying out the operation analogously to example 124, starting from the product prepared according to example 169, the desired product is obtained in the form of a white solid (yield=47%).
M.p.=210-212° C.
$[\alpha]_D^{24}$=−47° (c=0.14; DMSO).

EXAMPLE 171

5-(1-Methyl-1H-pyrazol-4-yl)-3-pyridinyl 2,3,4-tri-O-acetyl-5-thio-β-D-xylo-pyranoside By carrying out the operation analogously to example 1, starting from 5-bromo-3-pyridinyl 2,3,4-tri-O-acetyl-5-thio-β-D-xylopyranoside, obtained according to preparation IX, and 1-methyl-4-(pinacolatoboryl)-1H-pyrazole, the desired product is obtained in the form of a beige solid (yield=58%).
M.p.=68° C.
$[\alpha]_D^{29}$=−19° (c=0.20; DMSO).

EXAMPLE 172

5-(1-Methyl-1H-pyrazol-4-yl)-3-pyridinyl 5-thio-β-D-xylopyranoside

By carrying out the operation analogously to example 2, starting from the product prepared according to example 171, the desired product is obtained in the form of a white solid (yield=72%).
M.p.=216° C.
$[\alpha]_D^{29}$=−74° (c=0.25; DMSO).

EXAMPLE 173

6-(2,4-Dimethyl-5-thiazolyl)-3-pyridinyl 2,3,4-tri-O-acetyl-5-thio-β-D-xylo-pyranoside By carrying out the operation analogously to example 1, starting from 6-bromo-3-pyridinyl 2,3,4-tri-O-acetyl-5-thio-β-D-xylopyranoside, obtained according to preparation IV, and 2,4-dimethyl-5-(pinacolatoboryl)thiazole, the desired product is obtained in the form of white crystals (yield=21%).
M.p.=174-177° C. (crystallized from ethyl ether).
$[\alpha]_D^{32}$=+9° (c=0.43; DMSO).

EXAMPLE 174

6-(2,4-Dimethyl-5-thiazolyl)-3-pyridinyl 5-thio-β-D-xylopyranoside

By carrying out the operation analogously to example 42, starting from the product prepared according to example 173, the desired product is obtained in the form of cream crystals (yield=92%).
M.p.=175° C.
$[\alpha]_D^{32}$=−53° (c=0.41; DMSO).

EXAMPLE 175

6-(2-Methyl-3-pyridinyl)-3-pyridinyl 2,3,4-tri-O-acetyl-5-thio-β-D-xylo-pyranoside By carrying out the operation analogously to example 137, starting from 6-bromo-3-pyridinyl 2,3,4-tri-O-acetyl-5-thio-β-D-xylopyranoside, obtained according to preparation IV, and 2-methyl-3-(pinacolatoboryl)pyridine (obtained from 2-methyl-3-pyridinyl trifluoromethanesulfonate), the desired product is obtained in the form of a white solid (yield=11%).
M.p.=198-200° C.
$[\alpha]_D^{29}$=−3° (c=0.21; DMSO).

EXAMPLE 176

6-(2-Methyl-3-pyridinyl)-3-pyridinyl 5-thio-β-D-xylopyranoside

By carrying out the operation analogously to example 2, starting from the product prepared according to example 175, the desired product is obtained in the form of a white solid (yield=39%).
M.p.=167-168° C.
$[\alpha]_D^{32}$=−26° (c=0.32; DMSO).

EXAMPLE 177

5-(5-Pyrimidinyl)-3-pyridinyl 2,3,4-tri-O-acetyl-5-thio-β-D-xylopyranoside 0.2 g (0.45 mM) of 5-bromo-3-pyridinyl 2,3,4-tri-O-acetyl-5-thio-β-D-xylopyranoside, obtained according to preparation IX, 66 mg (0.53 mM) of 5-pyrimidineboronic acid, 0.281 g (0.90 mM) of resin grafted with benzyltriethylammonium carbonate and 36 mg (0.044 mM) of the [1,1'-bis(diphenylphosphino)ferrocene]dichloropalladium(II) complex with dichloromethane are mixed in 3 ml of DME and 2 ml of methanol. The reaction mixture is brought to 120° C. for 30 minutes by heating under microwave radiation. After filtering and rinsing the solid residue with methanol, the resulting solution is concentrated under reduced pressure. The evaporation residue is purified by chromatography on a silica column (eluent: dichloromethane/methanol 70/30; v/v) and the product is subsequently recrystallized from isopropanol in order to obtain the expected product in the form of pearlescent pink crystals with a yield of 50%.
M.p.=213-217° C.
$[\alpha]_D^{30}$=−4 (c=0.10; DMSO).

EXAMPLE 178

5-(5-Pyrimidinyl)-3-pyridinyl 5-thio-β-D-xylopyranoside

By carrying out the operation analogously to example 42, starting from the product prepared according to example 177, the desired product is obtained in the form of a pink powder (yield=67%).
M.p.=196° C.
$[\alpha]_D^{30}$=−96° (c=0.17; DMSO).

EXAMPLE 179

5-(3,5-Dimethyl-4-isoxazolyl)-3-pyridinyl 2,3,4-tri-O-acetyl-5-thio-β-D-xylo-pyranoside By carrying out the operation analogously to example 177, starting from 3,5-dimethyl-4-isoxazoleboronic acid, the desired product is obtained in the form of white crystals (yield=33%).
M.p.=129-131° C.
$[\alpha]_D^{30}$=−36° (c=0.10; DMSO).

EXAMPLE 180

5-(3,5-Dimethyl-4-isoxazolyl)-3-pyridinyl 5-thio-β-D-xylopyranoside

By carrying out the operation analogously to example 42, starting from the product prepared according to example 179, the desired product is obtained in the form of white crystals (yield=70%).
M.p.=222-223° C.
$[\alpha]_D^{24}$=−51° (c=0.10; DMSO).

EXAMPLE 181

2-(3,5-Dimethyl-4-isoxazolyl)-3-pyridinyl 2,3,4-tri-O-acetyl-5-thio-β-D-xylo-pyranoside By carrying out the operation analogously to example 179, starting from 2-bromo-3-pyridinyl 2,3,4-tri-O-acetyl-5-thio-β-D-xylopyranoside, obtained according to preparation III, the desired product is obtained in the form of a pink foam (yield=49%).
M.p.=68-72° C.
$[\alpha]_D^{27}$=−92° (c=0.24; DMSO).

EXAMPLE 182

2-(3,5-Dimethyl-4-isoxazolyl)-3-pyridinyl 5-thio-β-D-xylopyranoside

By carrying out the operation analogously to example 42, starting from the product prepared according to example 181, the desired product is obtained in the form of an off-white powder (yield=65%).
M.p.=112° C.
$[\alpha]_D^{27}$=−53° (c=0.24; DMSO).

EXAMPLE 183

5-(2-Fluoro-3-pyridinyl)-3-pyridinyl 2,3,4-tri-O-acetyl-5-thio-β-D-xylo-pyranoside By carrying out the operation analogously to example 177, starting from 2-fluoro-3-pyridineboronic acid, the desired product is obtained in the form of beige crystals (yield=52%).
M.p.=169-170° C. (recrystallized from isopropanol).
$[\alpha]_D^{24}$=−37° (c=0.17; DMSO).

EXAMPLE 184

5-(2-Fluoro-3-pyridinyl)-3-pyridinyl 5-thio-β-D-xylopyranoside

By carrying out the operation analogously to example 2, starting from the product prepared according to example 183, the desired product is obtained in the form of a white solid (yield=46%).
M.p.=193-196° C.
$[\alpha]_D^{31}$=−81° (c=0.11; DMSO).

EXAMPLE 185

5-(2-Fluoro-4-pyridinyl)-3-pyridinyl 2,3,4-tri-O-acetyl-5-thio-β-D-xylo-pyranoside By carrying out the operation analogously to example 177, starting from 2-fluoro-4-pyridineboronic acid, the desired product is obtained in the form of a beige solid (yield=70%).
M.p.=122-125° C.
$[\alpha]_D^{31}$=−29° (c=0.11; DMSO).

EXAMPLE 186

5-(2-Fluoro-4-pyridinyl)-3-pyridinyl 5-thio-β-D-xylopyranoside

By carrying out the operation analogously to example 2, starting from the product prepared according to example 185, the desired product is obtained in the form of a white solid (yield=76%).
M.p.=208° C. (recrystallized from methanol).
$[\alpha]_D^{28}$=−92° (c=0.32; DMSO).

EXAMPLE 187

6-(2-Fluoro-3-pyridinyl)-3-pyridinyl 2,3,4-tri-O-acetyl-5-thio-β-D-xylopyranoside By carrying out the operation analogously to example 183, starting from 6-bromo-3-pyridinyl 2,3,4-tri-O-acetyl-5-thio-β-D-xylopyranoside, obtained according to preparation IV, the desired product is obtained in the form of a cream powder (yield=38%).
M.p.=153° C.
$[\alpha]_D^{26}$=−7° (c=0.19; DMSO).

EXAMPLE 188

6-(2-Fluoro-3-pyridinyl)-3-pyridinyl 5-thio-β-D-xylopyranoside

By carrying out the operation analogously to example 2, starting from the product prepared according to example 187, the desired product is obtained in the form of a white powder (yield=88%).
M.p.=181° C. (recrystallized from water).
$[\alpha]_D^{27}$=−48° (c=0.17; DMSO).

EXAMPLE 189

6-(5-Pyrimidinyl)-3-pyridinyl 2,3,4-tri-O-acetyl-5-thio-β-D-xylopyranoside

By carrying out the operation analogously to example 187, starting from 5-pyrimidineboronic acid, the desired product is obtained in the form of a pink solid (yield=39%).
M.p.=215° C. (crystallized from ethyl ether).
$[\alpha]_D^{28}$=−2° (c=0.18; DMSO).

EXAMPLE 190

6-(5-Pyrimidinyl)-3-pyridinyl 5-thio-β-D-xylopyranoside

By carrying out the operation analogously to example 42, starting from the product prepared according to example 189, the desired product is obtained in the form of a pink powder (yield=77%).
M.p.=188° C.
$[\alpha]_D^{27}$=−45° (c=0.19; DMSO).

EXAMPLE 191

6-(3,5-Dimethyl-4-isoxazolyl)-3-pyridinyl 2,3,4-tri-O-acetyl-5-thio-β-D-xylo-pyranoside By carrying out the operation analogously to example 187, starting from 3,5-dimethyl-4-isoxazoleboronic acid, the desired product is obtained in the form of a white solid (yield=21%).
M.p.=172° C. (recrystallized from ethyl ether).
$[\alpha]_D^{28}$=−13° (c=0.14; DMSO).

EXAMPLE 192

6-(3,5-Dimethyl-4-isoxazolyl)-3-pyridinyl 5-thio-β-D-xylopyranoside

By carrying out the operation analogously to example 42, starting from the product prepared according to example 191, the desired product is obtained in the form of a fluffy white solid (yield=52%).
M.p.=138° C.
$[\alpha]_D^{27}$=−43° (c=0.10; DMSO).

EXAMPLE 193

6-(6-Fluoro-3-pyridinyl)-3-pyridinyl 2,3,4-tri-O-acetyl-5-thio-β-D-xylo-pyranoside By carrying out the operation analogously to example 187, starting from 6-fluoro-3-pyridineboronic acid, the desired product is obtained in the form of white flakes (yield=30%).
M.p.=185° C. (recrystallized from an ethanol/water mixture).
$[\alpha]_D^{28}$=+3° (c=0.43; DMSO).

EXAMPLE 194

6-(6-Fluoro-3-pyridinyl)-3-pyridinyl 5-thio-β-D-xylopyranoside

By carrying out the operation analogously to example 2, starting from the product prepared according to example 193, the desired product is obtained in the form of a white powder (yield=98%).
M.p.=143-156° C.
$[\alpha]_D^{28}$=−56° (c=0.26; DMSO).

EXAMPLE 195

2-Fluoro-5-(2-fluoro-4-pyridinyl)-3-pyridinyl 2,3,4-tri-O-acetyl-5-thio-β-D-xylopyranoside By carrying out the operation analogously to example 177, starting from 5-bromo-2-fluoro-3-pyridinyl 2,3,4-tri-O-acetyl-5-thio-β-D-xylopyranoside, obtained according to preparation VIII, and 2-fluoro-4-pyridineboronic acid, the desired product is obtained in the form of a pink solid (yield=65%).
M.p.=142-144° C.
$[\alpha]_D^{30}$=−9° (c=0.25; DMSO).

EXAMPLE 196

2-Fluoro-5-(2-fluoro-4-pyridinyl)-3-pyridinyl 5-thio-β-D-xylopyranoside

By carrying out the operation analogously to example 2, starting from the product prepared according to example 195, the desired product is obtained in the form of a gray solid (yield=65%).
M.p.=145-146° C.
$[\alpha]_D^{30}$=+8° (c=0.24; DMSO).

EXAMPLE 197

2-Fluoro-5-(6-fluoro-3-pyridinyl)-3-pyridinyl 2,3,4-tri-O-acetyl-5-thio-β-D-xylopyranoside By carrying out the operation analogously to example 195, starting from 6-fluoro-3-pyridineboronic acid, the desired product is obtained in the form of a pink solid (yield=35%).
M.p.=135-136° C.
$[\alpha]_D^{30}$=−22° (c=0.28; DMSO).

EXAMPLE 198

2-Fluoro-5-(6-fluoro-3-pyridinyl)-3-pyridinyl 5-thio-β-D-xylopyranoside

By carrying out the operation analogously to example 2, starting from the product prepared according to example 197, the desired product is obtained in the form of a gray solid (yield=71%).
M.p.=158-159° C.
$[\alpha]_D^{30}$=−72° (c=0.30; DMSO).

EXAMPLE 199

5-(3-Thienyl)-3-pyridinyl 2,3,4-tri-O-acetyl-5-thio-β-D-xylopyranoside

By carrying out the operation analogously to example 177, starting from 3-thienylboronic acid, the desired product is obtained in the form of a beige solid (yield=25%).
M.p.=175° C.
$[\alpha]_D^{27}$=+6° (c=0.25; DMSO).

EXAMPLE 200

5-(3-Thienyl)-3-pyridinyl 5-thio-β-D-xylopyranoside

By carrying out the operation analogously to example 42, starting from the product prepared according to example 199, the desired product is obtained in the form of a white solid (yield=32%).
M.p.=212° C.
$[\alpha]_D^{27}$=−113° (c=0.10; DMSO).

EXAMPLE 201

6-(2-Chloro-4-pyridinyl)-3-pyridinyl 2,3,4-tri-O-acetyl-5-thio-β-D-xylo-pyranoside By carrying out the operation analogously to example 187, starting from 2-chloro-4-pyridineboronic acid, the desired product is obtained in the form of a pink powder (yield=21%).
M.p.=226° C.
$[\alpha]_D^{29}$=+12° (c=0.20; DMSO).

EXAMPLE 202

6-(2-Chloro-4-pyridinyl)-3-pyridinyl 5-thio-β-D-xylopyranoside

By carrying out the operation analogously to example 2, starting from the product prepared according to example 201, the desired product is obtained in the form of a yellow powder (yield=62%).
M.p.=179° C. (recrystallized from water).
$[\alpha]_D^{29}$=−36° (c=0.13; DMSO).

EXAMPLE 203

4-(3,5-Dimethyl-4-isoxazolyl)-3-pyridinyl 2,3,4-tri-O-acetyl-5-thio-β-D-xylo-pyranoside By carrying out the operation analogously to example 177, starting from 4-bromo-3-pyridinyl 2,3,4-tri-O-acetyl-5-thio-β-D-xylopyranoside, obtained according to preparation II, and 3,5-dimethyl-4-isoxazoleboronic acid, the desired product is obtained in the form of a pink powder (yield=30%).
M.p.=150-155° C.
$[\alpha]_D^{25}$=−38° (c=0.10; DMSO).

EXAMPLE 204

4-(3,5-Dimethyl-4-isoxazolyl)-3-pyridinyl 5-thio-β-D-xylopyranoside

By carrying out the operation analogously to example 2, starting from the product prepared according to example 203, the desired product is obtained in the form of a beige powder (yield=62%).
M.p.=175-179° C.
$[\alpha]_D^{31}$=−159° (c=0.10; DMSO).

EXAMPLE 205

6-Methyl-2-(3-pyridinyl)-3-pyridinyl 2,3,4-tri-O-acetyl-5-thio-β-D-xylo-pyranoside By carrying out the operation analogously to example 177, starting from 2-iodo-6-methyl-3-pyridinyl 2,3,4-tri-O- acetyl-5-thio-β-D-xylopyranoside, obtained according to preparation V, and 3-pyridineboronic acid, the desired product is obtained in the form of an ocher powder (yield=42%).
M.p.=92-102° C.
$[\alpha]_D^{26}$=−82° (c=0.10; DMSO).

EXAMPLE 206

6-Methyl-2-(3-pyridinyl)-3-pyridinyl 5-thio-β-D-xylopyranoside

By carrying out the operation analogously to example 42, starting from the product prepared according to example 205, the desired product is obtained in the form of a yellow powder (yield=72%).
M.p.=160-170° C.
$[\alpha]_D^{25}$=−19° (c=0.18; DMSO).

EXAMPLE 207

6-Methyl-2-(4-pyridinyl)-3-pyridinyl 2,3,4-tri-O-acetyl-5-thio-β-D-xylo-pyranoside By carrying out the operation analogously to example 205, starting from 4-pyridineboronic acid, the desired product is obtained in the form of a pale pink powder (yield=54%).
M.p.=140-144° C.
$[\alpha]_D^{34}$=−54° (c=0.11; DMSO).

EXAMPLE 208

6-Methyl-2-(4-pyridinyl)-3-pyridinyl 5-thio-β-D-xylopyranoside

By carrying out the operation analogously to example 42, starting from the product prepared according to example 207, the desired product is obtained in the form of a beige powder (yield=95%).
M.p.=196-200° C.
$[\alpha]_D^{25}$=−35° (c=0.10; DMSO).

EXAMPLE 209

6-(2-Fluoro-4-pyridinyl)-3-pyridinyl 2,3,4-tri-O-acetyl-5-thio-β-D-xylo-pyranoside By carrying out the operation analogously to example 187, starting from 2-fluoro-4-pyridineboronic acid, the desired product is obtained in the form of a white solid (yield=30%).
M.p.=179° C.
$[\alpha]_D^{30}$=+1° (c=0.82; DMSO).

EXAMPLE 210

6-(2-Fluoro-4-pyridinyl)-3-pyridinyl 5-thio-β-D-xylopyranoside

By carrying out the operation analogously to example 124, starting from the product prepared according to example 209, the desired product is obtained in the form of a white solid (yield=56%).
M.p.=219° C.
$[\alpha]_D^{32}$=−49° (c=0.28; DMSO).

EXAMPLE 211

2-(5-Pyrimidinyl)-3-pyridinyl 2,3,4-tri-O-acetyl-5-thio-β-D-xylopyranoside

By carrying out the operation analogously to example 181, starting from 5-pyrimidineboronic acid, the desired product is obtained in the form of a cream solid (yield=48%).
M.p.=205° C. (recrystallized from ethyl ether).
$[\alpha]_D^{30}$=−76° (c=0.61; DMSO).

EXAMPLE 212

2-(5-Pyrimidinyl)-3-pyridinyl 5-thio-β-D-xylopyranoside

By carrying out the operation analogously to example 42, starting from the product prepared according to example 211, the desired product is obtained in the form of a pink powder (yield=36%).
M.p.=195° C. (recrystallized from a methanol/ethyl ether mixture).
$[\alpha]_D^{30}$=−38° (c=0.27; DMSO).

EXAMPLE 213

5-Fluoro-6-(6-fluoro-3-pyridinyl)-3-pyridinyl 2,3,4-tri-O-acetyl-5-thio-β-D-xylopyranoside A solution of 0.421 g (1 mM) of 6-chloro-5-fluoro-3-pyridinyl 2,3,4-tri-O-acetyl-5-thio-β-D-xylopyranoside, obtained according to preparation XI, in 4 ml of DME is prepared. 0.211 g (1.5 mM) of 6-fluoro-3-pyridineboronic acid, 0.082 g (0.1 mM) of the [1,1'-bis(diphenylphosphino)ferrocene]dichloropalladium(II) complex with dichloromethane and then 1.5 ml (1.5 mM) of a 1M potassium carbonate solution are added. The reaction medium is heated at 120° C. for 30 min using microwave radiation. After cooling and separating by settling, the organic phase is withdrawn and the extraction is completed by the addition of ethyl acetate. The combined organic phases are evaporated under reduced pressure and the evaporation product is dissolved in 4 ml of dichloromethane and washed successively with water, a 1M potassium carbonate solution and then water. The organic phase is filtered through a hydrophobic membrane and evaporated under a stream of nitrogen. The desired product is obtained and is used directly in the deacetylation stage.

EXAMPLE 214

5-Fluoro-6-(6-fluoro-3-pyridinyl)-3-pyridinyl 5-thio-β-D-xylopyranoside

By carrying out the operation analogously to example 2, starting from the product prepared according to example 213, the desired product is obtained in the form of a white solid with a yield of 75%.
M.p.=184° C.
$[\alpha]_D^{33}$=−54° (c=0.10; DMSO).

EXAMPLE 215

5-Fluoro-6-(6-methyl-3-pyridinyl)-3-pyridinyl 2,3,4-tri-O-acetyl-5-thio-β-D-xylopyranoside By carrying out the operation analogously to example 213, starting from 6-methyl-3-pyridineboronic acid, the desired product is obtained and is used directly in the deacetylation stage.

EXAMPLE 216

5-Fluoro-6-(6-methyl-3-pyridinyl)-3-pyridinyl 5-thio-β-D-xylopyranoside

By carrying out the operation analogously to example 2, starting from the product prepared according to example 215, the desired product is obtained in the form of a white solid (yield=58%).
M.p.=184° C.
$[\alpha]_D^{33}=-54°$ (c=0.24; DMSO).

EXAMPLE 217

5-(2-Methoxy-5-pyrimidinyl)-3-pyridinyl 2,3,4-tri-O-acetyl-5-thio-β-D-xylo-pyranoside By carrying out the operation analogously to example 213, starting from 5-bromo-3-pyridinyl 2,3,4-tri-O-acetyl-5-thio-β-D-xylopyranoside, obtained according to preparation IX, and 2-methoxy-5-pyrimidineboronic acid, the desired product is obtained and is used directly in the deacetylation stage.

EXAMPLE 218

5-(2-Methoxy-5-pyrimidinyl)-3-pyridinyl 5-thio-β-D-xylopyranoside

By carrying out the operation analogously to example 2, starting from the product prepared according to example 217, the desired product is obtained in the form of a white solid (yield=46%).
M.p.=215° C.
$[\alpha]_D^{30}=-75°$ (c=0.10; DMSO).

EXAMPLE 219

5-Fluoro-6-(2-methyl-4-pyridinyl)-3-pyridinyl 2,3,4-tri-O-acetyl-5-thio-β-D-xylopyranoside By carrying out the operation analogously to example 213, starting from 2-methyl-4-pyridineboronic acid, the desired product is obtained and is used directly in the deacetylation stage.

EXAMPLE 220

5-Fluoro-6-(2-methyl-4-pyridinyl)-3-pyridinyl 5-thio-β-D-xylopyranoside

By carrying out the operation analogously to example 2, starting from the product prepared according to example 219, the desired product is obtained in the form of a white solid (yield=31%).
M.p.=143° C.
$[\alpha]_D^{30}=-27°$ (c=0.10; DMSO).

EXAMPLE 221

5-Fluoro-6-(2-methoxy-3-pyridinyl)-3-pyridinyl 2,3,4-tri-O-acetyl-5-thio-β-D-xylopyranoside By carrying out the operation analogously to example 213, starting from 2-methoxy-3-pyridineboronic acid, the desired product is obtained and is used directly in the deacetylation stage.

EXAMPLE 222

5-Fluoro-6-(2-methoxy-3-pyridinyl)-3-pyridinyl 5-thio-β-D-xylopyranoside

By carrying out the operation analogously to example 2, starting from the product prepared according to example 221, the desired product is obtained in the form of a white solid (yield=77%).
M.p.=141° C.
$[\alpha]_D^{30}=-35°$ (c=0.10; DMSO).

EXAMPLE 223

5-Fluoro-6-(1-methyl-1H-pyrazol-4-yl)-3-pyridinyl 2,3,4-tri-O-acetyl-5-thio-β-D-xylopyranoside By carrying out the operation analogously to example 213, starting from 1-methyl-4-(pinacolatoboryl)-1H-pyrazole, the desired product is obtained and is used directly in the deacetylation stage.

EXAMPLE 224

5-Fluoro-6-(1-methyl-1H-pyrazol-4-yl)-3-pyridinyl 5-thio-β-D-xylopyranoside

By carrying out the operation analogously to example 2, starting from the product prepared according to example 223, the desired product is obtained in the form of a white solid (yield=41%).
M.p.=206° C.
$[\alpha]_D^{30}=-46°$ (c=0.10; DMSO).

EXAMPLE 225

6-(3,5-Dimethyl-4-isoxazolyl)-5-fluoro-3-pyridinyl 2,3,4-tri-O-acetyl-5-thio-β-D-xylopyranoside By carrying out the operation analogously to example 213, starting from 3,5-dimethyl-4-isoxazoleboronic acid, the desired product is obtained and is used directly in the deacetylation stage.

EXAMPLE 226

6-(3,5-Dimethyl-4-isoxazolyl)-5-fluoro-3-pyridinyl 5-thio-β-D-xylopyranoside

By carrying out the operation analogously to example 2, starting from the product prepared according to example 225, the desired product is obtained in the form of a white solid (yield=33%).
M.p.=177° C.
$[\alpha]_D^{30}=-48°$ (c=0.12; DMSO).

EXAMPLE 227

6-(2-Methoxy-5-pyrimidinyl)-3-pyridinyl 2,3,4-tri-O-acetyl-5-thio-β-D-xylo-pyranoside By carrying out the operation analogously to example 213, starting from 6-bromo-3-pyridinyl 2,3,4-tri-O-acetyl-5-thio-β-D-xylopyranoside, obtained according to preparation IV, and 2-methoxy-5-pyrimidineboronic acid, the desired product is obtained and is used directly in the deacetylation stage.

EXAMPLE 228

6-(2-Methoxy-5-pyrimidinyl)-3-pyridinyl 5-thio-β-D-xylopyranoside

By carrying out the operation analogously to example 2, starting from the product prepared according to example 227, the desired product is obtained in the form of a white solid (yield=20%).
M.p.=134° C.
$[\alpha]_D^{26}=-53°$ (c=0.10; DMSO).

EXAMPLE 229

5-Fluoro-6-(5-pyrimidinyl)-3-pyridinyl 2,3,4-tri-O-acetyl-5-thio-β-D-xylo-pyranoside By carrying out the operation analogously to example 213, starting from 5-pyrimidineboronic acid, the desired product is obtained and is used directly in the deacetylation stage.

EXAMPLE 230

5-Fluoro-6-(5-pyrimidinyl)-3-pyridinyl 5-thio-β-D-xylopyranoside

By carrying out the operation analogously to example 2, starting from the product prepared according to example 229, the desired product is obtained in the form of a white solid (yield=19%).
M.p.=192° C.
$[\alpha]_D^{33}=-34°$ (c=0.12; DMSO).

EXAMPLE 231

5-(3-Chloro-2-pyridinyl)-3-pyridinyl 2,3,4-tri-O-acetyl-5-thio-β-D-xylo-pyranoside A solution of 0.448 g (1 mM) of 5-bromo-3-pyridinyl 2,3,4-tri-O-acetyl-5-thio-β-D-xylopyranoside, obtained according to preparation IX, in 2 ml of DME is used to prepare the boronate according to the method described in example 49. The reaction medium is subsequently filtered and then rinsing is carried out with DME. 0.422 g (1.66 mM) of 2,3-dichloropyridine, 0.020 g (0.025 mM) of the [1,1'-bis(diphenylphosphino)ferrocene]dichloropalladium(II) complex with dichloromethane and then 1.5 ml (1.5 mM) of a 1M potassium carbonate solution are added to the resulting solution. The reaction medium is heated at 120° C. for 30 min using microwave radiation. After cooling and separating by settling, the organic phase is withdrawn and the extraction is completed by the addition of ethyl acetate. The combined organic phases are evaporated under reduced pressure and the evaporation product is dissolved in 4 ml of dichloromethane and washed successively with water, a 1M potassium carbonate solution and then water. The organic phase is filtered through a hydrophobic membrane and evaporated under a stream of nitrogen. The desired product is obtained and is used directly in the deacetylation stage.

EXAMPLE 232

5-(3-Chloro-2-pyridinyl)-3-pyridinyl 5-thio-β-D-xylopyranoside

By carrying out the operation analogously to example 2, starting from the product prepared according to example 231, the desired product is obtained in the form of a white solid (yield=50%).
M.p.=193° C.
$[\alpha]_D^{30}=-46°$ (c=0.18; DMSO).

EXAMPLE 233

5-(5-Methyl-2-pyridinyl)-3-pyridinyl 2,3,4-tri-O-acetyl-5-thio-β-D-xylo-pyranoside By carrying out the operation analogously to example 231, starting from 2-bromo-5-methylpyridine, the desired product is obtained and is used directly in the deacetylation stage.

EXAMPLE 234

5-(5-Methyl-2-pyridinyl)-3-pyridinyl 5-thio-β-D-xylopyranoside

By carrying out the operation analogously to example 2, starting from the product prepared according to example 233, the desired product is obtained in the form of a white solid (yield=33%).
M.p.=199° C.
$[\alpha]_D^{29}=-64°$ (c=0.18; DMSO).

EXAMPLE 235

5-(4-Methyl-2-pyridinyl)-3-pyridinyl 2,3,4-tri-O-acetyl-5-thio-β-D-xylo-pyranoside By carrying out the operation analogously to example 231, starting from 2-bromo-4-methylpyridine, the desired product is obtained and is used directly in the deacetylation stage.

EXAMPLE 236

5-(4-Methyl-2-pyridinyl)-3-pyridinyl 5-thio-β-D-xylopyranoside

By carrying out the operation analogously to example 2, starting from the product prepared according to example 235, the desired product is obtained in the form of a white powder (yield=20%).
M.p.=166° C.
$[\alpha]_D^{29}=-80°$ (c=0.10; DMSO).

EXAMPLE 237

5-(6-Methyl-2-pyridinyl)-3-pyridinyl 2,3,4-tri-O-acetyl-5-thio-β-D-xylo-pyranoside By carrying out the operation analogously to example 231, starting from 2-bromo-6-methylpyridine, the desired product is obtained and is used directly in the deacetylation stage.

EXAMPLE 238

5-(6-Methyl-2-pyridinyl)-3-pyridinyl 5-thio-β-D-xylopyranoside

By carrying out the operation analogously to example 2, starting from the product prepared according to example 237, the desired product is obtained in the form of a white powder (yield=49%).
M.p.=188° C.
$[\alpha]_D^{29}$=−68° (c=0.30; DMSO).

EXAMPLE 239

6-Methyl-2-(3,5-dimethyl-4-isoxazolyl)-3-pyridinyl 5-thio-β-D-xylopyranoside 0.3 g (0.59 mM) of 2-iodo-6-methyl-3-pyridinyl 2,3,4-tri-O-acetyl-5-thio-β-D-xylopyranoside, obtained according to preparation V, 0.1 g (0.71 mM) of 3,5-dimethyl-4-isoxazoleboronic acid, 0.384 g (1.17 mM) of cesium carbonate and 0.327 g of tetrakis(triphenylphosphine)palladium grafted to polystyrene resin are mixed in 5 ml of DME and 3.5 ml of methanol. The mixture is heated at 120° C. for 30 minutes using microwave radiation. The reaction mixture is subsequently filtered, the residual solid is rinsed with methanol and the filtrate is concentrated under reduced pressure. The evaporation residue is purified by chromatography on a silica column, elution being carried out using a dichloromethane/methanol mixture (80/20; v/v), to give the expected product in the form of a white powder with a yield of 70%.
M.p.=70-84° C.
$[\alpha]_D^{31}$=−64° (c=0.11; DMSO).

EXAMPLE 240

2-(6-Fluoro-3-pyridinyl)-3-pyridinyl 5-thio-β-D-xylopyranoside

By carrying out the operation analogously to example 239, starting from 2-bromo-3-pyridinyl 2,3,4-tri-O-acetyl-5-thio-β-D-xylopyranoside, obtained according to preparation III, and 6-fluoro-3-pyridineboronic acid, the desired product is obtained in the form of a white powder (yield=14%).
M.p.=199° C.
$[\alpha]_D^{32}$=−54° (c=0.26; DMSO).

EXAMPLE 241

2-(3,5-Dimethyl-4-isoxazolyl)-4-pyridinyl 5-thio-β-D-xylopyranoside

By carrying out the operation analogously to example 239, starting from 2-bromo-4-pyridinyl 2,3,4-tri-O-acetyl-5-thio-β-D-xylopyranoside, obtained according to preparation VII, and 3,5-dimethyl-4-isoxazoleboronic acid, the desired product is obtained in the form of white crystals (yield=25%).
M.p.=143-147° C. (recrystallized from water).
$[\alpha]_D^{27}$=−77° (c=0.22; DMSO).

EXAMPLE 242

5-(4-Methoxy-3-pyridinyl)-3-pyridinyl 5-thio-β-D-xylopyranoside

By carrying out the operation analogously to example 239, starting from 5-bromo-3-pyridinyl 2,3,4-tri-O-acetyl-5-thio-β-D-xylopyranoside, obtained according to preparation IX, and 4-methoxy-3-pyridineboronic acid, the desired product is obtained in the form of a white solid (yield=23%).
M.p.=154° C.
$[\alpha]_D^{29}$=−49° (c=0.30; DMSO).

EXAMPLE 243

6-(4-Methoxy-3-pyridinyl)-3-pyridinyl 5-thio-β-D-xylopyranoside

By carrying out the operation analogously to example 239, starting from 6-bromo-3-pyridinyl 2,3,4-tri-O-acetyl-5-thio-β-D-xylopyranoside, obtained according to preparation IV, and 4-methoxy-3-pyridineboronic acid, the desired product is obtained in the form of a white solid (yield=37%).
M.p.=207° C.
$[\alpha]_D^{27}$=−11° (c=0.25; DMSO).

EXAMPLE 244

5-(2-Methyl-4-pyridinyl)-3-pyridinyl 5-thio-β-D-xylopyranoside

By carrying out the operation analogously to example 239, starting from 5-bromo-3-pyridinyl 2,3,4-tri-O-acetyl-5-thio-β-D-xylopyranoside, obtained according to preparation IX, and 2-methyl-4-pyridineboronic acid, the desired product is obtained in the form of a white solid (yield=28%).
M.p.=120° C. (recrystallized from water).
$[\alpha]_D^{29}$=−77° (c=0.17; DMSO).

EXAMPLE 245

6-(2-Methyl-4-pyridinyl)-3-pyridinyl 5-thio-β-D-xylopyranoside

By carrying out the operation analogously to example 239, starting from 6-bromo-3-pyridinyl 2,3,4-tri-O-acetyl-5-thio-β-D-xylopyranoside, obtained according to preparation IV, and 2-methyl-4-pyridineboronic acid, the desired product is obtained in the form of a white powder (yield=23%).
M.p.=214° C. (recrystallized from water).
$[\alpha]_D^{28}$=−51° (c=0.52; DMSO).

EXAMPLE 246

6-(5-Chloro-3-pyridinyl)-3-pyridinyl 2,3,4-tri-O-acetyl-5-thio-β-D-xylo-pyranoside By carrying out the operation analogously to example 1, starting from 6-bromo-3-pyridinyl 2,3,4-tri-O-acetyl-5-thio-β-D-xylopyranoside, obtained according to preparation IV, and 5-chloro-3-pyridineboronic acid, the desired product is obtained in the form of a white solid (yield=40%).
M.p.=203-205° C.
$[\alpha]_D^{30}$=+8° (c=0.31; DMSO).

EXAMPLE 247

6-(5-Chloro-3-pyridinyl)-3-pyridinyl 5-thio-β-D-xylopyranoside

By carrying out the operation analogously to example 42, starting from the product prepared according to example 246, the desired product is obtained in the form of a white solid (yield=28%).
M.p.=171-172° C.
$[\alpha]_D^{30}$=−167° (c=0.24; DMSO).

EXAMPLE 248

5-(4-Methyl-3-pyridinyl)-3-pyridinyl 2,3,4-tri-O-acetyl-5-thio-β-D-xylo-pyranoside By carrying out the operation analogously to example 137, starting from 3-bromo-4-methylpyridine, the desired product is obtained in the form of a white solid (yield=9%).
M.p.=165° C.
$[\alpha]_D^{30}=-9°$ (c=0.27; DMSO).

EXAMPLE 249

5-(4-Methyl-3-pyridinyl)-3-pyridinyl 5-thio-β-D-xylopyranoside

By carrying out the operation analogously to example 2, starting from the product prepared according to example 248, the desired product is obtained in the form of a white solid (yield=49%).
M.p.=201° C.
$[\alpha]_D^{26}=-75°$ (c=0.23; DMSO).

EXAMPLE 250

2,6-Di(4-fluoro-3-pyridinyl)-3-pyridinyl 2,3,4-tri-O-acetyl-5-thio-β-D-xylo-pyranoside By carrying out the operation analogously to example 1, starting from 2-chloro-6-iodo-3-pyridinyl 2,3,4-tri-O-acetyl-5-thio-β-D-xylopyranoside, obtained according to preparation X, and 6-fluoro-3-pyridineboronic acid, the desired product is obtained in the form of a beige powder (yield=15%).
M.p.=169° C.
$[\alpha]_D^{26}=-35°$ (c=0.45; DMSO).

EXAMPLE 251

2,6-Di(4-fluoro-3-pyridinyl)-3-pyridinyl 5-thio-β-D-xylopyranoside

By carrying out the operation analogously to example 2, starting from the product prepared according to example 250, the desired product is obtained in the form of a beige powder (yield=30%).
M.p.=209° C. (recrystallized from an ethanol/water mixture).
$[\alpha]_D^{26}=-19°$ (c=0.14; DMSO).

EXAMPLE 252

2-(5-Tetrazolyl)-3-pyridinyl 2,3,4-tri-O-acetyl-5-thio-β-D-xylopyranoside

A mixture of 0.682 g (1.73 mM) of 2-cyano-3-pyridinyl 2,3,4-tri-O-acetyl-5-thio-β-D-xylopyranoside, obtained according to preparation XV, and 1.24 g (6.05 mM) of azidotrimethyltin in 10 ml of toluene is prepared and this mixture is stirred at 70° C. for 7 days. After cooling, the reaction medium is poured onto a mixture of water and ethyl acetate and brought to pH 1 by addition of an N hydrochloric acid solution. The aqueous phase is extracted, brought to pH 5 by addition of a dilute sodium hydroxide solution and extracted with ethyl acetate. This organic phase is separated, washed with water, dried over magnesium sulfate and concentrated under reduced pressure. The crude product obtained is purified by chromatography on silica gel, elution being carried out with a dichloromethane/methanol mixture (95/5;v/v). The expected compound is thus obtained in the form of a white foam (yield=30%).
M.p.=119-127° C.
$[\alpha]_D^{25}=-147°$ (c=0.28; CH$_2$Cl$_2$).

EXAMPLE 253

2-(5-Tetrazolyl)-3-pyridinyl 5-thio-β-D-xylopyranoside

By carrying out the operation analogously to example 42, starting from the product prepared according to example 252, the desired product is obtained in the form of a white powder (yield=42%).
M.p.=170° C. (recrystallized from an ethanol/water mixture).
$[\alpha]_D^{22}=-153°$ (c=0.24; DMSO).

EXAMPLE 254

6-(3,5-Dimethyl-4-isoxazolyl)-2-fluoro-3-pyridinyl 2,3,4-tri-O-acetyl-5-thio-β-D-xylopyranoside By carrying out the operation analogously to example 213, starting from 2-fluoro-6-iodo-3-pyridinyl 2,3,4-tri-O-acetyl-5-thio-β-D-xylopyranoside, obtained according to preparation XII, and 3,5-dimethyl-4-isoxazoleboronic acid, the desired product is obtained and is used directly in the deacetylation stage.

EXAMPLE 255

6-(3,5-Dimethyl-4-isoxazolyl)-2-fluoro-3-pyridinyl 5-thio-β-D-xylopyranoside By carrying out the operation analogously to example 2, starting from the product prepared according to example 254, the desired product is obtained in the form of a white powder (yield=56%).
M.p.=101-104° C.
$[\alpha]_D^{32}=-42°$ (c=0.12; DMSO).

EXAMPLE 256

2-Fluoro-6-(2-fluoro-3-pyridinyl)-3-pyridinyl 2,3,4-tri-O-acetyl-5-thio-β-D-xylopyranoside By carrying out the operation analogously to example 254, starting from 2-fluoro-3-pyridineboronic acid, the desired product is obtained and is used directly in the deacetylation stage.

EXAMPLE 257

2-Fluoro-6-(2-fluoro-3-pyridinyl)-3-pyridinyl 5-thio-β-D-xylopyranoside

By carrying out the operation analogously to example 2, starting from the product prepared according to example 256, the desired product is obtained in the form of a white powder (yield=53%).
M.p.=186-190° C.
$[\alpha]_D^{32}=-33°$ (c=0.12; DMSO).

EXAMPLE 258

2-Fluoro-6-(5-pyrimidinyl)-3-pyridinyl 2,3,4-tri-O-acetyl-5-thio-β-D-xylo-pyranoside By carrying out the operation analogously to example 254, starting from 5-pyrimidineboronic acid, the desired product is obtained and is used directly in the deacetylation stage.

EXAMPLE 259

2-Fluoro-6-(5-pyrimidinyl)-3-pyridinyl 5-thio-β-D-xylopyranoside

By carrying out the operation analogously to example 2, starting from the product prepared according to example 258, the desired product is obtained in the form of a white powder (yield=33%).
M.p.=177-179° C.
$[\alpha]_D^{32}$=−106° (c=0.45; DMSO).

EXAMPLE 260

2-Fluoro-6-(6-fluoro-3-pyridinyl)-3-pyridinyl 2,3,4-tri-O-acetyl-5-thio-β-D-xylopyranoside By carrying out the operation analogously to example 254, starting from 6-fluoro-3-pyridineboronic acid, the desired product is obtained and is used directly in the deacetylation stage.

EXAMPLE 261

2-Fluoro-6-(6-fluoro-3-pyridinyl)-3-pyridinyl 5-thio-β-D-xylopyranoside

By carrying out the operation analogously to example 2, starting from the product prepared according to example 260, the desired product is obtained in the form of a white powder (yield=65%).
M.p.=141-144° C.
$[\alpha]_D^{32}$=−38° (c=0.26; DMSO).

EXAMPLE 262

2-Fluoro-6-(2-fluoro-4-pyridinyl)-3-pyridinyl 2,3,4-tri-O-acetyl-5-thio-β-D-xylopyranoside By carrying out the operation analogously to example 254, starting from 2-fluoro-4-pyridineboronic acid, the desired product is obtained and is used directly in the deacetylation stage.

EXAMPLE 263

2-Fluoro-6-(2-fluoro-4-pyridinyl)-3-pyridinyl 5-thio-β-D-xylopyranoside

By carrying out the operation analogously to example 2, starting from the product prepared according to example 262, the desired product is obtained in the form of a white powder (yield=53%).
M.p.=179-182° C.
$[\alpha]_D^{32}$=−37° (c=0.10; DMSO).

EXAMPLE 264

2-Fluoro-6-(1-methyl-1H-pyrazol-4-yl)-3-pyridinyl 2,3,4-tri-O-acetyl-5-thio-β-D-xylopyranoside By carrying out the operation analogously to example 254, starting from 1-methyl-4-(pinacolatoboryl)-1H-pyrazole, the desired product is obtained and is used directly in the deacetylation stage.

EXAMPLE 265

2-Fluoro-6-(1-methyl-1H-pyrazol-4-yl)-3-pyridinyl 5-thio-β-D-xylopyranoside

By carrying out the operation analogously to example 2, starting from the product prepared according to example 264, the desired product is obtained in the form of a white solid (yield=38%).
M.p.=183-185° C.
$[\alpha]_D^{32}$=−23° (c=0.13; DMSO).

EXAMPLE 266

2-Fluoro-6-(6-methyl-3-pyridinyl)-3-pyridinyl 2,3,4-tri-O-acetyl-5-thio-β-D-xylopyranoside By carrying out the operation analogously to example 254, starting from 6-methyl-3-pyridineboronic acid, the desired product is obtained and is used directly in the deacetylation stage.

EXAMPLE 267

2-Fluoro-6-(6-methyl-3-pyridinyl)-3-pyridinyl 5-thio-β-D-xylopyranoside

By carrying out the operation analogously to example 2, starting from the product prepared according to example 266, the desired product is obtained in the form of a pink powder (yield=36%).
M.p.=189-190° C.
$[\alpha]_D^{32}$=−20° (c=0.10; DMSO).

EXAMPLE 268

2-Fluoro-6-(2-methyl-4-pyridinyl)-3-pyridinyl 2,3,4-tri-O-acetyl-5-thio-β-D-xylopyranoside By carrying out the operation analogously to example 254, starting from 2-methyl-4-pyridineboronic acid, the desired product is obtained and is used directly in the deacetylation stage.

EXAMPLE 269

2-Fluoro-6-(2-methyl-4-pyridinyl)-3-pyridinyl 5-thio-β-D-xylopyranoside

By carrying out the operation analogously to example 2, starting from the product prepared according to example 268, the desired product is obtained in the form of a white powder (yield=24%).
M.p.=159-162° C.
$[\alpha]_D^{32}$=−23° (c=0.10; DMSO).

EXAMPLE 270

2-Fluoro-6-(6-cyano-3-pyridinyl)-3-pyridinyl 2,3,4-tri-O-acetyl-5-thio-β-D-xylopyranoside By carrying out the operation analogously to example 254, starting from 2-cyano-5-(pinacolatoboryl)pyridine, the desired product is obtained and is used directly in the deacetylation stage.

EXAMPLE 271

2-Fluoro-6-(6-cyano-3-pyridinyl)-3-pyridinyl 5-thio-β-D-xylopyranoside

By carrying out the operation analogously to example 2, starting from the product prepared according to example 270, the desired product is obtained in the form of a white powder (yield=37%).
M.p.=158-162° C.
$[\alpha]_D^{32}=-19°$ (c=0.14; DMSO).

EXAMPLE 272

5-Fluoro-6-(3-pyridinyl)-3-pyridinyl 2,3,4-tri-O-acetyl-5-thio-β-D-xylo-pyranoside By carrying out the operation analogously to example 213, starting from 6-chloro-5-fluoro-3-pyridinyl 2,3,4-tri-O-acetyl-5-thio-β-D-xylopyranoside, obtained according to preparation XI, and 3-pyridineboronic acid, the desired product is obtained and is used directly in the deacetylation stage.

EXAMPLE 273

5-Fluoro-6-(3-pyridinyl)-3-pyridinyl 5-thio-β-D-xylopyranoside

By carrying out the operation analogously to example 2, starting from the product prepared according to example 272, the desired product is obtained in the form of a white powder (yield=58%).
M.p.=179° C.
$[\alpha]_D^{32}=-33°$ (c=0.10; DMSO).

EXAMPLE 274

5-Fluoro-6-(2-fluoro-4-pyridinyl)-3-pyridinyl 2,3,4-tri-O-acetyl-5-thio-β-D-xylopyranoside By carrying out the operation analogously to example 272, starting from 2-fluoro-4-pyridineboronic acid, the desired product is obtained and is used directly in the deacetylation stage.

EXAMPLE 275

5-Fluoro-6-(2-fluoro-4-pyridinyl)-3-pyridinyl 5-thio-β-D-xylopyranoside

By carrying out the operation analogously to example 2, starting from the product prepared according to example 274, the desired product is obtained in the form of a white powder (yield=53%).
M.p.=209-212° C.
$[\alpha]_D^{27}=-68°$ (c=0.10; DMSO).

EXAMPLE 276

2-Chloro-5-(5-pyrimidinyl)-3-pyridinyl 2,3,4-tri-O-acetyl-5-thio-β-D-xylo-pyranoside By carrying out the operation analogously to example 259, starting from 5-bromo-2-chloro-3-pyridinyl 2,3,4-tri-O-acetyl-5-thio-β-D-xylopyranoside, obtained according to preparation XIV, the expected product is obtained in the form of a white foam (yield=48%).
M.p.=72-90° C.
$[\alpha]_D^{25}=-44°$ (c=0.21; DMSO).

EXAMPLE 277

2-Chloro-5-(5-pyrimidinyl)-3-pyridinyl 5-thio-β-D-xylopyranoside

By carrying out the operation analogously to example 2, starting from the product prepared according to example 276, the desired product is obtained in the form of white flakes (yield=81%).
M.p.=174-189° C.
$[\alpha]_D^{25}=60°$ (c=0.22; DMSO).

EXAMPLE 278

2-Chloro-5-(6-fluoro-3-pyridinyl)-3-pyridinyl 2,3,4-tri-O-acetyl-5-thio-β-D-xylopyranoside By carrying out the operation analogously to example 276, starting from 6-fluoro-3-pyridineboronic acid, the expected product is obtained in the form of a white foam (yield=38%).
M.p.=70-90° C.
$[\alpha]_D^{24}=-26°$ (c=0.22; DMSO).

EXAMPLE 279

2-Chloro-5-(6-fluoro-3-pyridinyl)-3-pyridinyl 5-thio-β-D-xylopyranoside

By carrying out the operation analogously to example 2, starting from the product prepared according to example 278, the desired product is obtained in the form of white flakes (yield=84%).
M.p.=176-197° C.
$[\alpha]_D^{30}=-51°$ (c=0.15; DMSO).

EXAMPLE 280

2-Chloro-6-(5-pyrimidinyl)-3-pyridinyl 2,3,4-tri-O-acetyl-5-thio-β-D-xylo-pyranoside By carrying out the operation analogously to example 259, starting from 2-chloro-6-iodo-3-pyridinyl 2,3,4-tri-O-acetyl-5-thio-β-D-xylopyranoside, obtained according to preparation X, the expected product is obtained in the form of a white foam (yield=37%).
M.p.=168° C.
$[\alpha]_D^{36}=-41°$ (c=0.11; DMSO).

EXAMPLE 281

2-Chloro-6-(5-pyrimidinyl)-3-pyridinyl 5-thio-β-D-xylopyranoside

By carrying out the operation analogously to example 2, starting from the product prepared according to example 280, the desired product is obtained in the form of a white powder (yield=20%).
M.p.=100° C.
$[\alpha]_D^{26}=31°$ (c=0.11; DMSO).

EXAMPLE 282

2-Fluoro-5-(2-pyridinyl)-3-pyridinyl 2,3,4-tri-O-acetyl-5-thio-β-D-xylo-pyranoside By carrying out the operation analogously to example 231, starting from 5-bromo-2-fluoro-3-pyridinyl 2,3,4-tri-O-acetyl-5-thio-β-D-xylopyranoside, obtained according to preparation VIII, and 2-bromopyridine, the desired product is obtained and is used directly in the deacetylation stage.

EXAMPLE 283

2-Fluoro-5-(2-pyridinyl)-3-pyridinyl 5-thio-β-D-xylopyranoside

By carrying out the operation analogously to example 2, starting from the product prepared according to example 282, the desired product is obtained in the form of a white solid (yield=79%).
M.p.=145-146° C.

EXAMPLE 284

2-Fluoro-5-(5-pyrimidinyl)-3-pyridinyl 2,3,4-tri-O-acetyl-5-thio-β-D-xylo-pyranoside By carrying out the operation analogously to the first part of example 137, 5-(pinacolatoboryl)pyrimidine is prepared from 5-bromopyrimidine and is reacted immediately in the same reactor with 5-bromo-2-fluoro-3-pyridinyl 2,3,4-tri-O-acetyl-5-thio-β-D-xylopyranoside, obtained according to preparation VIII, under conditions analogous to those applied in the preparation of example 177. The expected product is thus obtained in the form of a yellow solid (yield=40%).
M.p.=96-97° C.
$[\alpha]_D^{30}=-11°$ (c=0.24; DMSO).

EXAMPLE 285

2-Fluoro-5-(5-pyrimidinyl)-3-pyridinyl 5-thio-β-D-xylopyranoside

By carrying out the operation analogously to example 2, starting from the product prepared according to example 284, the desired product is obtained in the form of a white solid (yield=60%).
M.p.=204-205° C.

The structures of the compounds of formula I described in the preceding examples have been combined in the following table:

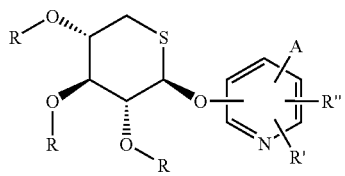

with A =

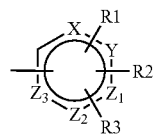

| Ex. | Pos-N | R' | R" | Pos-A | X | Y | Z1 | Z2 | Z3 | R1 | R2 | R3 | R |
|---|---|---|---|---|---|---|---|---|---|---|---|---|---|
| 1 | 3 | H | H | 6 | 3-N | C | C | C | C | 2-OCH₃ | H | H | Ac |
| 2 | 3 | H | H | 6 | 3-N | C | C | C | C | 2-OCH₃ | H | H | H |
| 3 | 3 | 4-CH₃ | H | 2 | 3-N | C | C | C | C | H | H | H | Ac |
| 4 | 3 | 4-CH₃ | H | 2 | 3-N | C | C | C | C | H | H | H | H |
| 5 | 3 | 6-CH₃ | H | 2 | 3-O | sb | C | C | C | H | H | H | Ac |
| 6 | 3 | 6-CH₃ | H | 2 | 3-O | ab | C | C | C | H | H | H | H |
| 7 | 3 | H | H | 2 | 2-O | sb | C | C | C | 5-CH₃ | H | H | Ac |
| 8 | 3 | H | H | 2 | 2-O | sb | C | C | C | 5-CH₃ | H | H | H |
| 9 | 3 | 2-Cl | H | 6 | 3-N | C | C | C | C | H | H | H | Ac |
| 10 | 3 | 2-Cl | H | 6 | 3-N | C | C | C | C | H | H | H | H |
| 11 | 3 | 2-F | H | 5 | 4-N | C | C | C | C | H | H | H | Ac |
| 12 | 3 | 2-F | H | 5 | 4-N | C | C | C | C | H | H | H | H |
| 13 | 3 | 2-Cl | H | 6 | 3-N | C | C | C | C | 2-OCH₃ | H | H | Ac |
| 14 | 3 | 2-Cl | H | 6 | 3-N | C | C | C | C | 2-OCH₃ | H | H | H |
| 15 | 3 | 2-Cl | H | 6 | 3-N | C | C | C | C | 2-F | H | H | Ac |
| 16 | 3 | 2-Cl | H | 6 | 3-N | C | C | C | C | 2-F | H | H | H |

-continued

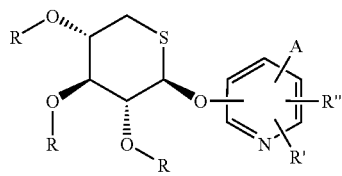

with A =

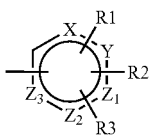

| Ex. | Pos-N | R' | R" | Pos-A | X | Y | Z1 | Z2 | Z3 | R₁ | R₂ | R₃ | R |
|---|---|---|---|---|---|---|---|---|---|---|---|---|---|
| 17 | 3 | 2-Cl | H | 6 | 4-N | C | C | C | C | 2-F | H | H | Ac |
| 18 | 3 | 2-Cl | H | 6 | 4-N | C | C | C | C | 2-F | H | H | H |
| 19 | 3 | 2-Cl | H | 6 | 3-N | C | C | C | C | 6-F | H | H | Ac |
| 20 | 3 | 2-Cl | H | 6 | 3-N | C | C | C | C | 6-F | H | H | H |
| 21 | 3 | 2-F | H | 6 | 4-N | C | C | C | C | H | H | H | Ac |
| 22 | 3 | 2-F | H | 6 | 4-N | C | C | C | C | H | H | H | H |
| 23 | 3 | 2-Cl | H | 6 | 4-N | C | C | C | C | H | H | H | Ac |
| 24 | 3 | 2-Cl | H | 6 | 4-N | C | C | C | C | H | H | H | H |
| 25 | 3 | H | H | 5 | 3-N | C | C | C | C | 2-Cl | H | H | Ac |
| 26 | 3 | H | H | 5 | 3-N | C | C | C | C | 2-Cl | H | H | H |
| 27 | 3 | H | H | 5 | 3-N | C | C | C | C | 6-OCH₃ | H | H | Ac |
| 28 | 3 | H | H | 5 | 3-N | C | C | C | C | 6-OCH₃ | H | H | H |
| 29 | 3 | H | H | 5 | 3-N | C | C | C | C | 6-Cl | H | H | Ac |
| 30 | 3 | H | H | 5 | 3-N | C | C | C | C | 6-Cl | H | H | H |
| 31 | 3 | H | H | 5 | 3-N | C | C | C | C | 2-OCH₃ | H | H | Ac |
| 32 | 3 | H | H | 5 | 3-N | C | C | C | C | 2-OCH₃ | H | H | H |
| 33 | 3 | H | H | 6 | 2-O | sb | C | C | C | 5-CH₃ | H | H | Ac |
| 34 | 3 | H | H | 6 | 2-O | sb | C | C | C | 5-CH₃ | H | H | H |
| 35 | 3 | H | H | 6 | 3-N | C | C | C | C | 6-CH₃ | H | H | Ac |
| 36 | 3 | H | H | 6 | 3-N | C | C | C | C | 6-CH₃ | H | H | H |
| 37 | 3 | H | H | 6 | 3-N | C | C | C | C | 6-Cl | H | H | Ac |
| 38 | 3 | H | H | 6 | 3-N | C | C | C | C | 6-Cl | H | H | H |
| 39 | 3 | H | H | 6 | 3-N | C | C | C | C | 2-Cl | H | H | Ac |
| 40 | 3 | H | H | 6 | 3-N | C | C | C | C | 2-Cl | H | H | H |
| 41 | 3 | 5-Cl | H | 6 | 4-N | C | C | C | C | H | H | H | Ac |
| 42 | 3 | 5-Cl | H | 6 | 4-N | C | C | C | C | H | H | H | H |
| 43 | 3 | 5-F | H | 6 | 4-N | C | C | C | C | H | H | H | Ac |
| 44 | 3 | 5-F | H | 6 | 4-N | C | C | C | C | H | H | H | H |
| 45 | 2 | H | H | 6 | 4-N | C | C | C | C | H | H | H | Ac |
| 46 | 2 | H | H | 6 | 4-N | C | C | C | C | H | H | H | H |
| 47 | 2 | H | H | 6 | 3-N | C | C | C | C | H | H | H | Ac |
| 48 | 2 | H | H | 6 | 3-N | C | C | C | C | H | H | H | H |
| 49 | 3 | H | H | 5 | 2-N | C | C | C | C | 5-F | H | H | Ac |
| 50 | 3 | H | H | 5 | 2-N | C | C | C | C | 5-F | H | H | H |
| 51 | 3 | 2-F | H | 5 | 3-N | C | C | C | C | H | H | H | Ac |
| 52 | 3 | 2-F | H | 5 | 3-N | C | C | C | C | H | H | H | H |
| 53 | 3 | H | H | 5 | 4-N | C | C | C | C | 3-CH₃ | H | H | Ac |
| 54 | 3 | H | H | 5 | 4-N | C | C | C | C | 3-CH₃ | H | H | H |
| 55 | 3 | H | H | 5 | 2-N | C | C | C | C | 3-CH₃ | H | H | Ac |
| 56 | 3 | H | H | 5 | 2-N | C | C | C | C | 3-CH₃ | H | H | H |
| 57 | 3 | H | H | 5 | 5-S | sb | C | N | C | 2-CH₃ | 4-CH₃ | — | Ac |
| 58 | 3 | H | H | 5 | 5-S | sb | C | N | C | 2-CH₃ | 4-CH₃ | — | H |
| 59 | 3 | H | H | 5 | 4-N | sb | N | C | C | 1-CH₃ | 3-CF₃ | H | Ac |
| 60 | 3 | H | H | 5 | 4-N | sb | N | C | C | 1-CH₃ | 3-CF₃ | H | H |
| 61 | 3 | H | H | 5 | 4-N | sb | N | C | C | 5-CH₃ | 3-CF₃ | H | Ac |
| 62 | 3 | H | H | 5 | 4-N | sb | N | C | C | 5-CH₃ | 3-CF₃ | H | H |
| 63 | 3 | H | H | 5 | 4-O | sb | N | C | C | 5-CH₃ | H | — | Ac |
| 64 | 3 | H | H | 5 | 4-O | sb | N | C | C | 5-CH₃ | H | — | H |
| 65 | 3 | H | H | 5 | 2-N | C | C | N | C | H | H | H | Ac |
| 66 | 3 | H | H | 5 | 2-N | C | C | N | C | H | H | H | H |
| 67 | 3 | H | H | 5 | 2-N | C | C | N | C | H | H | H | Ac |
| 68 | 3 | H | H | 5 | 2-N | C | N | C | C | H | H | H | H |
| 69 | 3 | H | H | 5 | 2-S | sb | C | N | C | H | H | — | Ac |
| 70 | 3 | H | H | 5 | 2-S | sb | C | N | C | H | H | — | H |
| 71 | 3 | H | H | 5 | 5-N | sb | C | N | C | 1-CH₃ | H | H | Ac |
| 72 | 3 | H | H | 5 | 5-N | sb | C | N | C | 1-CH₃ | H | H | H |
| 73 | 3 | H | H | 5 | 4-N | C | C | C | C | 2-Cl | H | H | Ac |

-continued

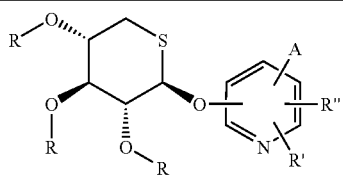

with A =

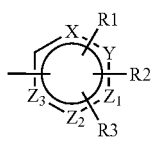

| Ex. | Pos-N | R' | R" | Pos-A | X | Y | Z1 | Z2 | Z3 | R₁ | R₂ | R₃ | R |
|---|---|---|---|---|---|---|---|---|---|---|---|---|---|
| 74 | 3 | H | H | 5 | 4-N | C | C | C | C | 2-Cl | H | H | H |
| 75 | 3 | H | H | 5 | 4-N | C | C | C | C | 3-Cl | H | H | Ac |
| 76 | 3 | H | H | 5 | 4-N | C | C | C | C | 3-Cl | H | H | H |
| 77 | 3 | H | H | 6 | 3-N | C | C | C | C | 6-OCH₃ | H | H | Ac |
| 78 | 3 | H | H | 6 | 3-N | C | C | C | C | 6-OCH₃ | H | H | H |
| 79 | 3 | 4-CH₃ | H | 2 | 3-O | sb | C | C | C | H | H | H | Ac |
| 80 | 3 | 4-CH₃ | H | 2 | 3-O | sb | C | C | C | H | H | H | H |
| 81 | 3 | 4-CH₃ | H | 2 | 4-O | sb | N | C | C | 3-CH₃ | 5-CH₃ | — | Ac |
| 82 | 3 | 4-CH₃ | H | 2 | 4-O | sb | N | C | C | 3-CH₃ | 5-CH₃ | — | H |
| 83 | 3 | H | H | 4 | 3-N | C | C | C | C | H | H | H | Ac |
| 84 | 3 | H | H | 4 | 3-N | C | C | C | C | H | H | H | H |
| 85 | 3 | H | H | 2 | benzofuran | | | | | | | H | Ac |
| 86 | 3 | H | H | 2 | benzofuran | | | | | | | H | H |
| 87 | 3 | H | H | 4 | 3-O | sb | C | C | C | H | H | H | Ac |
| 88 | 3 | H | H | 4 | 3-O | sb | C | C | C | H | H | H | H |
| 89 | 3 | H | H | 4 | 4-N | C | C | C | C | H | H | H | Ac |
| 90 | 3 | H | H | 4 | 4-N | C | C | C | C | H | H | H | H |
| 91 | 3 | H | H | 5 | benzothiophene | | | | | | | H | Ac |
| 92 | 3 | H | H | 5 | benzothiophene | | | | | | | H | H |
| 93 | 3 | H | H | 2 | 2-S | sb | C | C | C | H | H | H | Ac |
| 94 | 3 | H | H | 2 | 2-S | sb | C | C | C | H | H | H | H |
| 95 | 3 | H | H | 5 | 2-O | sb | C | C | C | 5-CH₃ | H | H | Ac |
| 96 | 3 | H | H | 5 | 2-O | sb | C | C | C | 5-CH₃ | H | H | H |
| 97 | 3 | H | H | 6 | benzofuran | | | | | | | H | Ac |
| 98 | 3 | H | H | 6 | benzofuran | | | | | | | H | H |
| 99 | 3 | H | H | 6 | 3-S | sb | C | C | C | H | H | H | Ac |
| 100 | 3 | H | H | 6 | 3-S | sb | C | C | C | H | H | H | H |

-continued

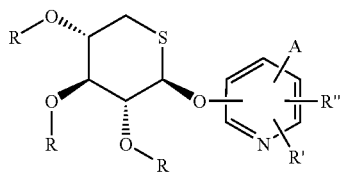

with A =

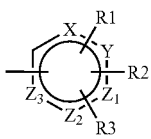

| Ex. | Pos-N | R' | R" | Pos-A | X | Y | Z1 | Z2 | Z3 | R₁ | R₂ | R₃ | R |
|---|---|---|---|---|---|---|---|---|---|---|---|---|---|
| 101 | 3 | H | H | 2 | 2-O | sb | C | C | C | H | H | H | Ac |
| 102 | 3 | H | H | 2 | 2-O | sb | C | C | C | H | H | H | H |
| 103 | 3 | H | H | 6 | 2-O | sb | C | C | C | H | H | H | Ac |
| 104 | 3 | H | H | 6 | 2-O | sb | C | C | C | H | H | H | H |
| 105 | 3 | H | H | 6 | 2-O | C | C | C | C | H | H | H | Ac |
| 106 | 3 | H | H | 2 | 4-N | C | C | C | C | H | H | H | H |
| 107 | 3 | H | H | 6 | 2-S | sb | C | C | C | H | H | H | Ac |
| 108 | 3 | H | H | 6 | 2-S | sb | C | C | C | H | H | H | H |
| 109 | 3 | H | H | 5 | 2-O | sb | C | C | C | H | H | H | Ac |
| 110 | 3 | H | H | 5 | 2-O | sb | C | C | C | H | H | H | H |
| 111 | 3 | H | H | 2 | 3-N | C | C | C | C | H | H | H | Ac |
| 112 | 3 | H | H | 2 | 3-N | C | C | C | C | H | H | H | H |
| 113 | 3 | H | H | 2 | 3-O | sb | C | C | C | H | H | H | Ac |
| 114 | 3 | H | H | 2 | 3-O | sb | C | C | C | H | H | H | H |
| 115 | 3 | H | H | 5 | benzofuran | | | | | | | H | Ac |
| 116 | 3 | H | H | 5 | benzofuran | | | | | | | H | H |
| 117 | 3 | H | H | 6 | 3-O | sb | C | C | C | H | H | H | Ac |
| 118 | 3 | H | H | 6 | 3-O | sb | C | C | C | H | H | H | H |
| 119 | 3 | H | H | 6 | 3-N | C | C | C | C | H | H | H | Ac |
| 120 | 3 | H | H | 6 | 3-N | C | C | C | C | H | H | H | H |
| 121 | 3 | H | H | 6 | 4-N | C | C | C | C | H | H | H | Ac |
| 122 | 3 | H | H | 6 | 4-N | C | C | C | C | H | H | H | H |
| 123 | 3 | H | H | 5 | 4-N | C | C | C | C | H | H | H | Ac |
| 124 | 3 | H | H | 5 | 4-N | C | C | C | C | H | H | H | H |
| 125 | 3 | H | H | 5 | 3-O | sb | C | C | C | H | H | H | Ac |
| 126 | 3 | H | H | 5 | 3-O | sb | C | C | C | H | H | H | H |
| 127 | 3 | H | H | 5 | 3-N | C | C | C | C | H | H | H | Ac |
| 128 | 3 | H | H | 5 | 3-N | C | C | C | C | H | H | H | H |
| 129 | 4 | H | H | 2 | 4-N | C | C | C | C | H | H | H | Ac |
| 130 | 4 | H | H | 2 | 4-N | C | C | C | C | H | H | H | H |
| 131 | 4 | H | H | 2 | 3-N | C | C | C | C | 6-F | H | H | Ac |
| 132 | 4 | H | H | 2 | 3-N | C | C | C | C | 6-F | H | H | Ac |
| 133 | 4 | H | H | 2 | 3-N | C | C | C | C | H | H | H | Ac |
| 134 | 4 | H | H | 2 | 3-N | C | C | C | C | H | H | H | H |
| 135 | 3 | H | H | 5 | 2-S | sb | C | C | C | H | H | H | Ac |
| 136 | 3 | H | H | 5 | 2-S | sb | C | C | C | H | H | H | H |
| 137 | 3 | H | H | 5 | 3-N | C | C | C | C | 5-OCH₃ | H | H | Ac |
| 138 | 3 | H | H | 5 | 3-N | C | C | C | C | 5-OCH₃ | H | H | H |
| 139 | 3 | H | H | 6 | 4-O | sb | N | C | C | 5-CH₃ | H | — | Ac |
| 140 | 3 | H | H | 6 | 4-O | sb | N | C | C | 5-CH₃ | H | — | H |
| 141 | 3 | H | H | 6 | 3-N | C | C | C | C | 5-CH₃ | H | H | Ac |
| 142 | 3 | H | H | 6 | 3-N | C | C | C | C | 5-CH₃ | H | H | H |
| 143 | 3 | H | H | 5 | 3-N | C | C | C | C | 5-CH₃ | H | H | Ac |
| 144 | 3 | H | H | 5 | 3-N | C | C | C | C | 5-CH₃ | H | H | H |
| 145 | 3 | H | H | 5 | 3-N | C | C | C | C | 5-Cl | H | H | Ac |
| 146 | 3 | H | H | 5 | 3-N | C | C | C | C | 5-Cl | H | H | H |
| 147 | 3 | H | H | 5 | 3-N | C | C | C | C | 6-CN | H | H | Ac |

-continued

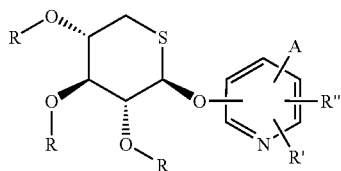

with A =

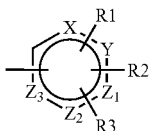

| Ex. | Pos-N | R' | R" | Pos-A | X | Y | Z1 | Z2 | Z3 | A R₁ | R₂ | R₃ | R |
|---|---|---|---|---|---|---|---|---|---|---|---|---|---|
| 148 | 3 | H | H | 5 | 3-N | C | C | C | C | 6-CN | H | H | H |
| 149 | 3 | H | H | 6 | 3-N | C | C | C | C | 5-F | H | H | Ac |
| 150 | 3 | H | H | 6 | 3-N | C | C | C | C | 5-F | H | H | H |
| 151 | 3 | H | H | 5 | 3-N | C | C | C | C | 2-CH₃ | H | H | Ac |
| 152 | 3 | H | H | 5 | 3-N | C | C | C | C | 2-CH₃ | H | H | H |
| 153 | 3 | H | H | 5 | 3-N | C | C | C | C | 5-F | H | H | Ac |
| 154 | 3 | H | H | 5 | 3-N | C | C | C | C | 5-F | H | H | H |
| 155 | 3 | H | H | 6 | 3-N | C | C | C | C | 5-OCH₃ | H | H | Ac |
| 156 | 3 | H | H | 6 | 3-N | C | C | C | C | 5-OCH₃ | H | H | H |
| 157 | 3 | H | H | 5 | 4-N | sb | N | C | C | 1-CH₃ | 3-CH₃ | 5-CH₃ | Ac |
| 158 | 3 | H | H | 5 | 4-N | sb | N | C | C | 1-CH₃ | 3-CH₃ | 5-CH₃ | H |
| 159 | 3 | H | H | 5 | 4-N | sb | N | C | C | 3-CH₃ | 5-CH₃ | H | Ac |
| 160 | 3 | H | H | 5 | 4-N | sb | N | C | C | 3-CH₃ | 5-CH₃ | H | H |
| 161 | 3 | H | H | 6 | 3-N | C | C | C | C | 6-CN | H | H | Ac |
| 162 | 3 | H | H | 6 | 3-N | C | C | C | C | 6-CN | H | H | H |
| 163 | 3 | H | H | 6 | 4-N | sb | N | C | C | 1-CH₃ | 3-CH₃ | 5-CH₃ | Ac |
| 164 | 3 | H | H | 6 | 4-N | sb | N | C | C | 1-CH₃ | 3-CH₃ | 5-CH₃ | H |
| 165 | 3 | H | H | 6 | 4-N | sb | N | C | C | 1-CH₃ | H | H | Ac |
| 166 | 3 | H | H | 6 | 4-N | sb | N | C | C | 1-CH₃ | H | H | H |
| 167 | 3 | H | H | 6 | 4-N | sb | N | C | C | 3-CH₃ | 5-CH₃ | H | Ac |
| 168 | 3 | H | H | 6 | 4-N | sb | N | C | C | 3-CH₃ | 5-CH₃ | H | H |
| 169 | 3 | H | H | 5 | 3-N | C | C | C | C | 6-F | H | H | Ac |
| 170 | 3 | H | H | 5 | 3-N | C | C | C | C | 6-F | H | H | H |
| 171 | 3 | H | H | 5 | 4-N | sb | N | C | C | 1-CH₃ | H | H | Ac |
| 172 | 3 | H | H | 5 | 4-N | sb | N | C | C | 1-CH₃ | H | H | H |
| 173 | 3 | H | H | 6 | 5-S | sb | C | N | C | 2-CH₃ | 4-CH₃ | — | Ac |
| 174 | 3 | H | H | 6 | 5-S | sb | C | N | C | 2-CH₃ | 4-CH₃ | — | H |
| 175 | 3 | H | H | 6 | 3-N | C | C | C | C | 2-CH₃ | H | H | Ac |
| 176 | 3 | H | H | 6 | 3-N | C | C | C | C | 2-CH₃ | H | H | H |
| 177 | 3 | H | H | 5 | 5-N | C | N | C | C | H | H | H | Ac |
| 178 | 3 | H | H | 5 | 5-N | C | N | C | C | H | H | H | H |
| 179 | 3 | H | H | 5 | 4-O | sb | N | C | C | 3-CH₃ | 5-CH₃ | — | Ac |
| 180 | 3 | H | H | 5 | 4-O | sb | N | C | C | 3-CH₃ | 5-CH₃ | — | H |
| 181 | 3 | H | H | 2 | 4-O | sb | N | C | C | 3-CH₃ | 5-CH₃ | — | Ac |
| 182 | 3 | H | H | 2 | 4-O | sb | N | C | C | 3-CH₃ | 5-CH₃ | — | H |
| 183 | 3 | H | H | 5 | 3-N | C | C | C | C | 2-F | H | H | Ac |
| 184 | 3 | H | H | 5 | 3-N | C | C | C | C | 2-F | H | H | H |
| 185 | 3 | H | H | 5 | 4-N | C | C | C | C | 2-F | H | H | Ac |
| 186 | 3 | H | H | 5 | 4-N | C | C | C | C | 2-F | H | H | H |
| 187 | 3 | H | H | 6 | 3-N | C | C | C | C | 2-F | H | H | Ac |
| 188 | 3 | H | H | 6 | 3-N | C | C | C | C | 2-F | H | H | H |
| 189 | 3 | H | H | 6 | 5-N | C | N | C | C | H | H | H | Ac |
| 190 | 3 | H | H | 6 | 5-N | C | N | C | C | H | H | H | H |
| 191 | 3 | H | H | 6 | 4-O | sb | N | C | C | 3-CH₃ | 5-CH₃ | — | Ac |
| 192 | 3 | H | H | 6 | 4-O | sb | N | C | C | 3-CH₃ | 5-CH₃ | — | H |
| 193 | 3 | H | H | 6 | 3-N | C | C | C | C | 6-F | H | H | Ac |
| 194 | 3 | H | H | 6 | 3-N | C | C | C | C | 6-F | H | H | H |
| 195 | 3 | 2-F | H | 5 | 4-N | C | C | C | C | 2-F | H | H | Ac |
| 196 | 3 | 2-F | H | 5 | 4-N | C | C | C | C | 2-F | H | H | H |
| 197 | 3 | 2-F | H | 5 | 3-N | C | C | C | C | 6-F | H | H | Ac |
| 198 | 3 | 2-F | H | 5 | 3-N | C | C | C | C | 6-F | H | H | H |
| 199 | 3 | H | H | 5 | 3-S | sb | C | C | C | H | H | H | Ac |
| 200 | 3 | H | H | 5 | 3-S | sb | C | C | C | H | H | H | H |
| 201 | 3 | H | H | 6 | 4-N | C | C | C | C | 2-Cl | H | H | Ac |
| 202 | 3 | H | H | 6 | 4-N | C | C | C | C | 2-Cl | H | H | H |
| 203 | 3 | H | H | 4 | 4-O | sb | N | C | C | 3-CH₃ | 5-CH₃ | — | Ac |
| 204 | 3 | H | H | 4 | 4-O | sb | N | C | C | 3-CH₃ | 5-CH₃ | — | H |

-continued

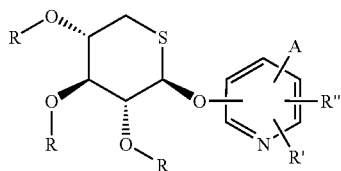

with A =

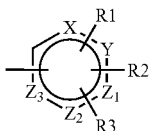

| Ex. | Pos-N | R' | R" | Pos-A | X | Y | Z1 | Z2 | Z3 | R₁ | R₂ | R₃ | R |
|---|---|---|---|---|---|---|---|---|---|---|---|---|---|
| 205 | 3 | 6-CH₃ | H | 2 | 3-N | C | C | C | C | H | H | H | Ac |
| 206 | 3 | 6-CH₃ | H | 2 | 3-N | C | C | C | C | H | H | H | H |
| 207 | 3 | 6-CH₃ | H | 2 | 4-N | C | C | C | C | H | H | H | Ac |
| 208 | 3 | 6-CH₃ | H | 2 | 4-N | C | C | C | C | H | H | H | H |
| 209 | 3 | H | H | 6 | 4-N | C | C | C | C | 2-F | H | H | Ac |
| 210 | 3 | H | H | 6 | 4-N | C | C | C | C | 2-F | H | H | H |
| 211 | 3 | H | H | 2 | 5-N | C | N | C | C | H | H | H | Ac |
| 212 | 3 | H | H | 2 | 5-N | C | N | C | C | H | H | H | H |
| 213 | 3 | 5-F | H | 6 | 3-N | C | C | C | C | 6-F | H | H | Ac |
| 214 | 3 | 5-F | H | 6 | 3-N | C | C | C | C | 6-F | H | H | H |
| 215 | 3 | 5-F | H | 6 | 3-N | C | C | C | C | 6-CH₃ | H | H | Ac |
| 216 | 3 | 5-F | H | 6 | 3-N | C | C | C | C | 6-CH₃ | H | H | H |
| 217 | 3 | H | H | 5 | 5-N | C | N | C | C | 2-OCH₃ | H | H | Ac |
| 218 | 3 | H | H | 5 | 5-N | C | N | C | C | 2-OCH₃ | H | H | H |
| 219 | 3 | 5-F | H | 6 | 4-N | C | C | C | C | 2-CH₃ | H | H | Ac |
| 220 | 3 | 5-F | H | 6 | 4-N | C | C | C | C | 2-CH₃ | H | H | H |
| 221 | 3 | 5-F | H | 6 | 3-N | C | C | C | C | 2-OCH₃ | H | H | Ac |
| 222 | 3 | 5-F | H | 6 | 3-N | C | C | C | C | 2-OCH₃ | H | H | H |
| 223 | 3 | 5-F | H | 6 | 4-N | sb | N | C | C | 1-CH₃ | H | H | Ac |
| 224 | 3 | 5-F | H | 6 | 4-N | sb | N | C | C | 1-CH₃ | H | H | H |
| 225 | 3 | 5-F | H | 6 | 4-O | sb | N | C | C | 3-CH₃ | 5-CH₃ | — | Ac |
| 226 | 3 | 5-F | H | 6 | 4-O | sb | N | C | C | 3-CH₃ | 5-CH₃ | — | H |
| 227 | 3 | H | H | 6 | 5-N | C | N | C | C | 2-OCH₃ | H | H | Ac |
| 228 | 3 | H | H | 6 | 5-N | C | N | C | C | 2-OCH₃ | H | H | H |
| 229 | 3 | 5-F | H | 6 | 5-N | C | N | C | C | H | H | H | Ac |
| 230 | 3 | 5-F | H | 6 | 5-N | C | N | C | C | H | H | H | H |
| 231 | 3 | H | H | 5 | 2-N | C | C | C | C | 3-Cl | H | H | Ac |
| 232 | 3 | H | H | 5 | 2-N | C | C | C | C | 3-Cl | H | H | H |
| 233 | 3 | H | H | 5 | 2-N | C | C | C | C | 5-CH₃ | H | H | Ac |
| 234 | 3 | H | H | 5 | 2-N | C | C | C | C | 5-CH₃ | H | H | H |
| 235 | 3 | H | H | 5 | 2-N | C | C | C | C | 4-CH₃ | H | H | Ac |
| 236 | 3 | H | H | 5 | 2-N | C | C | C | C | 4-CH₃ | H | H | H |
| 237 | 3 | H | H | 5 | 2-N | C | C | C | C | 6-CH₃ | H | H | Ac |
| 238 | 3 | H | H | 5 | 2-N | C | C | C | C | 6-CH₃ | H | H | H |
| 239 | 3 | 6-CH₃ | H | 2 | 4-O | sb | N | C | C | 3-CH₃ | 5-CH₃ | — | H |
| 240 | 3 | H | H | 2 | 3-N | C | C | C | C | 6-F | H | H | H |
| 241 | 4 | H | H | 2 | 4-O | sb | N | C | C | 3-CH₃ | 5-CH₃ | — | H |
| 242 | 3 | H | H | 5 | 3-N | C | C | C | C | 4-OCH₃ | H | H | H |
| 243 | 3 | H | H | 6 | 3-N | C | C | C | C | 4-OCH₃ | H | H | H |
| 244 | 3 | H | H | 5 | 4-N | C | C | C | C | 2-CH₃ | H | H | H |
| 245 | 3 | H | H | 6 | 4-N | C | C | C | C | 2-CH₃ | H | H | H |
| 246 | 3 | H | H | 6 | 3-N | C | C | C | C | 5-Cl | H | H | Ac |
| 247 | 3 | H | H | 6 | 3-N | C | C | C | C | 5-Cl | H | H | H |
| 248 | 3 | H | H | 5 | 3-N | C | C | C | C | 4-CH₃ | H | H | Ac |
| 249 | 3 | H | H | 5 | 3-N | C | C | C | C | 4-CH₃ | H | H | H |
| 252 | 3 | H | H | 2 | 5-N | sb | N | N | N | H | — | — | Ac |
| 253 | 3 | H | H | 2 | 5-N | sb | N | N | N | H | — | — | H |
| 254 | 3 | 2-F | H | 6 | 4-O | sb | N | C | C | 3-CH₃ | 5-CH₃ | — | Ac |
| 255 | 3 | 2-F | H | 6 | 4-O | sb | N | C | C | 3-CH₃ | 5-CH₃ | — | H |
| 256 | 3 | 2-F | H | 6 | 3-N | C | C | C | C | 2-F | H | H | Ac |
| 257 | 3 | 2-F | H | 6 | 3-N | C | C | C | C | 2-F | H | H | H |
| 258 | 3 | 2-F | H | 6 | 5-N | C | N | C | C | H | H | H | Ac |
| 259 | 3 | 2-F | H | 6 | 5-N | C | N | C | C | H | H | H | H |
| 260 | 3 | 2-F | H | 6 | 3-N | C | C | C | C | 6-F | H | H | Ac |
| 261 | 3 | 2-F | H | 6 | 3-N | C | C | C | C | 6-F | H | H | H |
| 262 | 3 | 2-F | H | 6 | 4-N | C | C | C | C | 2-F | H | H | Ac |
| 263 | 3 | 2-F | H | 6 | 4-N | C | C | C | C | 2-F | H | H | H |

-continued

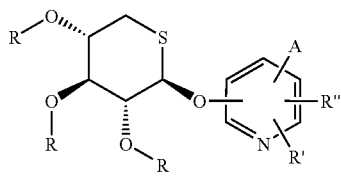

with A =

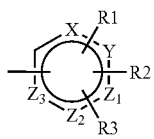

| Ex. | Pos-N | R' | R" | Pos-A | X | Y | Z1 | Z2 | Z3 | R₁ | R₂ | R₃ | R |
|---|---|---|---|---|---|---|---|---|---|---|---|---|---|
| 264 | 3 | 2-F | H | 6 | 4-N | sb | N | C | C | 1-CH₃ | H | H | Ac |
| 265 | 3 | 2-F | H | 6 | 4-N | sb | N | C | C | 1-CH₃ | H | H | H |
| 266 | 3 | 2-F | H | 6 | 3-N | C | C | C | C | 6-CH₃ | H | H | Ac |
| 267 | 3 | 2-F | H | 6 | 3-N | C | C | C | C | 6-CH₃ | H | H | H |
| 268 | 3 | 2-F | H | 6 | 4-N | C | C | C | C | 2-CH₃ | H | H | Ac |
| 269 | 3 | 2-F | H | 6 | 4-N | C | C | C | C | 2-CH₃ | H | H | H |
| 270 | 3 | 2-F | H | 6 | 3-N | C | C | C | C | 6-CN | H | H | Ac |
| 271 | 3 | 2-F | H | 6 | 3-N | C | C | C | C | 6-CN | H | H | H |
| 272 | 3 | 5-F | H | 6 | 3-N | C | C | C | C | H | H | H | Ac |
| 273 | 3 | 5-F | H | 6 | 3-N | C | C | C | C | H | H | H | H |
| 274 | 3 | 5-F | H | 6 | 4-N | C | C | C | C | 2-F | H | H | Ac |
| 275 | 3 | 5-F | H | 6 | 4-N | C | C | C | C | 2-F | H | H | H |
| 276 | 3 | 2-Cl | H | 5 | 5-N | C | N | C | C | H | H | H | Ac |
| 277 | 3 | 2-Cl | H | 5 | 5-N | C | N | C | C | H | H | H | H |
| 278 | 3 | 2-Cl | H | 5 | 5-N | C | C | C | C | 6-F | H | H | Ac |
| 279 | 3 | 2-Cl | H | 5 | 3-N | C | C | C | C | 6-F | H | H | H |
| 280 | 3 | 2-Cl | H | 6 | 5-N | C | N | C | C | H | H | H | Ac |
| 281 | 3 | 2-Cl | H | 6 | 5-N | C | N | C | C | H | H | H | H |
| 282 | 3 | 2-F | H | 5 | 2-N | C | C | C | C | H | H | H | Ac |
| 283 | 3 | 2-F | H | 5 | 2-N | C | C | C | C | H | H | H | H |
| 284 | 3 | 2-F | H | 5 | 5-N | C | N | C | C | H | H | H | Ac |
| 285 | 3 | 2-F | H | 5 | 5-N | C | N | C | C | H | H | H | H |

In the above table:
  Pos-N indicates the position of the thioxyloside group with respect to the nitrogen atom of the pyridine ring,
  Pos-A indicates the position of the heterocycle A with respect to the nitrogen atom of the pyridine ring,
  X indicates the nature of the primary heteroatom of the heterocycle A and its position with respect to the bond of the heterocycle A with the pyridine ring,
  "sb" means single bond,
  for the R1, R2 and R3 substituents, the figure indicates the position of the substituent on the heterocycle A with respect to the heteroatom X.
By way of example, compound No. 226 is the compound of formula:

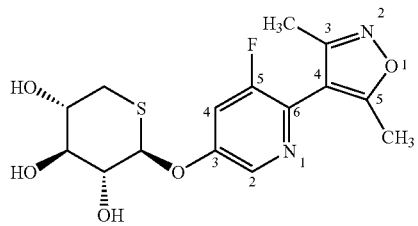

The antithrombotic activity of the compounds according to the invention was studied in vivo in rats by virtue of a test in which a venous thrombosis is reproduced.

The venous thrombosis was induced according to the protocol described in *Thromb. Haemost.*, 1992, 67(1), 176-179. The activity via the oral route was studied according to the procedure described below.

The experiment is carried out on non-fasting male Wistar rats weighing from 250 to 280 g and divided into groups of 10 animals each. The test products are administered orally (intubation) in solution or in suspension in a 0.5% solution of methylcellulose in water. The concentrations of the compounds are calculated so as to bring about the absorption of an amount of solution of 10 ml/kg orally. A thrombosis is induced at a time T after the administration of the product and the thrombus formed is removed and weighed. In order to induce this thrombosis, a venous stasis is brought about under hypercoagulation, according to the technique described by Wessler (*J. Applied Physiol.*, 1959, 943-946), using a solution of activated factor X (Xa), supplied by Biogenic (Montpellier) and comprising a dose of 7.5 nKat/kg, as hypercoagulant. The venous stasis is brought about 10 seconds exactly after the injection of the hypercoagulant. The activity of the test compounds is monitored at various doses, after they have been administered. The thrombosis is induced 2 hours after the administration of the compound. By way of example, the results of the above tests are given in the following table for a few compounds according to the invention (the activity is expressed by the percentage of inhibition of the formation of the thrombus, observed in the presence of the compound according to the invention, with respect to the weight of the thrombus formed in the absence of the compound).

TABLE I

| | Activity via the oral route | | |
|---|---|---|---|
| Example No. | Dose (mg/kg) | Time (h) | Activity |
| 22 | 6 | 2 | 100 |
| 24 | 6 | 2 | 96 |
| 30 | 6 | 2 | 97 |
| 40 | 6 | 2 | 96 |
| 108 | 6 | 2 | 95 |
| 122 | 6 | 2 | 93 |
| 130 | 6 | 2 | 91 |
| 140 | 6 | 2 | 96 |
| 142 | 6 | 2 | 97 |
| 224 | 6 | 2 | 99 |
| 226 | 6 | 2 | 97 |

These results show that the compounds according to the invention exhibit a good antithrombotic activity after administration via the oral route.

The present invention thus includes a compound of formula (I) according to the invention and its salts with an acid, solvates and hydrates which are pharmaceutically acceptable for their use as medicaments. The compound of formula (I) or one of its pharmaceutically acceptable salts, solvates or hydrates can be used in the preparation of an antithrombotic medicament intended in particular for the treatment or inhibition of disorders of the venous or arterial circulation and especially for correcting certain sensitive venous hematological parameters, or for compensating for cardiac insufficiency. The compound of formula (I) or one of its pharmaceutically acceptable salts, solvates or hydrates can also be used in the preparation of a medicament intended for the inhibition of restenosis after transluminal arterial or coronary angioplasty or else to inhibit or treat pathologies of thromboembolic type which risk occurring subsequent, for example, to a surgical action, such as hip or knee arthroplasty. The compounds according to the invention can also be used as active substances of medicaments intended to inhibit strokes or heart attacks.

The present invention thus also includes pharmaceutical compositions comprising a compound of formula (I) or one of its pharmaceutically acceptable salts, solvates or hydrates. These pharmaceutical compositions generally comprise suitable excipients. Said excipients are chosen according to the pharmaceutical form desired and the method of administration desired, in particular oral or injectable.

These pharmaceutical compositions are prepared according to conventional methods well known to a person skilled in the art. For example, the compounds according to the invention can be formulated with physiologically acceptable excipients in order to obtain an injectable form to be used directly, an injectable form to be prepared at the time of use or a solid form for oral administration, such as, for example, a hard gelatin capsule or a tablet.

By way of example, an injectable form can be prepared preferably by lyophilization of a filtered and sterilized solution comprising the compound according to the invention and a soluble excipient in an amount necessary and sufficient to obtain an isotonic solution after addition at the time of use of water for injection. The solution obtained can be administered either in a single subcutaneous or intramuscular injection or in the form of a slow infusion. A form which can be administered orally will preferably be presented in the form of a hard gelatin capsule comprising the finely milled or better still micronized compound of the invention mixed with excipients known to a person skilled in the art, such as, for example, lactose, pregelatinized starch and magnesium stearate.

In order to obtain the desired therapeutic or prophylactic effect, each unit dose can comprise from 10 to 500 mg of at least one compound according to the invention.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A compound selected from the group consisting of:
a) pentapyranosyl compounds of formula:

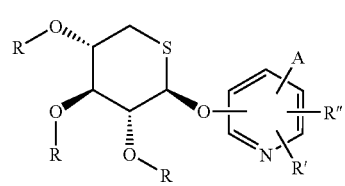

I wherein:
the pentapyranosyl group represents a 5-thio-β-D-xylopyranosyl group,
R represents a hydrogen atom or a $C_2$-$C_6$ acyl group,
R' and R" each independently represent a hydrogen atom, a halogen atom, a $C_1$-$C_4$ alkyl group or a 6-fluoro-3-pyridinyl group,
A represents a 5- or 6-membered aromatic heterocycle of formula:

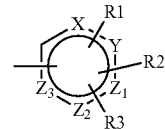

wherein:
X represents a nitrogen, oxygen or sulfur atom,
Y represents a carbon atom or a single bond,
$Z_1$, $Z_2$ and $Z_3$ each independently represent a carbon or nitrogen atom,
$R_1$, $R_2$ and $R_3$ each independently represent a hydrogen atom, a halogen atom, a cyano group, a $C_1$-$C_4$ alkyl group, a $C_1$-$C_4$ alkoxy group or a trifluoromethyl group; or
$R_1$ and $R_2$ together with the atoms of the heterocycle to which they are attached form an aromatic ring comprising 6 carbon atoms, whereby A represents a fused bicyclic group, and
b) addition salts thereof.

2. A compound as claimed in claim 1, wherein the 5-thio-β-D-xylopyranosyl group is in the 3 position on the pyridine ring.

3. A compound as claimed in claim 1, wherein R' and R" each independently represent a hydrogen atom, a halogen atom or a methyl group.

4. A compound as claimed in claim 1, wherein A represents a pyridinyl ring.

5. A compound as claimed in claim 1, wherein R represents a hydrogen atom.

6. A compound as claimed in claim 1, wherein R represents a COCH$_3$ group.

7. A compound as claimed in claim 1, wherein A represents a fused benzofuranyl or benzothienyl group.

8. A process for making a compound as claimed in claim 1, said process comprising:
   a) reacting a pyridinol starting compound of formula II:

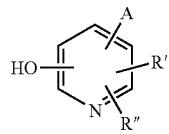

wherein:
R' and R" each independently represent a hydrogen atom, a halogen atom or a C$_1$-C$_4$ alkyl group,
A represents a 5- or 6-membered aromatic ring of formula:

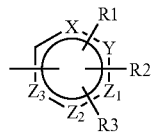

wherein:
X represents a nitrogen, oxygen or sulfur atom,
Y represents a carbon atom or a single bond,
Z$_1$, Z$_2$ and Z$_3$ each independently represent a carbon or nitrogen atom,
R$_1$, R$_2$ and R$_3$ each independently represent a hydrogen atom, a halogen atom, a cyano group, a C$_1$-C$_4$ alkyl group, a C$_1$-C$_4$ alkoxy group, or a trifluoromethyl group; or
R$_1$ and R$_2$ together with the atoms of the heterocycle to which they are attached form an aromatic ring comprising 6 carbon atoms, whereby A represents a fused bicyclic group;
with a 5-thioxylopyranose starting compound of formula:

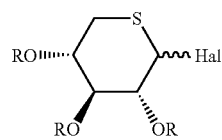

wherein Hal represents a halogen and R represents a C$_2$-C$_6$ acyl group, in an aprotic solvent, in the presence of a silver salt or of a zinc salt, in an anhydrous medium, at a temperature of between 25 and 110° C. and for 1 to 10 hours, to yield a compound of formula I:

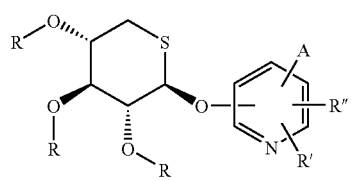

wherein A, R, R' and R" retain the same meanings as in the starting compounds;

b) optionally reacting the compound of formula I obtained above with a solution of ammonia in methanol to effect deacylation, whereby the acyl group is replaced by hydrogen atoms to yield a compound of formula Ia:

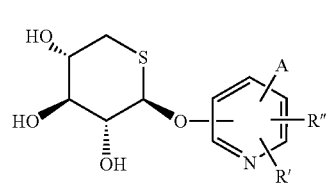

wherein R$_1$ and R$_2$ retain the same meanings as above; and
c) optionally reacting the compound of formula I or Ia obtained above with an acid to yield a corresponding addition salt.

9. A process as claimed in claim 8, wherein A represents a fused benzofuranyl or benzothienyl group, and Hal represents bromine.

10. A process as claimed in claim 8, wherein the deacylation in (b) is effected with a catalytic amount of a metal alkoxide in methanol at a temperature of between 0 and 30° C. and for 0.5 to 2 hours to yield the compound of formula Ia from the compound of formula I wherein R represents a C$_2$-C$_6$ acyl group.

11. A process as claimed in claim 10, wherein the metal alkoxide is sodium methoxide.

12. A process for making a compound as claimed in claim 1, said process comprising:
   a) reacting the tetraacetylthioxylose starting compound of formula:

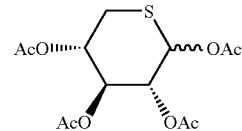

wherein Ac represents the acetyl group,
with a pyridinol starting compound of formula II:

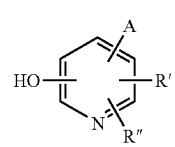

wherein:
R' and R" each independently represent a hydrogen atom, a halogen atom or a C$_1$-C$_4$ alkyl group,
A represents a 5- or 6-membered aromatic ring of formula:

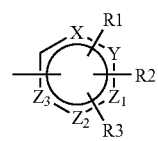

wherein:
X represents a nitrogen, oxygen or sulfur atom,
Y represents a carbon atom or a single bond,
Z$_1$, Z$_2$ and Z$_3$ each independently represent a carbon or nitrogen atom, $R_1$, $R_2$ and $R_3$ each independently represent a hydrogen atom, a halogen atom, a cyano group, a $C_1$-$C_4$ alkyl group, a $C_1$-$C_4$ alkoxy group or a trifluoromethyl group; or $R_1$ and $R_2$ together with the atoms of the heterocycle to which they are attached form an aromatic ring comprising 6 carbon atoms, whereby A represents a fused bicycle group, in an aprotic solvent, in the presence of a Lewis acid catalyst, at a temperature of between 20 and 60° C. and for 1 to 2 hours, to yield a compound of formula Ib:

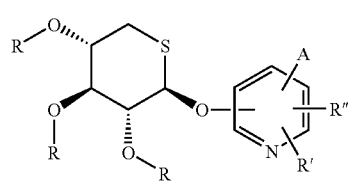

Ib wherein A, R, R' and R'' retain the same meanings as in the starting compounds, and b) optionally exchanging the acetyl groups for hydrogen atoms to yield a compound of formula Ia:

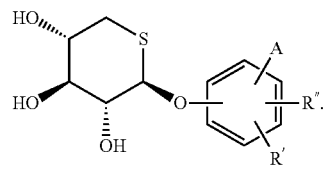

Ia

13. A process as claimed in claim 12, wherein A represents a fused benzofuranyl or benzothienyl group.

14. A process for making a compound as claimed in claim 1, said process comprising:
a) reacting a starting compound of formula:

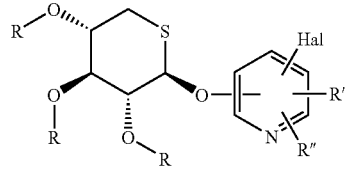

wherein:
Hal is a halogen atom,
R' and R'' each independently represent a hydrogen atom, a halogen atom or a $C_1$-$C_4$ alkyl group, and
R represents a hydrogen atom or a $C_2$-$C_6$ acyl group;
with a heteroarylboronic acid or an alkyl heteroarylboronate starting compound of formula:

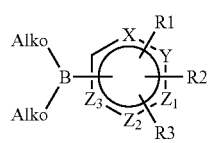

wherein Alk represents a hydrogen atom or a $C_1$-$C_4$ akyl group, and the group:

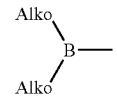

may additionally represent a pinacolatoboryl group,
in the presence of a palladium catalyst, of a polar solvent and of cesium fluoride or sodium carbonate, at a temperature of between 70° C. and 150° C. for 5 minutes to 72 hours, to yield a compound of formula:

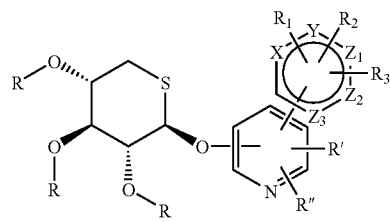

wherein R, $R_1$, $R_2$, $R_3$, R', R'', X, Y, $Z_1$, $Z_2$ and $Z_3$ retain the same meanings as in the starting compounds.

15. A process as claimed in claim 14, wherein Hal represents bromine or iodine, and R' and R'' each independently represent a halogen atom other than bromine or iodine.

16. A process for making a compound as claimed in claim 1, said process comprising:
a) reacting a glycosylated pyridineboronic acid or a glycosylated pyridinylboronate starting compound of formula:

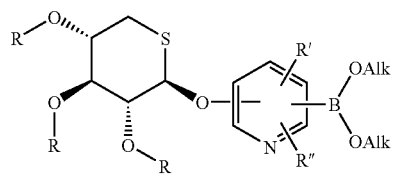

wherein:
R represents a hydrogen atom or a $C_2C_6$ acyl group,
R' and R'' each independently represent a hydrogen atom, a halogen atom or a $C_1$-$C_4$ alkyl group, and
Alk represents a hydrogen atom or a $C_1$-$C_4$ alkyl group,
with a heteroaryl halide starting compound of formula:

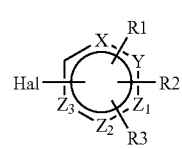

wherein:
Hal represents a halogen,
$R_1$, $R_2$ and $R_3$ each independently represent a hydrogen atom, a halogen atom, a cyano group, $C_1$-$C_4$ alkyl group, a $C_1$-$C_4$ alkoxy soup or a tifluoromethyl group; or R₁ and R₂ together with the atoms of the heterocycle to which they are attached form an aromatic ring comprising 6 carbon atoms, whereby A represents a fused bicyclic group, in the presence of a palladium catalyst, of a polar protic solvent, and cesium fluoride or sodium carbonate, at a temperature of between 70° C. and 150° C. for 5 minutes to 72 hours, to yield a compound of formula:

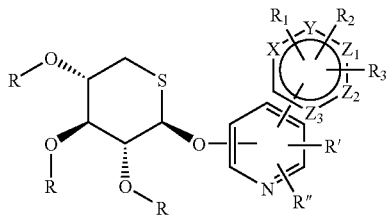

wherein R, R₁, R₂, R₃, R', R", X, Y, Z₁, Z₂ and Z₃ retain the same meanings as in the starting compounds.

17. A process as claimed in claim 16, wherein R' and R" each independently represent a halogen atom other than bromine or iodine; Hal represents bromine or iodine; R₁, R₂ and R₃ each represent a fluorine atom; A represents a benzofuranyl or benzothienyl group, and said polar protic solvent is methanol.

18. A pharmaceutical composition comprising a compound as claimed in any claim 1, and at least one pharmaceutically acceptable carrier or auxiliary.

19. A method of treating or inhibiting a condition selected from the group consisting of thrombosis, cardiac insufficiency, restenosis, and thromboembolism in a subject, said method comprising administering to said subject a pharmacologically effective amount of a compound as claimed in claim 1.

20. A method as claimed in claim 19, wherein said condition is venous thrombosis or restenosis subsequent to an angioplasty.

* * * * *